(12) United States Patent
Han et al.

(10) Patent No.: US 10,093,671 B2
(45) Date of Patent: Oct. 9, 2018

(54) 2-OXO-6,7-DIHYDROBENZO[A] QUINOLIZINE-3-CARBOXYLIC ACID DERIVATIVES FOR THE TREATMENT AND PROPHYLAXIS OF HEPATITIS B VIRUS INFECTION

(71) Applicant: Hoffmann-La Roche Inc., Little Falls, NJ (US)

(72) Inventors: Xingchun Han, Shanghai (CN); Min Jiang, Shanghai (CN); Song Yang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/674,810

(22) Filed: Aug. 11, 2017

(65) Prior Publication Data
US 2017/0342069 A1    Nov. 30, 2017

Related U.S. Application Data

(63) Continuation of application No. PCT/EP2016/052585, filed on Feb. 8, 2016.

(30) Foreign Application Priority Data

Feb. 11, 2015 (WO) ................ PCT/CN2015/072741

(51) Int. Cl.
*C07D 471/04* (2006.01)

(52) U.S. Cl.
CPC .................................. *C07D 471/04* (2013.01)

(58) Field of Classification Search
None
See application file for complete search history.

(56) References Cited

U.S. PATENT DOCUMENTS 9,637,485 B2 *  5/2017  Han ..................... C07D 471/04

FOREIGN PATENT DOCUMENTS

JP           S60197684 A        10/1985

OTHER PUBLICATIONS

Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Mohebbi et al., An Overview of Hepatitis B Virus Surface Antigen Secretion Inhibitors. Frontier in Microbiology, 2018, 9, 1-9.*
Acs et al., "Hepatitis B virus produced by transfected Hep G2 cells causes hepatitis in chimpanzees" Proc Natl Acad Sci USA 84:4641-4644 ( 1987).
Ansel et al., "Pharmaceutical Dosage Forms and Drug Delivery Systems" 6th Ed.:456-457 (1995).
Bastin et al., "Salt Selection and Optimisation Procedures for Pharmaceutical New Chemical Entities" Organic Process Research & Development 4:427-435 ( 2000).
Belloni et al., "IFN-α inhibits HBV transcription and replication in cell culture and in humanized mice by targeting the epigenetic regulation of the nuclear cccDNa minichromosome" J Clin Invest 122(2):529-537 (Feb. 2012).
Buster et al., "Peginterferon alpha-2b is safe and effective in HBeAg-Positive chronic hepatitis B patients with advanced fibrosis" Hepatology 46:388-394 ( 2007).
Fisicaro et al., "Antiviral intrahepatic T-cell responses can be restored by blocking programmed death-1 pathway in chronic hepatits B" Gastroenterology 138:682-693 ( 2010).
Geng et al., "Small-molecule inhibitors for the treatment of hepatitis B virus documented in patents" Mini Reviews in Medicinal Chemistry 13(5):749-776 (Apr. 1, 2013).
Janssen et al., "Pegylated interferon alfa-2b alone or in combination with lamivudine for HBeAg-positive chronic hepatitis B: a randomised trial" Lancet 365:123-129 (Jan. 8, 2005).
Kondo et al., "Hepatitis B surface antigen could contribute to the immunopathogenesis of hepatitis B virus infection" ISRN Gastroenterology (Article ID 935295), 2013.
Kondo et al., "Recovery of functional cytotoxic T lymphocytes during lamivudine therapy by acquiring muti-specificity" J Med Virol 74:425-433 ( 2004).
Kumar et al., "Hepatitis B virus regulatory HBx protein binds to adaptor protein IPS-1 and inhibits the activation of beta interferon" J Virol 85(2):987-995 (Jan. 2011).
Lambert et al., "Posttranslational N-glycosylation of the hepatitis B virus large envelope protein" Virol J 4( Suppl 1-9):45 (May 2007).
Locarnini, S., "Molecular virology and the development of resistant mutants: implications for therapy" Semin Liver Dis 25( Suppl 1):9-19 ( 2005).
Mao et al., "Indoleamine 2,3-dioxygenase mediates the antiviral effect of gagamma interferon against hepatitis B virus in human hepatocyte-derived cells" J Virol 85(2):1048-1057 (Jan. 2011).

(Continued)

*Primary Examiner* — Po-Chih Chen
(74) *Attorney, Agent, or Firm* — Brian L. Buckwalter

(57) ABSTRACT

The invention provides novel compounds having the general formula:

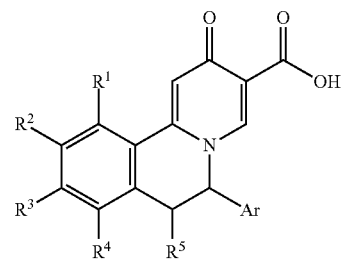

wherein $R^1$, $R^2$, $R^3$, $R^4$, $R^5$ and Ar are as described herein, compositions including the compounds and methods of using the compounds.

17 Claims, No Drawings

(56) References Cited

OTHER PUBLICATIONS

Mao et al., "Inhibition of hepatitis B virus replication by the host zinc finger antiviral protein" PLoS Pathogens 9(7 Suppl 1-18):e1003494 (Jul. 2013).

Marcellin et al., "Peginterferon alfa-2a alone, lamivudine alone, and the two in combination in patients with HBeAg-negative chronic hepatitis B" New E J Med 351(12):1206-1217 (Sep. 16, 2004).

Nayersina et al., "HLA A2 restricted cytotoxic T lymphocyte responses to multiple hepatitis B surface antigen epitopes during hepatitis B virus infection" J Immunol 150:4659-4671 (May 15, 1993).

Op den Brouw et al., "Hepatitis B virus surface antigen impairs myeloid dendritic cell function: a possible immune escape mechanism of hepatitis B virus" Immunol 126:280-290 ( 2008).

Quasdorff et al., "Control of hepatitis B virus at the level of transcription" J Viral Hepatitis 17:527-536 ( 2010).

Schulze et al., "Hepatitis B virus infection initiates with a large surface protein-dependent binding to heparan sulfate proteoglycans" Hepatology 46:1759-1768 ( 2007).

Shi et al., "Hepatitis B virus suppresses the functional interaction between natural killer cells and plasmacytoid dendritic cells" J Viral Hepatitis 19:e26-e33 ( 2012).

Wieland et al., "Stealth and cunning: hepatitis B and hepatitis C viruses" J Virol 79(15):9369-9380 (Aug. 2005).

Woltman et al., "Hepatitis B virus lacks immune activating capacity, but actively inhibits plasmacytoid dendritic cell function" PLoS One 6(1 Suppl 1-14):e15324 (Jan. 2011).

Yan et al., "Molecular determinants of hepatitis B and D virus entry restriction in mouse sodium taurocholate cotransporting polypeptide" J Virol 87(14):7977-7991 (Jul. 2013).

Ying-Rui Wu et al., "Two New Quaternary Alkaloids and Anti-Hepatitis B Virus Active Constituents from Corydalis saxicola" Planta Med 73:787-791 ( 2007).

Fecik et al., "Chiral DNA gyrase inhibitors. 3. Probing the chiral preference of the active site of DNA gyrase. Synthesis of 10-fluoro-6-methyl-6,7-dihydro-9-piperazinyl-2H-benzo[a]quinolizin-20-one-3-carboxylic acid analogues" J Med Chem 48(4):1229-1236 ( 2005).

Georgopapadakou et al., "Monocyclic and tricyclic analogs of quinolones: mechanism of action" Antimicrob Agents CH 31(4):614 (Apr. 1987).

* cited by examiner

2-OXO-6,7-DIHYDROBENZO[A]QUINOLIZINE-3-CARBOXYLIC ACID DERIVATIVES FOR THE TREATMENT AND PROPHYLAXIS OF HEPATITIS B VIRUS INFECTION

RELATED APPLICATIONS

This application is a continuation of International Application No. PCT/EP2016/052585, filed Feb. 8, 2016, claiming priority to earlier International Application No. PCT/CN2015/072741 filed Feb. 11, 2015, the contents of which are incorporated herein by reference.

The present invention relates to organic compounds useful for therapy and/or prophylaxis in a mammal, and in particular to HBsAg (HBV Surface antigen) inhibitors and HBV DNA production inhibitors useful for treating HBV infection.

FIELD OF THE INVENTION

The present invention relates to novel 2-oxo-6,7-dihydrobenzo[a]quinolizine-3-carboxylic acid derivatives having pharmaceutical activity, their manufacture, pharmaceutical compositions containing them and their potential use as medicaments.

The present invention relates to compounds of formula I

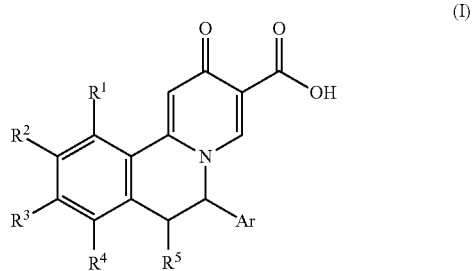

wherein $R^1$ to $R^5$ and Ar are as described below, or to pharmaceutically acceptable salts, or to enantiomers thereof.

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, A., P. Gripon & S. Urban. *Hepatology*, 46, (2007), 1759-68) and via the specific binding of HBV surface antigens (HBsAg) to the hepatocyte sodium-taurocholate cotransporting polypeptide (NTCP) receptor (Yan, H. et al. *J Virol*, 87, (2013), 7977-91). Once the virion has entered the cell, the viral cores and the encapsidated RC DNA are transported by host factors, via a nuclear localization signal, into the nucleus through the Impβ/Impa nuclear transport receptors. Inside the nucleus, host DNA repair enzymes convert the RC DNA into cccDNA. cccDNA acts as the template for all viral mRNAs and as such, is responsible for HBV persistence in infected individuals. The transcripts produced from cccDNA are grouped into two categories; Pregenomic RNA (pgRNA) and subgenomic RNA. Subgenomic transcripts encode for the three envelopes (L, M and S) and X proteins, and pgRNA encodes for Pre-Core, Core, and Pol proteins (Quasdorff, M. & U. Protzer. *J Viral Hepat*, 17, (2010), 527-36). Inhibition of HBV gene expression or HBV RNA synthesis leads to the inhibition of HBV viral replication and antigens production (Mao, R. et al. *PLoS Pathog*, 9, (2013), e1003494; Mao, R. et al. *J Virol*, 85, (2011), 1048-57). For instance, IFN-α was shown to inhibit HBV replication and viral HBsAg production by decreasing the transcription of pgRNA and subgenomic RNA from the HBV covalently closed circular DNA (cccDNA) minichromosome. (Belloni, L. et al. *J Clin Invest*, 122, (2012), 529-37; Mao, R. et al. *J Virol*, 85, (2011), 1048-57). All HBV viral mRNAs are capped and polyadenylated, and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence. The mature nucleocapsids containing RC DNA are enveloped with cellular lipids and viral L, M, and S proteins and then the infectious HBV particles are then released by budding at the intracellular membrane (Locarnini, S. *Semin Liver Dis*, (2005), 25 Suppl 1, 9-19). Interestingly, non-infectious particles are also produced that greatly outnumber the infectious virions. These empty, enveloped particles (L, M and S) are referred to as subviral particles. Importantly, since subviral particles share the same envelope proteins and as infectious particles, it has been surmised that they act as decoys to the host immune system and have been used for HBV vaccines. The S, M, and L envelope proteins are expressed from a single ORF that contains three different start codons. All three proteins share a 226aa sequence, the S-domain, at their C-termini. M and L have additional pre-S domains, Pre-S2 and Pre-S2 and Pre-S1, respectively. However, it is the S-domain that has the HBsAg epitope (Lambert, C. & R. Prange. *Virol J*, (2007), 4, 45).

The control of viral infection needs a tight surveillance of the host innate immune system which could respond within minutes to hours after infection to impact on the initial growth of the virus and limit the development of a chronic and persistent infection. Despite the available current treatments based on IFN and nucleos(t)ide analogues, the Hepatitis B virus (HBV) infection remains a major health problem worldwide which concerns an estimated 350 million chronic carriers who have a higher risk of liver cirrhosis and hepatocellular carcinoma.

The secretion of antiviral cytokines in response to HBV infection by the hepatocytes and/or the intra-hepatic immune cells plays a central role in the viral clearance of infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). The persistent exposure to HBsAg and other viral antigens can lead to HBV-specific T-cell deletion or to progressive functional impairment (Kondo et al. *Journal of Immunology* (1993), 150, 4659-4671; Kondo et al. *Journal of Medical Virology* (2004), 74, 425-433; Fisicaro et al. *Gastroenterology*, (2010), 138, 682-93;). Moreover HBsAg has been reported to suppress the function of immune cells such as monocytes, dendritic cells (DCs) and natural killer (NK) cells by direct interaction (Op den Brouw et al. *Immunology*, (2009b), 126, 280-9; Woltman et al. *PLoS One*, (2011), 6, e15324; Shi et al. *J Viral Hepat.* (2012), 19, e26-33; Kondo et al. *ISRN Gasteroenterology*, (2013), Article ID 935295).

HBsAg quantification is a significant biomarker for prognosis and treatment response in chronic hepatitis B. However the achievement of HBsAg loss and seroconversion is rarely observed in chronically infected patients but remains the ultimate goal of therapy. Current therapy such as Nucleos(t)ide analogues are molecules that inhibit HBV DNA synthesis but are not directed at reducing HBsAg level. Nucleos(t)ide analogs, even with prolonged therapy, have demonstrated rates of HBsAg clearance comparable to those observed naturally (between -1%-2%) (Janssen et al. *Lancet*, (2005), 365, 123-9; Marcellin et al. *N. Engl. J. Med.*, (2004), 351, 1206-17; Buster et al. *Hepatology*, (2007), 46, 388-94). Therefore, targeting HBsAg together with HBV DNA levels in CHB patients may significantly improve CHB patient immune reactivation and remission (Wieland, S. F. & F. V. Chisari. *J Virol*, (2005), 79, 9369-80; Kumar et al. *J Virol*, (2011), 85, 987-95; Woltman et al. *PLoS One*, (2011), 6, e15324; Op den Brouw et al. *Immunology*, (2009b), 126, 280-9).

SUMMARY OF THE INVENTION

The present invention relates to compounds of formula I

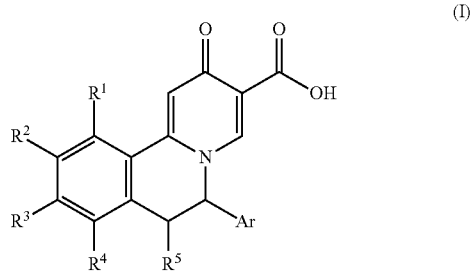

(I)

wherein
$R^1$, $R^2$, $R^3$ and $R^4$ are independently selected from $C_{1-6}$alkyl, halo$C_{1-6}$alkyl, hydrogen, halogen, cyano, amino, $C_{1-6}$alkylamino, di$C_{1-6}$alkylamino, pyrrolidinyl and $OR^6$;
$R^5$ is hydrogen or $C_{1-6}$alkyl;
$R^6$ is hydrogen; $C_{1-6}$alkyl; halo$C_{1-6}$alkyl; $C_{3-7}$cycloalkyl$C_{1-6}$alkyl; phenyl$C_{1-6}$alkyl; hydroxy$C_{1-6}$ alkyl; $C_{1-6}$alkoxy$C_{1-6}$ alkyl; carboxy$C_{1-6}$alkyl; $C_{1-6}$alkylsulfanyl$C_{1-6}$alkyl; $C_{1-6}$alkylsulfonyl$C_{1-6}$ alkyl; cyano$C_{1-6}$alkyl; amino$C_{1-6}$alkyl; $C_{1-6}$alkylamino$C_{1-6}$alkyl; di$C_{1-6}$alkylamino$C_{1-6}$alkyl; $C_{1-6}$alkylcarbonylamino$C_{1-6}$alkyl; $C_{1-6}$alkylsulfonylamino$C_{1-6}$alkyl; $C_{1-6}$ alkoxycarbonylamino$C_{1-6}$alkyl; pyrazolyl$C_{1-6}$alkyl; triazolyl$C_{1-6}$alkyl or heterocycloalkyl$C_{1-6}$ alkyl, wherein heterocycloalkyl is N-containing monocyclic heterocycloalkyl;
Ar is phenyl; phenyl substituted by one, two or three groups independently selected from $C_{1-6}$ alkyl, $C_{1-6}$alkoxy, hydroxy, halogen and phenyl$C_{1-6}$alkoxy; thienyl; thienyl substituted by one, two or three groups independently selected from $C_{1-6}$alkyl, $C_{1-6}$alkoxy, hydroxy, halogen and phenyl$C_{1-6}$alkoxy; benzothiophenyl; benzothiophenyl substituted by one, two or three groups independently selected from $C_{1-6}$alkyl, $C_{1-6}$alkoxy, hydroxy, halogen and phenyl$C_{1-6}$alkoxy; pyridinyl; pyridinyl substituted by one, two or three groups independently selected from $C_{1-6}$alkyl, $C_{1-6}$alkoxy, hydroxy, halogen and phenyl$C_{1-6}$alkoxy; pyrimidinyl; pyrimidinyl substituted by one, two or three groups independently selected from $C_{1-6}$alkyl, $C_{1-6}$alkoxy, hydroxy, halogen and phenyl$C_{1-6}$alkoxy; pyrrolyl; pyrrolyl substituted by one, two or three groups independently selected from $C_{1-6}$alkyl, $C_{1-6}$alkoxy, hydroxy, halogen and phenyl$C_{1-6}$ alkoxy; pyrazolyl; pyrazolyl substituted by one, two or three groups independently selected from $C_{1-6}$alkyl, $C_{1-6}$alkoxy, hydroxy, halogen and phenyl$C_{1-6}$alkoxy; thiazolyl; or thiazolyl substituted by one, two or three groups independently selected from $C_{1-6}$alkyl, $C_{1-6}$alkoxy, hydroxy, halogen and phenyl$C_{1-6}$alkoxy;
or pharmaceutically acceptable salts, or enantiomers thereof.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl, cyclobutyl, cyclopentyl and cyclohexyl.

The term "$C_{1-6}$alkoxy" alone or in combination signifies a group $C_{1-6}$alkyl-O—, wherein the "$C_{1-6}$alkyl" is as defined above; examples for $C_{1-6}$alkoxy are methoxy, ethoxy, propoxy, iso-propoxy, n-butoxy, iso-butoxy, 2-butoxy, tert-butoxy and the like. Particular "$C_{1-6}$alkoxy" groups are methoxy and ethoxy and more particularly methoxy.

The term "halogen" means fluorine, chlorine, bromine or iodine.

The term "halo$C_{1-6}$alkyl" denotes a $C_{1-6}$alkyl group wherein at least one of the hydrogen atoms of the $C_{1-6}$alkyl group has been replaced by same or different halogen atoms, particularly fluoro atoms. Examples of "halo$C_{1-6}$alkyl" include monofluoro-, difluoro- or trifluoro-methyl, -ethyl or -propyl, for example 3,3,3-trifluoropropyl, 3,3-difluoropropyl, 2-fluoroethyl, 2,2-difluoroethyl, 2,2,2-trifluoroethyl, fluoromethyl, difluoromethyl or trifluoromethyl. Particular "halo$C_{1-6}$alkyl" group is difluoromethyl or trifluoromethyl.

The term "monocyclic heterocycloalkyl" is a monovalent saturated or partly unsaturated monocyclic ring system of 4 to 7 ring atoms, comprising 1, 2, or 3 ring heteroatoms selected from N, O and S, the remaining ring atoms being carbon. Examples for monocyclic heterocycloalkyl are aziridinyl, oxiranyl, azetidinyl, oxetanyl, pyrrolidinyl, 2-oxo-pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Particular "monocyclic heterocycloalkyl" groups are piperidinyl, morpholinyl, 2-oxo-pyrrolidinyl, and pyrrolidinyl.

The term "N-containing monocyclic heterocycloalkyl" is a "monocyclic heterocycloalkyl" as defined above wherein at least one of the heteroatoms is N. Examples for "N-containing monocyclic heterocycloalkyl" are aziridinyl, azetidinyl, pyrrolidinyl, 2-oxo-pyrrolidinyl, pyrazolidinyl, imidazolidinyl, oxazolidinyl, isoxazolidinyl, thiazolidinyl, piperidinyl, piperazinyl, morpholinyl, thiomorpholinyl, 1,1-dioxo-thiomorpholin-4-yl, azepanyl, diazepanyl, homopiperazinyl, or oxazepanyl. Particular "N-containing monocyclic heterocycloalkyl" groups are piperidinyl, morpholinyl, 2-oxo-pyrrolidinyl and pyrrolidinyl.

The term "amino" denotes a group of the formula —NR'R" wherein R' and R" are independently hydrogen, $C_{1-6}$alkyl, $C_{1-6}$alkoxy, $C_{3-7}$cycloalkyl, hetero$C_{3-7}$cycloalkyl, aryl or heteroaryl. Alternatively, R' and R", together with the nitrogen to which they are attached, can form a hetero$C_{3-7}$ cycloalkyl.

The term "carbonyl" alone or in combination refers to the group —C(O)—.

The term "cyano" alone or in combination refers to the group —CN.

The term "$C_{1-6}$alkylsulfanyl" denotes the group —S—R', wherein R' is a $C_{1-6}$alkyl group as defined above.

The term "$C_{1-6}$alkylsulfonyl" denotes a group —SO$_2$—R', wherein R' is a $C_{1-6}$alkyl group as defined above. Examples of $C_{1-6}$alkylsulfonyl include methylsulfonyl and ethylsulfonyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitors of HBsAg

The present invention provides (i) novel compounds having the general formula I:

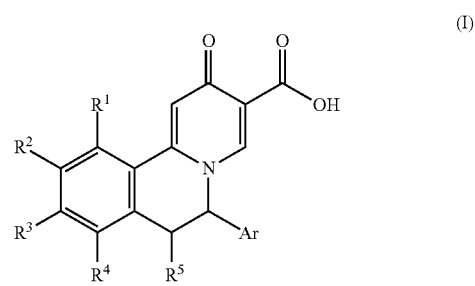

(I)

wherein
$R^1$, $R^2$, $R^3$ and $R^4$ are independently selected from $C_{1-6}$alkyl, halo$C_{1-6}$alkyl, hydrogen, halogen, cyano, amino, $C_{1-6}$alkylamino, di$C_{1-6}$alkylamino, pyrrolidinyl and $OR^6$;
$R^5$ is hydrogen or $C_{1-6}$alkyl;
$R^6$ is hydrogen; $C_{1-6}$alkyl; halo$C_{1-6}$alkyl; $C_{3-7}$cycloalkyl$C_{1-6}$alkyl; phenyl$C_{1-6}$alkyl; hydroxy$C_{1-6}$ alkyl; $C_{1-6}$alkoxy$C_{1-6}$ alkyl; carboxy$C_{1-6}$alkyl; $C_{1-6}$alkylsulfanyl$C_{1-6}$alkyl; $C_{1-6}$alkylsulfonyl$C_{1-6}$ alkyl; cyano$C_{1-6}$ alkyl; amino$C_{1-6}$alkyl; $C_{1-6}$alkylamino$C_{1-6}$alkyl; di$C_{1-6}$ alkylamino$C_{1-6}$alkyl; $C_{1-6}$alkylcarbonylamino$C_{1-6}$alkyl; $C_{1-6}$alkylsulfonylamino$C_{1-6}$alkyl; $C_{1-6}$ alkoxycarbonylamino$C_{1-6}$alkyl; pyrazolyl$C_{1-6}$alkyl; triazolyl$C_{1-6}$alkyl or heterocycloalkyl$C_{1-6}$ alkyl, wherein heterocycloalkyl is N-containing monocyclic heterocycloalkyl;
Ar is phenyl; phenyl substituted by one, two or three groups independently selected from $C_{1-6}$ alkyl, $C_{1-6}$alkoxy, hydroxy, halogen and phenyl$C_{1-6}$alkoxy; thienyl; thienyl substituted by one, two or three groups independently selected from $C_{1-6}$alkyl, $C_{1-6}$alkoxy, hydroxy, halogen and phenyl$C_{1-6}$alkoxy; benzothiophenyl; benzothiophenyl substituted by one, two or three groups independently selected from $C_{1-6}$alkyl, $C_{1-6}$alkoxy, hydroxy, halogen and phenyl$C_{1-6}$alkoxy; pyridinyl; pyridinyl substituted by one, two or three groups independently selected from $C_{1-6}$ alkyl, $C_{1-6}$alkoxy, hydroxy, halogen and phenyl$C_{1-6}$ alkoxy; pyrimidinyl; pyrimidinyl substituted by one, two or three groups independently selected from $C_{1-6}$alkyl, $C_{1-6}$alkoxy, hydroxy, halogen and phenyl$C_{1-6}$alkoxy; pyrrolyl; pyrrolyl substituted by one, two or three groups independently selected from $C_{1-6}$alkyl, $C_{1-6}$alkoxy, hydroxy, halogen and phenyl$C_{1-6}$ alkoxy; pyrazolyl; pyrazolyl substituted by one, two or three groups independently selected from $C_{1-6}$alkyl, $C_{1-6}$alkoxy, hydroxy, halogen and phenyl$C_{1-6}$alkoxy; thiazolyl; or thiazolyl substituted by one, two or three groups independently selected from $C_{1-6}$alkyl, $C_{1-6}$alkoxy, hydroxy, halogen and phenyl$C_{1-6}$alkoxy; or pharmaceutically acceptable salts, or enantiomers thereof.

Further embodiment of present invention is (ii) a compound of formula I, wherein
$R^1$ is hydrogen;
$R^2$ is hydrogen, halogen or $C_{1-6}$alkoxy;
$R^3$ is $C_{1-6}$alkyl, pyrrolidinyl or $OR^6$;
$R^4$ is $C_{1-6}$alkyl or hydrogen;

R⁵ is hydrogen;

R⁶ is $C_{1-6}$alkyl, halo$C_{1-6}$alkyl, $C_{3-7}$cycloalkyl$C_{1-6}$alkyl, phenyl$C_{1-6}$alkyl, hydroxy$C_{1-6}$alkyl, $C_{1-6}$ alkoxy$C_{1-6}$alkyl, carboxy$C_{1-6}$alkyl, $C_{1-6}$alkylsulfanyl$C_{1-6}$alkyl, $C_{1-6}$alkylsulfonyl$C_{1-6}$alkyl, cyano$C_{1-6}$alkyl, amino$C_{1-6}$alkyl, $C_{1-6}$alkylcarbonylamino$C_{1-6}$alkyl, $C_{1-6}$alkylsulfonylamino$C_{1-6}$ alkyl, $C_{1-6}$alkoxycarbonylamino$C_{1-6}$alkyl, pyrazolyl$C_{1-6}$alkyl, triazolyl$C_{1-6}$alkyl, piperidyl$C_{1-6}$ alkyl, morpholinyl$C_{1-6}$alkyl or 2-oxopyrrolidinyl$C_{1-6}$alkyl;

Ar is phenyl; phenyl substituted by $C_{1-6}$alkyl, $C_{1-6}$alkoxy, hydroxy, halogen or phenyl$C_{1-6}$alkoxy; thienyl; thienyl substituted by $C_{1-6}$alkyl; or benzothiophenyl;

or pharmaceutically acceptable salts, or enantiomers thereof.

Another embodiment of present invention is (iii) a compound of formula I as defined above, or pharmaceutically acceptable salts, or enantiomers thereof, wherein $R^1$ is hydrogen, $R^4$ is hydrogen, $R^5$ is hydrogen, and all remaining substituents have the significances given herein before.

Another embodiment of present invention is (iv) a compound of formula I as defined above, or pharmaceutically acceptable salts, or enantiomers thereof, wherein $R^2$ is $C_{1-6}$alkoxy, and all remaining substituents have the significances given herein before.

A further embodiment of present invention is (v) a compound of formula I as defined above, or pharmaceutically acceptable salts, or enantiomers thereof, wherein $R^2$ is methoxy, and all remaining substituents have the significances given herein before.

Another embodiment of present invention is (vi) a compound of formula I as defined above, or pharmaceutically acceptable salts, or enantiomers thereof, wherein $R^3$ is pyrrolidinyl or $OR^6$, wherein $R^6$ is $C_{1-6}$alkyl, halo$C_{1-6}$alkyl, $C_{3-7}$cycloalkyl$C_{1-6}$alkyl, hydroxy$C_{1-6}$alkyl, $C_{1-6}$alkoxy$C_{1-6}$ alkyl, carboxy$C_{1-6}$alkyl, $C_{1-6}$alkylsulfanyl$C_{1-6}$alkyl, cyano$C_{1-6}$alkyl, amino$C_{1-6}$alkyl, $C_{1-6}$ alkylcarbonylamino$C_{1-6}$ alkyl, $C_{1-6}$alkylsulfonylamino$C_{1-6}$alkyl or $C_{1-6}$alkoxycarbonylamino$C_{1-6}$ alkyl, and all remaining substituents have the significances given herein before.

Further embodiment of present invention is (vii) a compound of formula I as defined above, or pharmaceutically acceptable salts, or enantiomers thereof, wherein $R^3$ is $OR^6$, wherein $R^6$ is methyl, isobutyl, trifluoroethyl, cyclopropylmethyl, cyanopropyl, hydroxypropyl, hydroxyhexyl, hydroxydimethylpropyl, methoxypropyl, carboxypropyl, methyl sulfanylpropyl, aminohexyl, methylcarbonylaminohexyl, methyl sulfonylaminohexyl or methoxycarbonylaminohexyl, and all remaining substituents have the significances given herein before.

Another embodiment of present invention is (viii) a compound of formula I as defined above, or pharmaceutically acceptable salts, or enantiomers thereof, wherein Ar is phenyl, phenyl substituted by $C_{1-6}$alkyl or halogen, thienyl or thienyl substituted by $C_{1-6}$alkyl, and all remaining substituents have the significances given herein before.

Further embodiment of present invention is (ix) a compound of formula I as defined above, or pharmaceutically acceptable salts, or enantiomers thereof, wherein Ar is phenyl; phenyl substituted by methyl, fluoro or chloro; thienyl or thienyl substituted by methyl, and all remaining substituents have the significances given herein before.

Another embodiment of present invention is (x) a compound of formula I, wherein
$R^1$ is hydrogen;
$R^2$ is $C_{1-6}$alkoxy;
$R^3$ is pyrrolidinyl or $OR^6$;
$R^4$ is hydrogen;
$R^5$ is hydrogen;

$R^6$ is $C_{1-6}$alkyl, halo$C_{1-6}$alkyl, $C_{3-7}$cycloalkyl$C_{1-6}$alkyl, hydroxy$C_{1-6}$alkyl, $C_{1-6}$alkoxy$C_{1-6}$alkyl or $C_{1-6}$alkylsulfanyl$C_{1-6}$alkyl;

Ar is phenyl substituted by $C_{1-6}$alkyl, or thienyl;

or pharmaceutically acceptable salts, or enantiomers thereof.

A further embodiment of present invention is (x) a compound of formula I, wherein
$R^1$ is hydrogen;
$R^2$ is methoxy;
$R^3$ is pyrrolidinyl or $OR^6$;
$R^4$ is hydrogen;
$R^5$ is hydrogen;
$R^6$ is isobutyl, trifluoroethyl, cyclopropylmethyl, hydroxydimethylpropyl, methoxypropyl or methyl sulfanylpropyl;

Ar is phenyl substituted by methyl or thienyl;

or pharmaceutically acceptable salts, or enantiomers thereof.

Particular compounds of formula I according to the invention are the following:

10-Methoxy-9-(3-methoxypropoxy)-2-oxo-6-phenyl-6,7-dihydrobenzo[a]quinolizine-3-carboxylic acid;

10-Methoxy-9-(3-methoxypropoxy)-2-oxo-6-(3-thienyl)-6,7-dihydrobenzo[a]quinolizine-3-carboxylic acid;

10-Methoxy-9-(3-methoxypropoxy)-2-oxo-6-(2-thienyl)-6,7-dihydrobenzo[a]quinolizine-3-carboxylic acid;

6-(4-Hydroxyphenyl)-10-methoxy-9-(3-methoxypropoxy)-2-oxo-6,7-dihydrobenzo[a]quinolizine-3-carboxylic acid;

10-Methoxy-6-(4-methoxyphenyl)-9-(3-methoxypropoxy)-2-oxo-6,7-dihydrobenzo[a]quinolizine-3-carboxylic acid;

6-(4-Benzyloxyphenyl)-10-methoxy-9-(3-methoxypropoxy)-2-oxo-6,7-dihydrobenzo[a]quinolizine-3-carboxylic acid;

10-Methoxy-9-(3-methoxypropoxy)-6-(4-methyl-2-thienyl)-2-oxo-6,7-dihydrobenzo[a]quinolizine-3-carboxylic acid;

6-(3-Chlorophenyl)-10-methoxy-9-(3-methoxypropoxy)-2-oxo-6,7-dihydrobenzo[a]quinolizine-3-carboxylic acid;

6-(4-Fluorophenyl)-10-methoxy-9-(3-methoxypropoxy)-2-oxo-6,7-dihydrobenzo[a]quinolizine-3-carboxylic acid;

10-Methoxy-9-(3-methoxypropoxy)-6-(o-tolyl)-2-oxo-6,7-dihydrobenzo[a]quinolizine-3-carboxylic acid;

9-Methoxy-8-methyl-2-oxo-6-(2-thienyl)-6,7-dihydrobenzo[a]quinolizine-3-carboxylic acid;

9-Benzyloxy-10-methoxy-2-oxo-6-(2-thienyl)-6,7-dihydrobenzo[a]quinolizine-3-carboxylic acid;

9,10-Dimethoxy-2-oxo-6-(2-thienyl)-6,7-dihydrobenzo[a]quinolizine-3-carboxylic acid;

9-Isobutoxy-10-methoxy-2-oxo-6-(2-thienyl)-6,7-dihydrobenzo[a]quinolizine-3-carboxylic acid;

9-(Cyclopropylmethoxy)-10-methoxy-2-oxo-6-(2-thienyl)-6,7-dihydrobenzo[a]quinolizine-3-carboxylic acid;

10-Methoxy-2-oxo-9-(3-pyrazol-1-ylpropoxy)-6-(2-thienyl)-6,7-dihydrobenzo[a]quinolizine-3-carboxylic acid;

9-(3-Hydroxypropoxy)-10-methoxy-2-oxo-6-(2-thienyl)-6,7-dihydrobenzo[a]quinolizine-3-carboxylic acid;

10-Methoxy-2-oxo-9-[3-(1-piperidyl)propoxy]-6-(2-thienyl)-6,7-dihydrobenzo[a]quinolizine-3-carboxylic acid formate;

9-(3-Cyanopropoxy)-10-methoxy-2-oxo-6-(2-thienyl)-6,7-dihydrobenzo[a]quinolizine-3-carboxylic acid;

10-Methoxy-2-oxo-9-[2-(2-oxopyrrolidin-1-yl)ethoxy]-6-(2-thienyl)-6,7-dihydrobenzo[a]quinolizine-3-carboxylic acid;

9-[6-(tert-Butoxycarbonylamino)hexoxy]-10-methoxy-2-oxo-6-(2-thienyl)-6,7-dihydrobenzo[a]quinolizine-3-carboxylic acid;

9-(6-Aminohexoxy)-10-methoxy-2-oxo-6-(2-thienyl)-6,7-dihydrobenzo[a]quinolizine-3-carboxylic acid formate;
9-(6-Acetamidohexoxy)-10-methoxy-2-oxo-6-(2-thienyl)-6,7-dihydrobenzo[a]quinolizine-3-carboxylic acid;
9-[6-(Methanesulfonamido)hexoxy]-10-methoxy-2-oxo-6-(2-thienyl)-6,7-dihydrobenzo[a]quinolizine-3-carboxylic acid;
9-(6-Hydroxyhexoxy)-10-methoxy-2-oxo-6-(2-thienyl)-6,7-dihydrobenzo[a]quinolizine-3-carboxylic acid;
9-(3-Hydroxy-2,2-dimethyl-propoxy)-10-methoxy-2-oxo-6-(2-thienyl)-6,7-dihydrobenzo[a]quinolizine-3-carboxylic acid;
10-Methoxy-2-oxo-6-(2-thienyl)-9-(2,2,2-trifluoroethoxy)-6,7-dihydrobenzo[a]quinolizine-3-carboxylic acid;
10-Methoxy-9-(3-morpholinopropoxy)-2-oxo-6-(2-thienyl)-6,7-dihydrobenzo[a]quinolizine-3-carboxylate;
10-Methoxy-2-oxo-6-(2-thienyl)-9-[3-(1,2,4-triazol-1-yl)propoxy]-6,7-dihydrobenzo[a]quinolizine-3-carboxylic acid;
9-(3-Carboxypropoxy)-10-methoxy-2-oxo-6-(2-thienyl)-6,7-dihydrobenzo[a]quinolizine-3-carboxylic acid;
10-Methoxy-9-(3-methylsulfanylpropoxy)-2-oxo-6-(2-thienyl)-6,7-dihydrobenzo[a]quinolizine-3-carboxylic acid;
10-Methoxy-9-(3-methylsulfonylpropoxy)-2-oxo-6-(2-thienyl)-6,7-dihydrobenzo[a]quinolizine-3-carboxylic acid;
10-Methoxy-9-methyl-2-oxo-6-(2-thienyl)-6,7-dihydrobenzo[a]quinolizine-3-carboxylic acid;
9-Ethyl-10-methoxy-2-oxo-6-(2-thienyl)-6,7-dihydrobenzo[a]quinolizine-3-carboxylic acid;
10-Methoxy-2-oxo-9-propyl-6-(2-thienyl)-6,7-dihydrobenzo[a]quinolizine-3-carboxylic acid;
10-Methoxy-2-oxo-9-pyrrolidin-1-yl-6-(2-thienyl)-6,7-dihydrobenzo[a]quinolizine-3-carboxylic acid;
6-(Benzothiophen-2-yl)-10-chloro-9-(3-methoxypropoxy)-2-oxo-6,7-dihydrobenzo[a]quinolizine-3-carboxylic acid;
or pharmaceutically acceptable salts, or enantiomers thereof.

More particularly, the invention relates to the following compounds of formula I:
10-Methoxy-9-(3-methoxypropoxy)-2-oxo-6-(3-thienyl)-6,7-dihydrobenzo[a]quinolizine-3-carboxylic acid;
10-Methoxy-9-(3-methoxypropoxy)-2-oxo-6-(2-thienyl)-6,7-dihydrobenzo[a]quinolizine-3-carboxylic acid;
10-Methoxy-9-(3-methoxypropoxy)-6-(o-tolyl)-2-oxo-6,7-dihydrobenzo[a]quinolizine-3-carboxylic acid;
9-Isobutoxy-10-methoxy-2-oxo-6-(2-thienyl)-6,7-dihydrobenzo[a]quinolizine-3-carboxylic acid;
9-(Cyclopropylmethoxy)-10-methoxy-2-oxo-6-(2-thienyl)-6,7-dihydrobenzo[a]quinolizine-3-carboxylic acid;
9-(3-Hydroxy-2,2-dimethyl-propoxy)-10-methoxy-2-oxo-6-(2-thienyl)-6,7-dihydrobenzo[a]quinolizine-3-carboxylic acid;
10-Methoxy-2-oxo-6-(2-thienyl)-9-(2,2,2-trifluoroethoxy)-6,7-dihydrobenzo[a]quinolizine-3-carboxylic acid;
10-Methoxy-9-(3-methylsulfanylpropoxy)-2-oxo-6-(2-thienyl)-6,7-dihydrobenzo[a]quinolizine-3-carboxylic acid;
10-Methoxy-2-oxo-9-pyrrolidin-1-yl-6-(2-thienyl)-6,7-dihydrobenzo[a]quinolizine-3-carboxylic acid;
or pharmaceutically acceptable salts, or enantiomers thereof.

Synthesis

The compounds of the present invention can be prepared by any conventional means. Suitable processes for synthesizing these compounds as well as their starting materials are provided in the schemes below and in the examples. All substituents, in particular, $R^1$ to $R^5$ and Ar are as defined above unless otherwise indicated. Furthermore, and unless explicitly otherwise stated, all reactions, reaction conditions, abbreviations and symbols have the meanings well known to a person of ordinary skill in organic chemistry.

General Synthetic Route for Compounds I (Scheme 1)

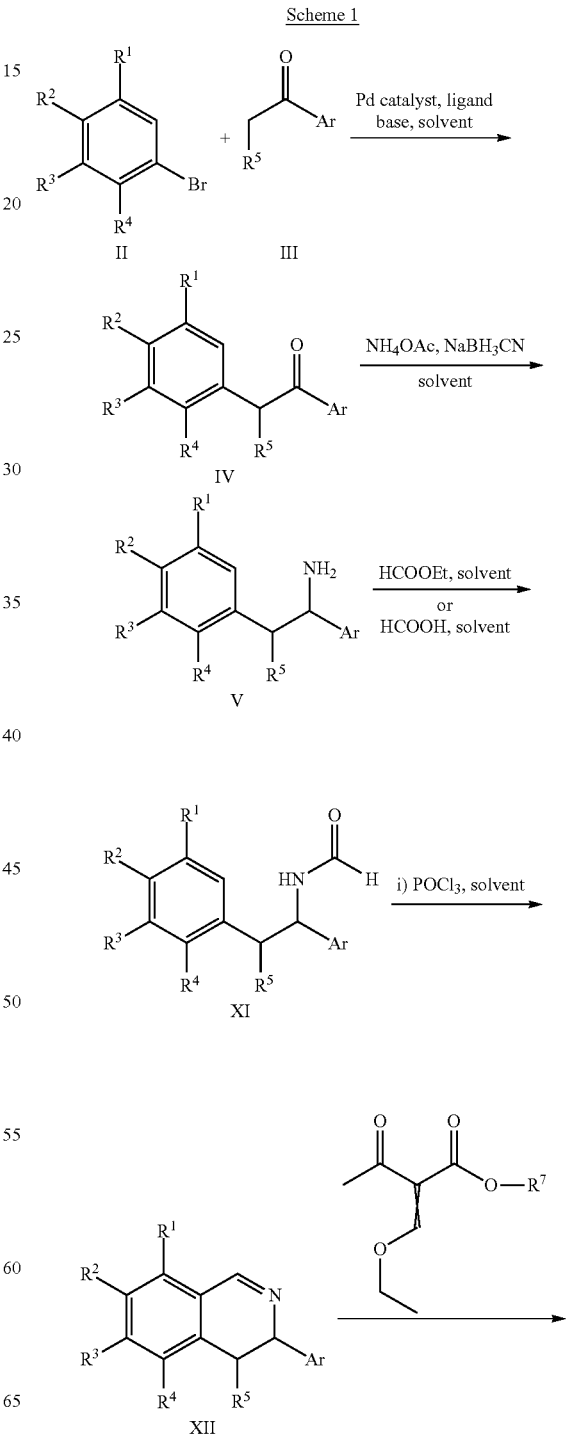

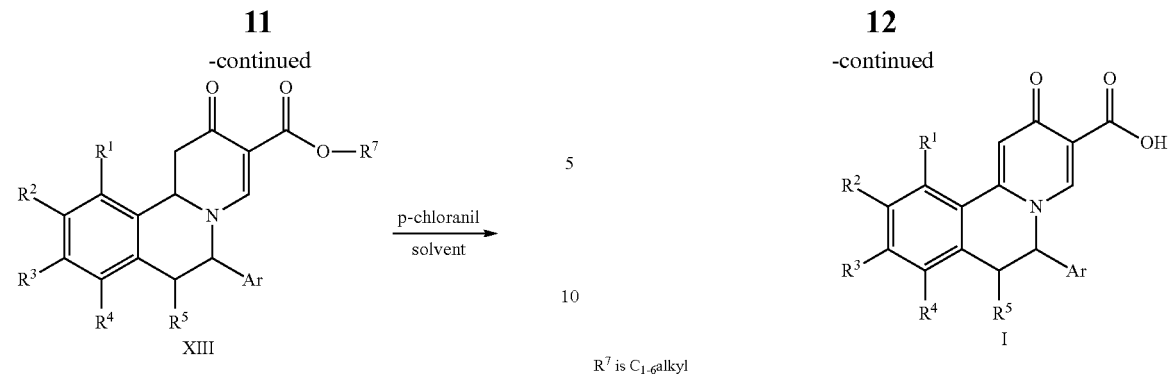

R⁷ is C₁₋₆alkyl

The compound of formula I can be prepared according to Scheme 1. Coupling reaction of bromo-benzene II with ketone III affords Compound IV. The reaction can be carried out in the presence of a Pd catalyst such as $Pd_2(dba)_3$, $Pd(PPh_3)_4$ or $PdCl_2(PPh_3)_2$, a ligand such as Xantphos, and a suitable base such as t-BuONa, $Na_2CO_3$ or $Cs_2CO_3$, in a suitable solvent such as THF, toluene or 1,4-dioxane at a temperature between room temperature and 130° C. Reductive amination of Compound IV affords Compound V. Compound V is heated with ethyl formate or formic acid in a solvent such as ethanol or dioxane to afford Compound XI. Compound XI is treated with $POCl_3$ in a suitable solvent such as acetonitrile or DCM at a temperature between room temperature and 100° C. to give Compound XII. Compound XII reacts with $C_{1-6}$alkyl 2-(ethoxymethylene)-3-oxo-butanoate in a solvent such as ethanol to give Compound XIII. Compound XIV is obtained by dehydrogenation of compound XIII by using p-chloranil. Hydrolyzation of Compound XIV with a base such as lithium hydroxide or sodium hydroxide in a suitable solvent such as $THF/H_2O$, $EtOH/H_2O$ or $MeOH/H_2O$ affords the compound of formula I.

General Synthetic Route for Compounds I-1
(Scheme 2)

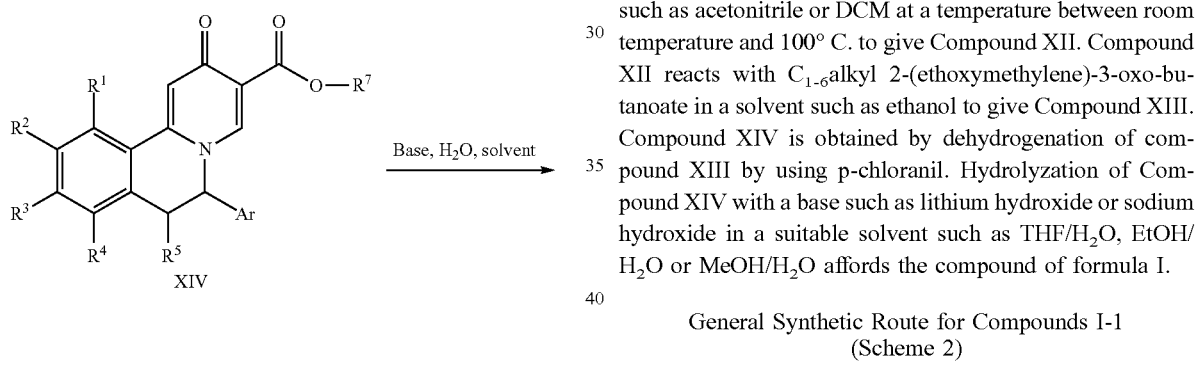

Scheme 2

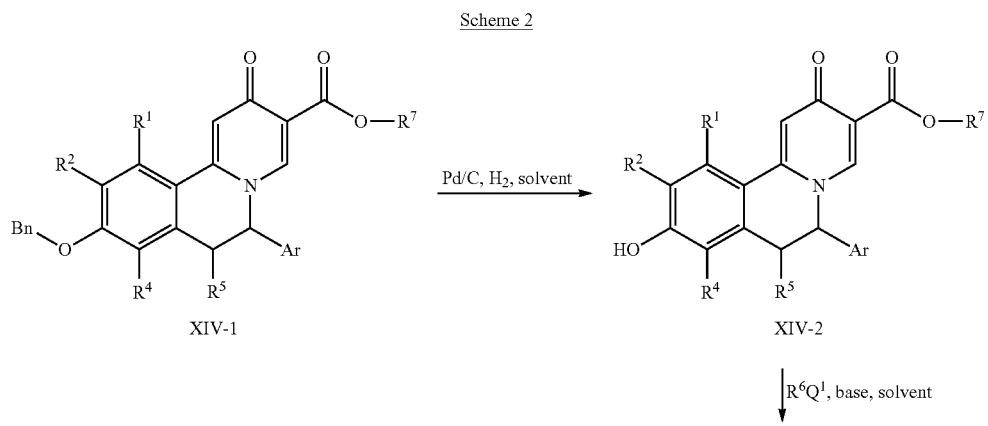

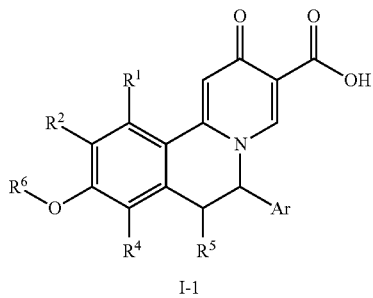

I-1

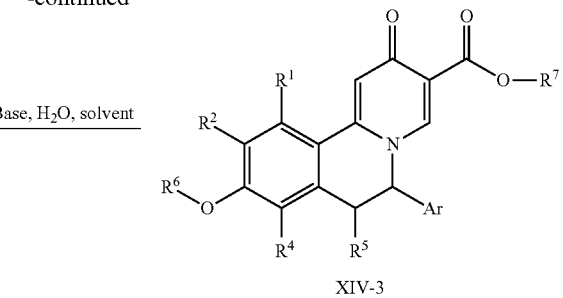

XIV-3

$Q^1$ is halogen, —O—S(O)$_2$CH$_3$ or —O—S(O)$_2$—(4-CH$_3$—Ph).
$R^7$ is C$_{1-6}$alkyl The compound of formula I-1 can be prepared according to Scheme 2. Debenzylation of Compound XIV-1 by hydrogenation is carried out in the presence of Pd/C in a solvent such as ethanol, THF, methanol to afford Compound XIV-2. Then Compound XIV-2 reacts with halides, mesylates or tosylates in the presence of a base such as K$_2$CO$_3$ in a solvent such as acetone or DMF to give XIV-3. Hydrolyzation of Compound XIV with a base such as lithium hydroxide or sodium hydroxide in a suitable solvent such as THF/H$_2$O, EtOH/H$_2$O or MeOH/H$_2$O affords the compound of formula I-1.

This invention also relates to a process for the preparation of a compound of formula I comprising
(a) hydrolysis of a compound of formula (A)

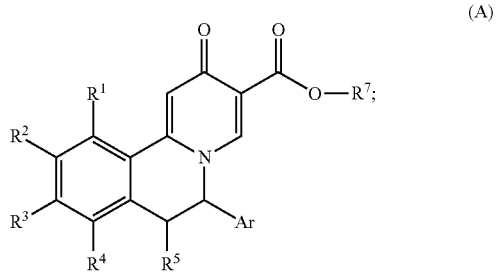

(A)

or
(b) hydrolysis of a compound of formula (B)

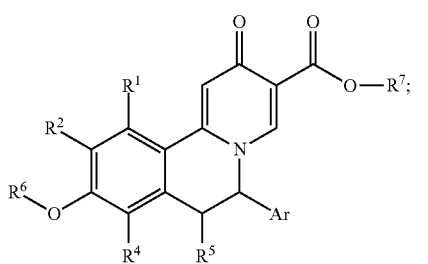

(B)

wherein $R^1$ to $R^7$ and Ar are defined above unless otherwise indicated.

In step (a) and step (b) a base such as lithium hydroxide or sodium hydroxide can be for example used.

A compound of formula I when manufactured according to the above process is also an object of the invention.

Pharmaceutical Compositions and Administration

The invention also relates to a compound of formula I for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit HBsAg. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.01 to 100 mg/kg of patient body weight per day, with the typical initial range of compound used being 0.3 to 15 mg/kg/day. In another embodiment, oral unit dosage forms, such as tablets and capsules, preferably contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 to 1000 mg of the compound of the invention compounded with about 0 to 2000 mg anhydrous lactose, about 0 to 2000 mg sodium croscarmellose, about 0 to 2000 mg polyvinylpyrrolidone (PVP) K30, and about 0 to 2000 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 0.1 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

The following example A and B illustrate typical compositions of the present invention, but serve merely as representative thereof.

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Indications and Methods of Treatment

The compounds of the invention can inhibit HBsAg production or secretion and inhibit HBV gene expression. Accordingly, the compounds of the invention are useful for the treatment or prophylaxis of HBV infection.

The invention relates to the use of a compound of formula I for the inhibition of HBsAg production or secretion.

The invention relates to the use of a compound of formula I for the inhibition of HBV DNA production.

The invention relates to the use of a compound of formula I for the inhibition of HBV gene expression.

The invention relates to the use of a compound of formula I for the treatment or prophylaxis of HBV infection.

The use of a compound of formula I for the preparation of medicaments useful in the treatment or prophylaxis diseases that are related to HBV infection is an object of the invention.

The invention relates in particular to the use of a compound of formula I for the preparation of a medicament for the treatment or prophylaxis of HBV infection.

Another embodiment includes a method for the treatment or prophylaxis of HBV infection, which method comprises administering an effective amount of a compound of Formula I, a stereoisomer, tautomer, prodrug, conjugates or pharmaceutically acceptable salt thereof.

Combination Therapy

The compounds of the invention can be combined with other anti HBV agents such as interferon alpha-2b, interferon alpha-2a, and interferon alphacon-1 (pegylated and unpegylated), ribavirin, lamivudine (3TC), entecavir, tenofovir, telbivudine (LdT), adefovir, or other emerging anti HBV agents such as HBV RNA replication inhibitor, HBsAg secretion inhibitors, HBV capsid inhibitors, antisense oligomer, siRNA, HBV therapeutic vaccine, HBV prophylactic vaccine, HBV antibody therapy (monoclonal or polyclonal) and TLR 2, 3, 7, 8 and 9 agonists for the treatment or prophylaxis of HBV.

EXAMPLES

The invention will be more fully understood by reference to the following examples. They should not, however, be construed as limiting the scope of the invention.

Abbreviations used herein are as follows:
μL: microliter
μm: micrometer
μM: micromoles per liter
Ar: argon
DIPEA: N,N-diisopropylethylamine
DME: 1,2-dimethoxyethane
DMF: dimethylformamide
DMSO-d6: deuterated dimethylsulfoxide
EtOAc: ethyl acetate
h or hr: hour
hrs: hours
$IC_{50}$: the half maximal inhibitory concentration
HCMV: human cytomegalovirus
HIV: human immunodeficiency
HSV: herpes simplex virus
HPV: human papillomavirus
HPLC: high performance liquid chromatography
LC/MS: Liquid chromatography/mass spectrometry
m-CPBA: m-chloroperoxybenzoic acid
MeOH: methanol
METHANOL-$d_4$: perdeuteromethanol
M: molarity
mg: milligram
MHz: megahertz
min: minute
mL: milliliter
mM: millimoles per liter
mm: millimeter
mmol: millimole
MS (ESI): mass spectroscopy (electron spray ionization)
NMR: nuclear magnetic resonance
$N_2$: nitrogen
rt: room temperature
Pd/C: palladium on activated carbon
Pd(PPh$_3$)$_4$: tetrakis(triphenylphosphine)palladium
Pd(dppf)Cl$_2$: [1,1'-bis(diphenylphosphino)ferrocene]dichloropalladium(II)
PE or Pet: petroleum ether
prep-HPLC: preparative high performance liquid chromatography
TFA: trifluoroacetic acid
TLC: thin layer chromatography
δ: chemical shift
Xantphos: 9,9-dimethyl-4,5-bis(diphenylphosphino)xanthene
Pd$_2$(dba)$_3$: tris(dibenzylideneacetone)dipalladium(0)
t-BuONa: sodium t-butoxide General Experimental Conditions Intermediates and final compounds were purified by flash chromatography using one of the following instruments: i) Biotage SPI system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 μm, OBD™ 30) 100 mm) column or SunFire™ Perp $C_1$ (5 μm, OBD™ 30×100 mm) column.

LC/MS spectra were obtained using an Acquity Ultra Performance LC-3100 Mass Detector or Acquity Ultra Performance LC-SQ Detector. Standard LC/MS conditions were as follows (running time 3 minutes):

Acidic condition: A: 0.1% formic acid in $H_2O$; B: 0.1% formic acid in acetonitrile;
Basic condition: A: 0.05% $NH_3$—$H_2O$ in $H_2O$; B: acetonitrile;
Neutral condition: A: $H_2O$; B: acetonitrile.

Mass spectra (MS): generally only ions which indicate the parent mass are reported, and unless otherwise stated the mass ion quoted is the positive mass ion $(M+H)^+$.

The microwave assisted reactions were carried out in a Biotage Initiator Sixty or CEM Discover.

NMR Spectra were obtained using Bruker Avance 400 MHz.

All reactions involving air-sensitive reagents were performed under an argon atmosphere. Reagents were used as received from commercial suppliers without further purification unless otherwise noted.

Preparative Examples

Example 1: 10-methoxy-9-(3-methoxypropoxy)-2-oxo-6-phenyl-6,7-dihydrobenzo[a]quinolizin-3-carboxylic Acid

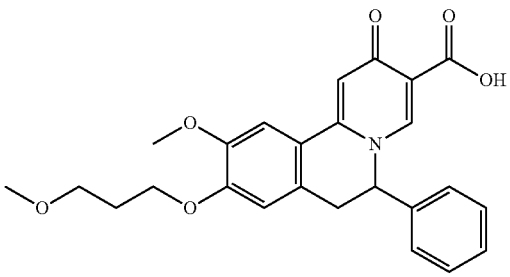 [SMILES: COCCCOc1cc2c(cc1OC)-c1cc(=O)c(C(=O)O)cn1C(c1ccccc1)C2]

Step 1: Preparation of 4-bromo-1-methoxy-2-(3-methoxypropoxy)benzene

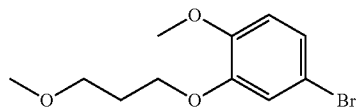

To a solution of 5-bromo-2-methoxy-phenol (10.0 g, 49.5 mmol) in MeCN (100 mL) was added $Cs_2CO_3$ (48.1 g, 148 mmol) and 1-bromo-3-methoxy-propane (11.3 g, 74 mmol). The mixture was refluxed for 16 hrs, and then filtered. The filtrate was concentrated under reduced pressure, and the residue was purified by trituration with PE to give 4-bromo-1-methoxy-2-(3-methoxypropoxy)benzene (10.5 g) as a white solid.

Step 2: Preparation of 2-[4-methoxy-3-(3-methoxypropoxy)phenyl]-1-phenyl-ethanone

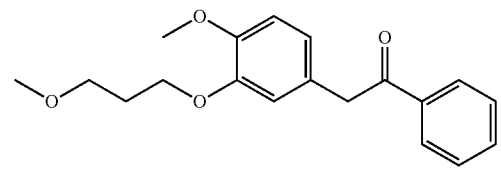 [SMILES: COCCCOc1cc(CC(=O)c2ccccc2)ccc1OC]

A mixture of 4-bromo-1-methoxy-2-(3-methoxypropoxy)benzene (10.0 g, 36.4 mmol), 1-phenylethanone (5.7 g, 47 mmol), t-BuONa (5.24 g, 55 mmol), Xantphos (840 mg, 1.5 mmol) and Pd$_2$(dba)$_3$ (660 mg, 0.73 mmol) in THF (100 mL) was heated with stirring at 80° C. for 5 hrs under nitrogen atmosphere. The mixture was cooled to rt and filtered. The filtrate was concentrated under reduced pressure. The residue was purified by the flash column chromatography to afford 2-[4-methoxy-3-(3-methoxypropoxy)phenyl]-1-phenyl-ethanone (9.5 g) as a yellow solid.

Step 3: Preparation of 2-[4-methoxy-3-(3-methoxypropoxy)phenyl]-1-phenyl-ethanamine

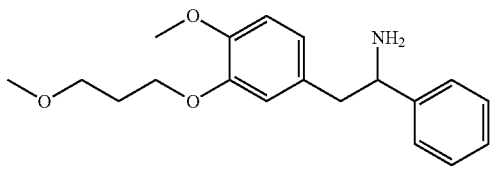 [SMILES: COCCCOc1cc(CC(N)c2ccccc2)ccc1OC]

To a solution of 2-[4-methoxy-3-(3-methoxypropoxy)phenyl]-1-phenyl-ethanone (9.5 g, 30.2 mmol) in MeOH (100 mL) was added NH$_4$OAc (17.2 g, 223 mmol) at 18° C. After being stirred for 1 hr, the resulting mixture was cooled to 0° C. Then to the cooled mixture was added NaBH$_3$CN (4 g, 63.6 mmol) at 0° C. The resulting mixture was then heated with stirring at 50° C. for 12 hrs. The resulting reaction mixture was concentrated under reduced pressure. The residue was diluted with H$_2$O (200 mL) and extracted with DCM (300 mL). The organic layer was washed with brine (200 mL), dried over anhydrous Na$_2$SO$_4$ and concentrated under reduced pressure to afford 2-[4-methoxy-3-(3-methoxypropoxy)phenyl]-1-phenyl-ethanamine (13.4 g) as a yellow oil, which was used directly in the next step without further purification.

Step 4: Preparation of N-[2-[4-methoxy-3-(3-methoxypropoxy)phenyl]-1-phenyl-ethyl]formamide

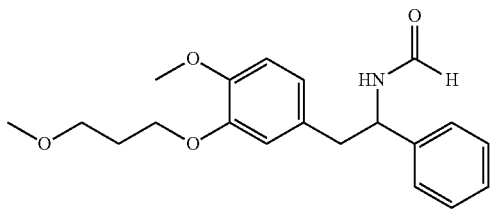 [SMILES: COCCCOc1cc(CC(NC=O)c2ccccc2)ccc1OC]

To a solution of 2-[4-methoxy-3-(3-methoxypropoxy)phenyl]-1-phenyl-ethanamine (13.0 g, 41.3 mmol) in dioxane (150 mL) was added formic acid (13.3 g, 289 mmol). The mixture was heated with stirring at 120° C. for 12 hrs. After being cooled to rt, the resulting mixture was concentrated under reduced pressure. The residue was diluted with EtOAc (300 mL). The organic mixture was washed with H$_2$O (200 mL) and brine (200 mL, 2 times), dried over anhydrous Na$_2$SO$_4$ and concentrated under reduced pressure. The residue was purified by column chromatography to give N-[2-[4-methoxy-3-(3-methoxypropoxy)phenyl]-1-phenyl-ethyl]formamide (2.2 g, yield: 16%) as a yellow solid.

Step 5: Preparation of 7-methoxy-6-(3-methoxypropoxy)-3-phenyl-3,4-dihydroisoquinoline

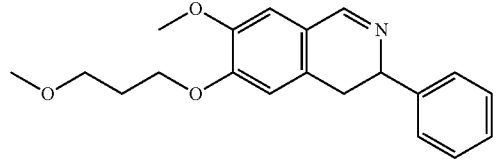 [SMILES: COCCCOc1cc2c(cc1OC)C=NC(c1ccccc1)C2]

To a solution of N-[2-[4-methoxy-3-(3-methoxypropoxy)phenyl]-1-phenyl-ethyl]formamide (2.0 g, 5.8 mmol) in DCM (20 mL) was added POCl$_3$ (2.29 g, 14.9 mmol). After being heated with stirring at 40° C. for 12 hrs, the resulting mixture was basified by ammonia water and extracted with DCM (200 mL). The organic layer was washed with brine, dried over anhydrous Na$_2$SO$_4$ and concentrated under reduced pressure. The residue was purified by column chromatography to give 7-methoxy-6-(3-methoxypropoxy)-3-phenyl-3,4-dihydroisoquinoline (500 mg) as a green solid.

Step 6: Preparation of ethyl 10-methoxy-9-(3-methoxypropoxy)-2-oxo-6-phenyl-1,6,7,11b-tetrahydrobenzo[a]quinolizine-3-carboxylate

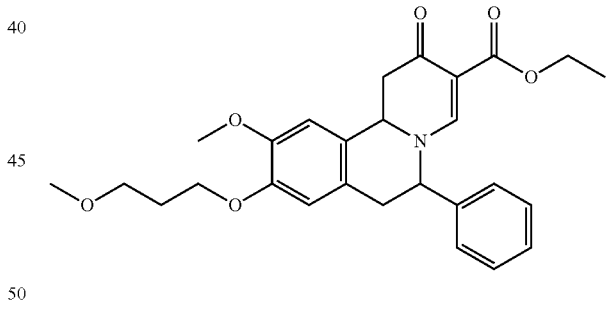

A solution of 7-methoxy-6-(3-methoxypropoxy)-3-phenyl-3,4-dihydroisoquinoline (500 mg, 1.54 mmol) and ethyl 2-(ethoxymethylene)-3-oxo-butanoate (688 mg, 3.69 mmol) in EtOH (5 mL) was heated with stirring at 100° C. for 48 hrs. After being cooled to rt, the resulting mixture was concentrated under reduced pressure to give crude ethyl 10-methoxy-9-(3-methoxypropoxy)-2-oxo-6-phenyl-1,6,7,11b-tetrahydrobenzo[a]quinolizine-3-carboxylate, which was used directly in the next step without further purification.

Step 7: Preparation of ethyl 10-methoxy-9-(3-methoxypropoxy)-2-oxo-6-phenyl-6,7-dihydrobenzo[a]quinolizine-3-carboxylate

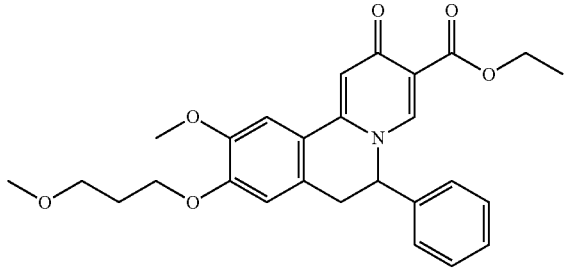 [SMILES: CCOC(=O)c1cn2c(cc1=O)-c1cc(OC)c(OCCCOC)cc1CC2c1ccccc1]

To a solution of ethyl 10-methoxy-9-(3-methoxypropoxy)-2-oxo-6-phenyl-1,6,7,11b-tetrahydrobenzo[a]quinolizine-3-carboxylate (916 mg, 1.97 mmol) in DME (10 mL) was added p-chloranil (486 mg, 1.97 mmol). The resulting mixture was heated with stirring at 70° C. for 3 hrs under nitrogen atmosphere. Then the mixture was filtered. The filtrate was concentrated under reduced pressure. The residue was dissolved in DCM. The resulting solution was washed with NaHCO₃ aqueous solution and brine, dried over anhydrous Na₂SO₄ and concentrated under reduced pressure to afford crude ethyl 10-methoxy-9-(3-methoxypropoxy)-2-oxo-6-phenyl-6,7-dihydrobenzo[a]quinolizine-3-carboxylate (1.2 g) as a yellow solid, which was used directly in the next step without further purification.

Step 8: Preparation of 10-methoxy-9-(3-methoxypropoxy)-2-oxo-6-phenyl-6,7-dihydrobenzo[a]quinolizine-3-carboxylic Acid

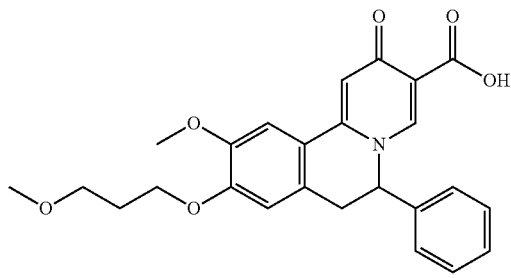 [SMILES: COCCCOc1cc2c(cc1OC)-c1cc(=O)c(C(=O)O)cn1C(c1ccccc1)C2]

To a solution of ethyl 10-methoxy-9-(3-methoxypropoxy)-2-oxo-6-phenyl-6,7-dihydrobenzo[a]quinolizine-3-carboxylate (1.02 g, 2.2 mmol) in MeOH (10 mL) was added 2 M NaOH aqueous solution (2.2 mL). The mixture was stirred at 18° C. for 16 hrs, and then concentrated under reduced pressure. The residue was acidified with 2 M hydrochloric acid to pH=3. Then the resulting aqueous mixture was extracted with DCM. The organic layer was dried over anhydrous Na₂SO₄ and concentrated under reduced pressure. The residue was purified by prep-HPLC to afford 10-methoxy-9-(3-methoxypropoxy)-2-oxo-6-phenyl-6,7-dihydrobenzo[a]quinolizine-3-carboxylic acid (5 mg) as a pale yellow solid. ¹H NMR (400 MHz, DMSO-d6): δ 1.87-1.98 (m, 2H) 3.21 (s, 3H) 3.42 (t, 3H) 3.66 (dd, 1H) 3.85 (s, 3H) 4.00 (t, 2H) 6.08 (br. s., 1H) 6.93 (s, 1H) 6.98 (d, 2H) 7.19-7.33 (m, 3H) 7.51 (s, 1H) 7.58 (s, 1H) 8.82 (s, 1H). MS obsd. (ESI⁺) [(M+H)⁺]: 435.

Example 2: 10-methoxy-9-(3-methoxypropoxy)-2-oxo-6-(3-thienyl)-6,7-dihydrobenzo[a]quinolizine-3-carboxylic Acid

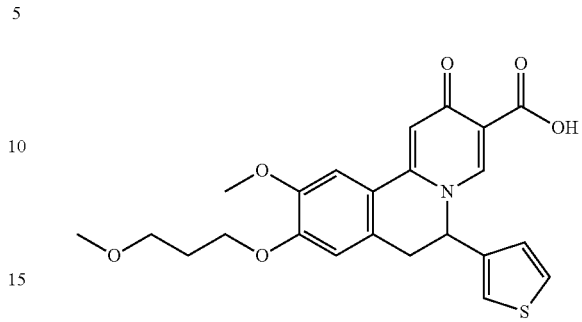

Step 1: Preparation of 2-[4-methoxy-3-(3-methoxypropoxy)phenyl]-1-(3-thienyl)ethanone

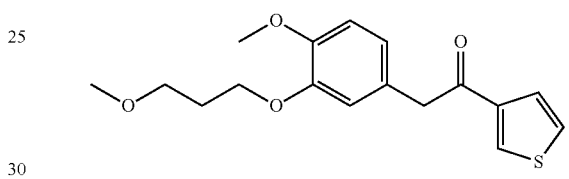

A mixture of 4-bromo-1-methoxy-2-(3-methoxypropoxy)benzene (16.5 g, 60 mmol), 1-(3-thienyl)ethanone (9.84 g, 78 mmol), t-BuONa (8.64 g, 90 mmol), Xantphos (1.39 g, 2.4 mmol) and Pd₂(dba)₃ (1.1 g, 1.2 mmol) in THF (200 mL) was heated at 100° C. for 1 hr. After being cooled to rt, the mixture was filtered. The filtrate was concentrated under reduced pressure and the residue was purified by the flash column chromatography to afford 2-[4-methoxy-3-(3-methoxypropoxy)phenyl]-1-(3-thienyl)ethanone (6.8 g) as a brown oil.

Step 2: Preparation of 2-[4-methoxy-3-(3-methoxypropoxy)phenyl]-1-(3-thienyl)ethanamine

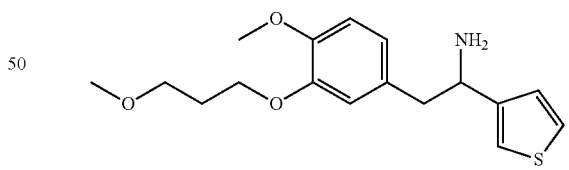

To a solution of 2-[4-methoxy-3-(3-methoxypropoxy)phenyl]-1-(3-thienyl)ethanone (6.8 g, 21.2 mmol) in MeOH (80 mL) was added NH₄OAc (16.4 g, 212 mmol) at rt. After being stirred for 1 hr, the resulting mixture was cooled to 0° C. Then to the cooled mixture was added NaBH₃CN (2.67 g, 42.5 mmol) at 0° C. Then the mixture was heated and stirred at 50° C. for 12 hrs. The mixture was concentrated under reduced pressure. The residue was diluted with H₂O (200 mL). The aqueous mixture was extracted with DCM (300 mL). The organic layer was washed with brine (200 mL), dried over anhydrous Na₂SO₄ and concentrated under reduced pressure to afford crude 2-[4-methoxy-3-(3- methoxypropoxy)phenyl]-1-(3-thienyl)ethanamine (6.82 g) as a yellow oil, which was used directly in the next step without further purification.

Step 3: Preparation of N-[2-[4-methoxy-3-(3-methoxypropoxy)phenyl]-1-(3-thienyl)ethyl]formamide

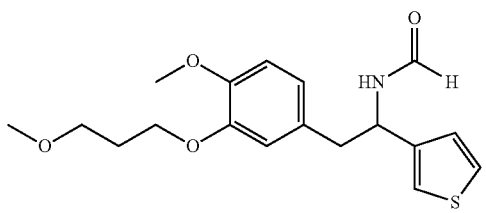 [SMILES: COCCCOc1cc(CC(NC=O)c2ccsc2)ccc1OC]

To a solution of crude 2-[4-methoxy-3-(3-methoxypropoxy)phenyl]-1-(3-thienyl)ethanamine (6.82 g, 21.2 mmol) in dioxane (80 mL) was added formic acid (9.77 g, 212 mmol). Then the mixture was heated at 120° C. for 12 hrs. After being cooled to rt, the mixture was concentrated under reduced pressure. The residue was diluted with EtOAc (300 mL). The organic mixture was washed with H₂O (200 mL) and brine (200 mL, 2 times), dried over anhydrous Na₂SO₄ and concentrated under reduced pressure. The residue was purified by column chromatography to give N-[2-[4-methoxy-3-(3-methoxypropoxy)phenyl]-1-(3-thienyl)ethyl]formamide (5.0 g) as a yellow solid.

Step 4: Preparation of 7-methoxy-6-(3-methoxypropoxy)-3-(3-thienyl)-3,4-dihydroisoquinoline

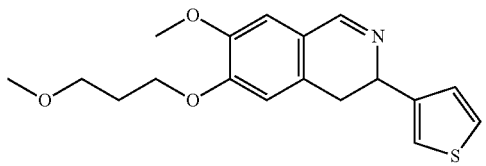 [SMILES: COCCCOc1cc2c(cc1OC)C=NC(c1ccsc1)C2]

To a solution of N-[2-[4-methoxy-3-(3-methoxypropoxy)phenyl]-1-(3-thienyl)ethyl]formamide (5.0 g, 14.3 mmol) in DCM (50 mL) was added POCl₃ (4.51 g, 29.3 mmol). The mixture was heated at 40° C. for 12 hrs and then basified with ammonia water. The resulting mixture was extracted with DCM (200 mL). The organic layer was dried over anhydrous Na₂SO₄ and concentrated under reduced pressure. The residue was purified by column chromatography to give 7-methoxy-6-(3-methoxypropoxy)-3-(3-thienyl)-3,4-dihydroisoquinoline (3.0 g) as a yellow solid.

Step 5: Preparation of ethyl 10-methoxy-9-(3-methoxypropoxy)-2-oxo-6-(3-thienyl)-1,6,7,11b-tetrahydrobenzo[a]quinolizine-3-carboxylate

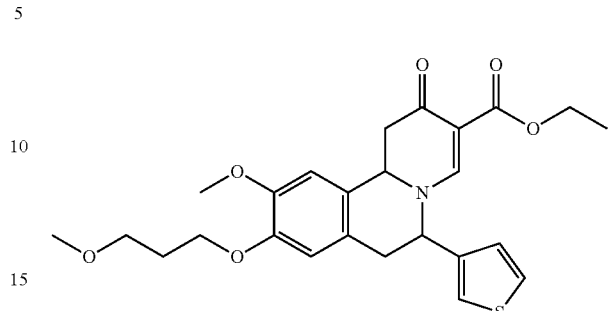

A mixture of 7-methoxy-6-(3-methoxypropoxy)-3-(3-thienyl)-3,4-dihydroisoquinoline (610 mg, 1.84 mmol) and ethyl 2-(ethoxymethylene)-3-oxo-butanoate (1.03 g, 5.52 mmol) in EtOH (10 mL) was heated at 100° C. for 48 hrs. After being cooled to rt, the mixture was concentrated under reduced pressure to give crude ethyl 10-methoxy-9-(3-methoxypropoxy)-2-oxo-6-(3-thienyl)-1,6,7,11b-tetrahydrobenzo[a]quinolizine-3-carboxylate, which was used directly in the next step without further purification.

Step 6: Preparation of ethyl 10-methoxy-9-(3-methoxypropoxy)-2-oxo-6-(3-thienyl)-6,7-dihydrobenzo[a]quinolizine-3-carboxylate

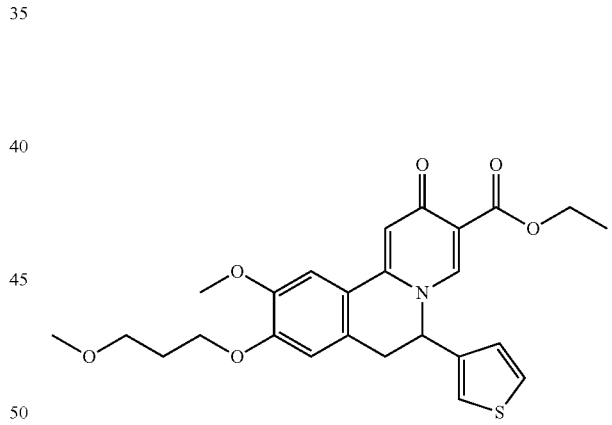

To a solution of ethyl 10-methoxy-9-(3-methoxypropoxy)-2-oxo-6-(3-thienyl)-1,6,7,11b-tetrahydrobenzo[a]quinolizine-3-carboxylate (800 mg, 1.70 mmol) in DME (10 mL) was added p-chloranil (375 mg, 1.53 mmol). The mixture was heated at 70° C. for 3 hrs under nitrogen atmosphere. Then the mixture was filtered. The filter cake was dried under reduced pressure to afford ethyl 10-methoxy-9-(3-methoxypropoxy)-2-oxo-6-(3-thienyl)-6,7-dihydrobenzo[a]quinolizine-3-carboxylate (250 mg) as a yellow solid.

Step 7: Preparation of 10-methoxy-9-(3-methoxy-propoxy)-2-oxo-6-(3-thienyl)-6,7-dihydrobenzo[a]quinolizine-3-carboxylic Acid

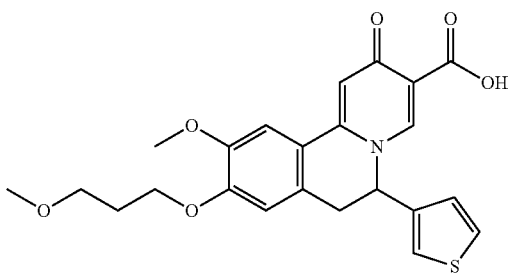 [SMILES: COCCCOc1cc2c(cc1OC)-c1cc(=O)c(C(=O)O)cn1C(c1ccsc1)C2]

To a solution of ethyl 10-methoxy-9-(3-methoxypropoxy)-2-oxo-6-(3-thienyl)-6,7-dihydrobenzo[a]quinolizine-3-carboxylate (250 mg, 532 μmol) in EtOH (3 mL) was added 2 M NaOH aqueous solution (0.8 mL). The mixture was stirred at rt for 0.5 hr and then concentrated under reduced pressure to remove most of EtOH. The residue was acidified by 1 M hydrochloric acid and then filtered. The filter cake was purified by column chromatography to give 10-methoxy-9-(3-methoxypropoxy)-2-oxo-6-(3-thienyl)-6,7-dihydrobenzo[a]quinolizine-3-carboxylic acid (110 mg) as a pale yellow solid. $^1$H NMR (400 MHz, DMSO-d6): δ 1.97 (q, 2H) 3.26 (s, 3H) 3.36-3.45 (m, 1H) 3.49 (t, 2H) 3.59 (dd, 1H) 3.87 (s, 3H) 4.10 (t, 2H) 5.99 (br. s., 1H) 6.83 (d, 1H) 6.99 (s, 1H) 7.11 (br. s., 1H) 7.26-7.55 (m, 3H) 8.74 (br. s., 1H). MS obsd. (ESI$^+$) [(M+H)$^+$]: 442.

Example 3: 10-methoxy-9-(3-methoxypropoxy)-2-oxo-6-(2-thienyl)-6,7-dihydrobenzo[a]quinolizine-3-carboxylic Acid

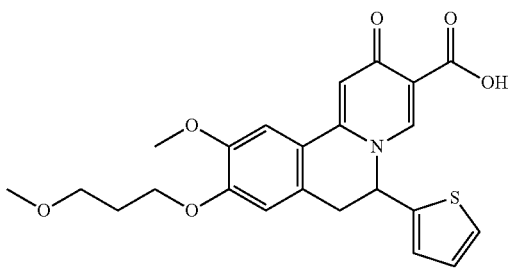 [SMILES: COCCCOc1cc2c(cc1OC)-c1cc(=O)c(C(=O)O)cn1C(c1cccs1)C2]

Step 1: Preparation of 2-[4-methoxy-3-(3-methoxypropoxy)phenyl]-1-(2-thienyl)ethanone

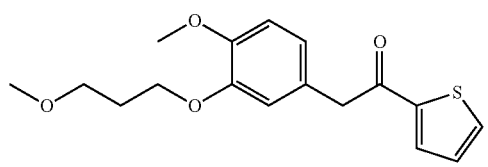 [SMILES: COCCCOc1cc(CC(=O)c2cccs2)ccc1OC]

A mixture of 4-bromo-1-methoxy-2-(3-methoxypropoxy)benzene (5.0 g, 18.2 mmol), 1-(2-thienyl)ethanone (3.43 g, 27.2 mmol), Xantphos (440 mg), Pd$_2$(dba)$_3$ (340 mg) and t-BuONa (2.61 g, 27.2 mmol) in THF (50 mL) was heated at 70° C. for 5 hrs. After being cooled to rt, the mixture was filtered. The filtrate was concentrated under reduced pressure and the residue was purified by column chromatography to give 2-[4-methoxy-3-(3-methoxypropoxy)phenyl]-1-(2-thienyl)ethanone (2.7 g) as a yellow solid.

Step 2: Preparation of 2-[4-methoxy-3-(3-methoxypropoxy)phenyl]-1-(2-thienyl)ethanamine

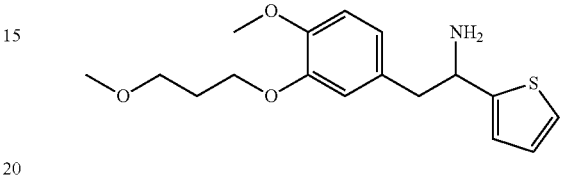

To a solution of 2-[4-methoxy-3-(3-methoxypropoxy)phenyl]-1-(2-thienyl)ethanone (2.7 g, 8.43 mmol) in MeOH (40 mL) was added NH$_4$OAc (6.50 g, 84.3 mmol). After the mixture was stirred for 20 min, to the resulting mixture was added NaBH$_3$CN (1.06 g, 16.8 mmol). The resulting mixture was heated and stirred at 40° C. for 24 hrs and then concentrated under reduced pressure. The residue was diluted with DCM. The organic mixture was washed with water and brine, dried over anhydrous Na$_2$SO$_4$ and concentrated under reduced pressure to give crude 2-[4-methoxy-3-(3-methoxypropoxy)phenyl]-1-(2-thienyl)ethanamine (2.2 g) as a yellow oil, which was used directly in the next step without further purification.

Step 3: Preparation of N-[2-[4-methoxy-3-(3-methoxypropoxy)phenyl]-1-(2-thienyl)ethyl]formamide

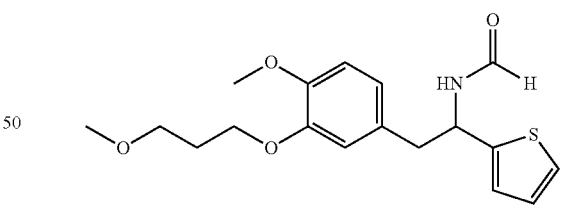

To a solution of 2-[4-methoxy-3-(3-methoxypropoxy)phenyl]-1-(2-thienyl)ethanamine (crude 2.2 g) in dioxane (30 mL) was added formic acid (1.54 g, 33.6 mmol). The mixture was refluxed for 24 hrs. After being cooled to rt, the mixture was concentrated under reduced pressure. The residue was diluted with DCM. The organic mixture was washed with water and brine, dried over anhydrous Na$_2$SO$_4$ and concentrated under reduced pressure. The residue was purified by column chromatography to give N-[2-[4-methoxy-3-(3-methoxypropoxy)phenyl]-1-(2-thienyl)ethyl]formamide (800 mg) as a gray solid.

Step 4: Preparation of 7-methoxy-6-(3-methoxy-propoxy)-3-(2-thienyl)-3,4-dihydroisoquinoline

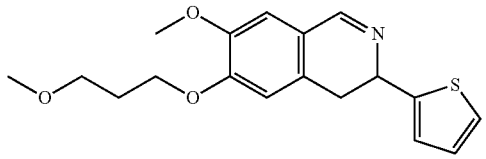 [SMILES: COCCCOc1cc2c(cc1OC)C=NC(c1cccs1)C2]

To a solution of N-[2-[4-methoxy-3-(3-methoxypropoxy)phenyl]-1-(2-thienyl)ethyl]formamide (750 mg, 2.15 mmol) in DCM (10 mL) was added POCl$_3$ (493 mg, 3.22 mmol). The mixture was heated and stirred at 40° C. for 2 hrs, and then poured into ammonia water. The resulting mixture was extracted with DCM. The organic layer was washed with brine, dried over anhydrous Na$_2$SO$_4$ and concentrated under reduced pressure. The residue was purified by column chromatography to give 7-methoxy-6-(3-methoxypropoxy)-3-(2-thienyl)-3,4-dihydroisoquinoline (400 mg) as a gray solid.

Step 5: Preparation of ethyl 10-methoxy-9-(3-methoxypropoxy)-2-oxo-6-(2-thienyl)-1,6,7,11b-tetrahydrobenzo[a]quinolizine-3-carboxylate

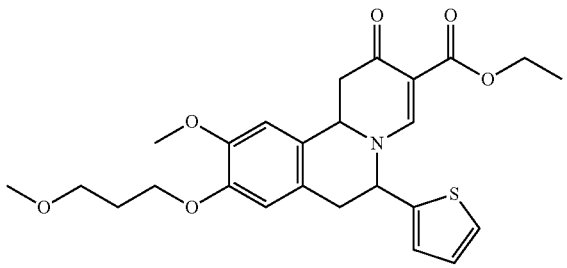 [SMILES: CCOC(=O)C1=CN2C(c3cccs3)Cc3cc(OCCCOC)c(OC)cc3C2CC1=O]

A mixture of 7-methoxy-6-(3-methoxypropoxy)-3-(2-thienyl)-3,4-dihydroisoquinoline (50 mg, 0.15 mmol) and ethyl 2-(ethoxymethylene)-3-oxo-butanoate (84 mg, 0.45 mmol) in EtOH (1 mL) was refluxed for 24 hrs. After being cooled to rt, the mixture was concentrated under reduced pressure to give crude ethyl 10-methoxy-9-(3-methoxypropoxy)-2-oxo-6-(2-thienyl)-1,6,7,11b-tetrahydrobenzo[a]quinolizine-3-carboxylate (70 mg), which was used directly in the next step without further purification.

Step 6: Preparation of ethyl 10-methoxy-9-(3-methoxypropoxy)-2-oxo-6-(2-thienyl)-6,7-dihydrobenzo[a]quinolizine-3-carboxylate

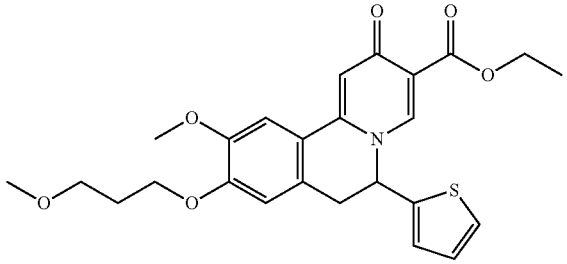 [SMILES: CCOC(=O)c1cn2c(cc1=O)-c1cc(OC)c(OCCCOC)cc1CC2c1cccs1]

To a solution of ethyl 10-methoxy-9-(3-methoxypropoxy)-2-oxo-6-(2-thienyl)-1,6,7,11b-tetrahydrobenzo[a]quinolizine-3-carboxylate (crude 70 mg, 0.15 mmol) in DME (1 mL) was added p-chloranil (37 mg, 0.15 mmol). The resulting mixture was refluxed for 3 hrs, and then filtered. The filtrate was concentrated under reduced pressure. The residue was diluted with DCM. The organic mixture was washed with NaHCO$_3$ aqueous solution and brine, dried over anhydrous Na$_2$SO$_4$ and concentrated under reduced pressure to give crude ethyl 10-methoxy-9-(3-methoxypropoxy)-2-oxo-6-(2-thienyl)-6,7-dihydrobenzo[a]quinolizine-3-carboxylate (60 mg), which was used directly in the next step without further purification.

Step 7: Preparation of 10-methoxy-9-(3-methoxypropoxy)-2-oxo-6-(2-thienyl)-6,7-dihydrobenzo[a]quinolizine-3-carboxylic Acid

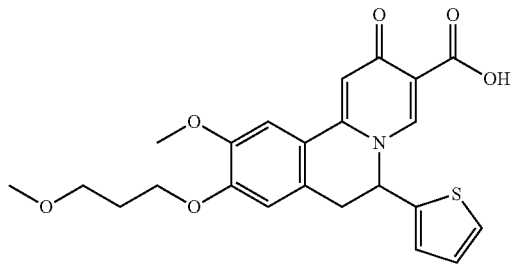 [SMILES: COCCCOc1cc2c(cc1OC)-c1cc(=O)c(C(=O)O)cn1C(c1cccs1)C2]

To a mixture of ethyl 10-methoxy-9-(3-methoxypropoxy)-2-oxo-6-(2-thienyl)-6,7-dihydrobenzo[a]quinolizine-3-carboxylate (crude 60 mg, 0.15 mmol) in MeOH (1 mL) was added 2 M NaOH aqueous solution (0.15 mL, 0.3 mmol). After being stirred at rt for 16 hrs, the resulting mixture was concentrated under reduced pressure to remove most of MeOH. The residue was acidified with 2 M hydrochloric acid to pH=3, and then extracted with DCM. The organic layer was dried over anhydrous Na$_2$SO$_4$ and concentrated under reduced pressure. The residue was purified by prep-HPLC to give 10-methoxy-9-(3-methoxypropoxy)-2-oxo-6-(2-thienyl)-6,7-dihydrobenzo[a]quinolizine-3-carboxylic acid (2.4 mg) as a gray solid. $^1$H NMR (400 MHz, DMSO-d6): δ: 8.99 (s, 1H), 7.50-7.53 (m, 2H), 7.33-7.38 (m, 1H), 7.08 (s, 1H), 7.03 (s, 1H), 6.86-7.01 (m, 1H), 6.35 (s, 1H), 4.08 (t, 2H), 3.87 (s, 3H), 3.66-3.70 (m, 1H), 3.46 (t, 2H), 3.43-3.45 (m, 2H), 3.24 (s, 3H), 1.94-2.01 (m, 2H). MS obsd. (ESI$^+$) [(M+H)$^+$]: 442.

Example 4: 6-(4-hydroxyphenyl)-10-methoxy-9-(3-methoxypropoxy)-2-oxo-6,7-dihydrobenzo[a]quinolizine-3-carboxylic Acid

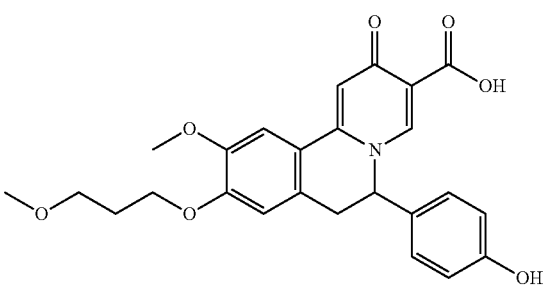 [SMILES: COCCCOc1cc2c(cc1OC)-c1cc(=O)c(C(=O)O)cn1C(c1ccc(O)cc1)C2]

Step 1: Preparation of 1-(4-benzyloxyphenyl)-2-[4-methoxy-3-(3-methoxypropoxy)phenyl]ethanone

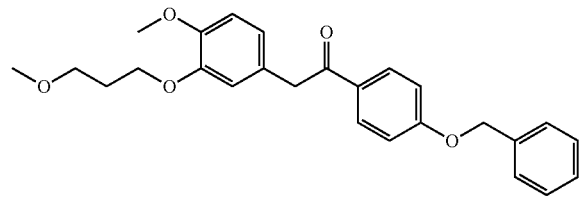 [SMILES: COCCCOc1cc(CC(=O)c2ccc(OCc3ccccc3)cc2)ccc1OC]

To a mixture of 4-bromo-1-methoxy-2-(3-methoxypropoxy)benzene (15 g, 54.5 mmol) in THF (150 mL) was added 1-(4-benzyloxyphenyl)ethanone (16 g, 70.9 mmol), t-BuONa (7.86 g, 81.8 mmol), $Pd_2(dba)_3$ (1 g, 1.09 mmol) and Xantphos (1.26 g, 2.18 mmol). The mixture was heated at 50° C. for 4 hrs. After being cooled to rt, the mixture was concentrated under reduced pressure, and the residue was dissolved in DCM. The organic solution was washed with $H_2O$ and brine, dried over anhydrous $Na_2SO_4$ and concentrated under reduced pressure. The residue was purified by column chromatography to give 1-(4-benzyloxyphenyl)-2-[4-methoxy-3-(3-methoxypropoxy)phenyl]ethanone (17 g) as a yellow solid.

Step 2: Preparation of 1-(4-benzyloxyphenyl)-2-[4-methoxy-3-(3-methoxypropoxy)phenyl]ethanamine To a solution of 1-(4-benzyloxyphenyl)-2-[4-methoxy-3-(3-methoxypropoxy)phenyl]ethanone (17 g, 40.4 mmol) in MeOH (170 mL) was added $NH_4OAc$ (31.2 g, 404 mmol) at 70° C. After being heated for 1 hr, the resulting mixture was cooled to 0° C. Then to the resulting mixture was added $NaBH_3CN$ (5.08 g, 80.9 mmol) at 0° C. The resulting mixture was heated at 80° C. for 12 hrs and then concentrated under reduced pressure to remove most of MeOH. The residue was diluted with $H_2O$ (100 mL) and extracted with DCM (500 mL). The organic layer was washed with brine (100 mL), dried over anhydrous $Na_2SO_4$ and concentrated under reduced pressure to afford crude 1-(4-benzyloxyphenyl)-2-[4-methoxy-3-(3-methoxypropoxy)phenyl]ethanamine (24 g) as a yellow oil, which was used directly in the next step without further purification.

Step 3: Preparation of N-[1-(4-benzyloxyphenyl)-2-[4-methoxy-3-(3-methoxypropoxy)phenyl]ethyl]formamide

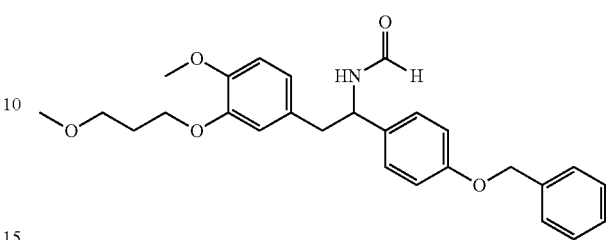

To a mixture of 1-(4-benzyloxyphenyl)-2-[4-methoxy-3-(3-methoxypropoxy)phenyl]ethanamine (24.0 g, 56.9 mmol) in dioxane (250 mL) was added formic acid (13.1 g, 285 mmol). After being heated at 120° C. for 12 hrs, the mixture was concentrated under reduced pressure to remove most of dioxane. The residue was partitioned between $H_2O$ (200 mL) and DCM (600 mL). The organic layer was separated, washed with brine (200 mL), dried over anhydrous $Na_2SO_4$ and concentrated under reduced pressure. The residue was purified by column chromatography to give N-[1-(4-benzyloxyphenyl)-2-[4-methoxy-3-(3-methoxypropoxy)phenyl]ethyl]formamide (13.0 g) as a light yellow solid.

Step 4: Preparation of 3-(4-benzyloxyphenyl)-7-methoxy-6-(3-methoxypropoxy)-3,4-dihydroisoquinoline To a mixture of N-[1-(4-benzyloxyphenyl)-2-[4-methoxy-3-(3-methoxypropoxy)phenyl]ethyl]formamide (11.0 g, 24.5 mmol) in dry DCM (120 mL) was added $POCl_3$ (5.75 g, 37.5 mmol) drop-wise at 0° C. Then the mixture was refluxed for 12 hrs. After being cooled to rt, the mixture was poured into a solution of ammonia water (30 mL) in $H_2O$ (20 mL). Then the mixture was extracted with DCM (300 mL). The organic layer was washed with brine (150 mL), dried over anhydrous $Na_2SO_4$ and concentrated under reduced pressure. The residue was purified by column chromatography to give 3-(4-benzyloxyphenyl)-7-methoxy-6-(3-methoxypropoxy)-3,4-dihydroisoquinoline (8.4 g) as a yellow solid.

Step 5: Preparation of ethyl 6-(4-benzyloxyphenyl)-10-methoxy-9-(3-methoxypropoxy)-2-oxo-1,6,7,11b-tetrahydrobenzo[a]quinolizine-3-carboxylate

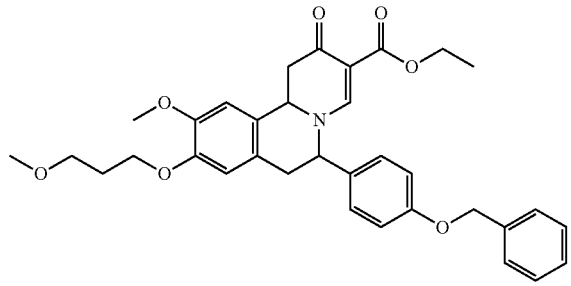

A solution of 3-(4-benzyl oxyphenyl)-7-methoxy-6-(3-methoxypropoxy)-3,4-dihydroisoquinoline (4.0 g, 9.27 mmol) and ethyl 2-(ethoxymethylene)-3-oxo-butanoate (5.18 g, 27.8 mmol) in EtOH (50 mL) was heated in a 100° C. oil bath for 12 hrs. After being cooled to rt, the mixture was concentrated under reduced pressure to afford crude ethyl 6-(4-benzyloxyphenyl)-10-methoxy-9-(3-methoxypropoxy)-2-oxo-1,6,7,11 b-tetrahydrobenzo[a]quinolizine-3-carboxylate, which was used directly in the next step without further purification.

Step 6: Preparation of ethyl 6-(4-benzyloxyphenyl)-10-methoxy-9-(3-methoxypropoxy)-2-oxo-6,7-dihydrobenzo[a]quinolizine-3-carboxylate

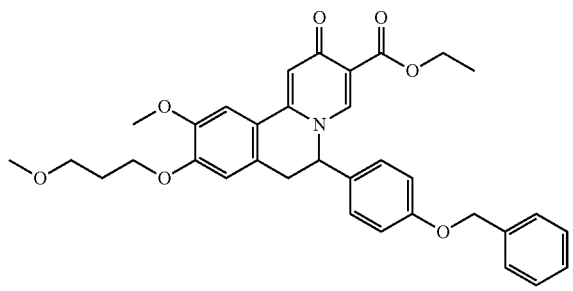 [SMILES: CCOC(=O)c1cn2c(cc1=O)-c1cc(OC)c(OCCCOC)cc1CC2c1ccc(OCc2ccccc2)cc1]

A mixture of ethyl 6-(4-benzyloxyphenyl)-10-methoxy-9-(3-methoxypropoxy)-2-oxo-1,6,7,11b-tetrahydrobenzo[a]quinolizine-3-carboxylate (5.3 g, 9.27 mmol) and p-chloranil (1.6 g, 6.49 mmol) in DME (60 mL) was heated at 80° C. for 3 hrs. After being cooled to rt, the mixture was partitioned between H$_2$O (150 mL) and DCM (300 mL). The organic layer was separated, washed with brine (150 mL), dried over anhydrous Na$_2$SO$_4$ and concentrated under reduced pressure. The residue was purified by column chromatography to afford ethyl 6-(4-benzyloxyphenyl)-10-methoxy-9-(3-methoxypropoxy)-2-oxo-6,7-dihydrobenzo[a]quinolizine-3-carboxylate (4 g) as a black solid.

Step 7: Preparation of ethyl 6-(4-hydroxyphenyl)-10-methoxy-9-(3-methoxypropoxy)-2-oxo-6,7-dihydrobenzo[a]quinolizine-3-carboxylate

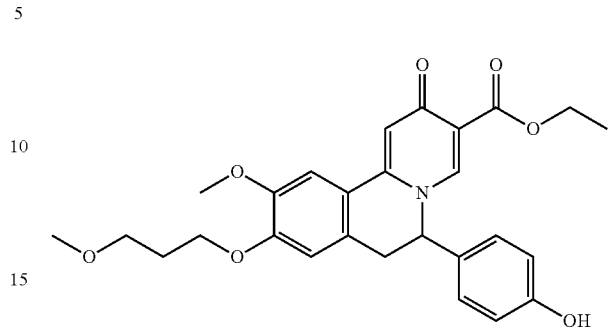

To a solution of ethyl 6-(4-benzyloxyphenyl)-10-methoxy-9-(3-methoxypropoxy)-2-oxo-6,7-dihydrobenzo[a]quinolizine-3-carboxylate (700 mg, 1.23 mmol) in EtOH (10 mL) was added Pd/C (50 mg). Then the mixture was heated to 30° C. and stirred at 30° C. under hydrogen atmosphere (30 psi) for 12 hrs. After being cooled to rt, the mixture was concentrated under reduced pressure to give crude ethyl 6-(4-hydroxyphenyl)-10-methoxy-9-(3-methoxypropoxy)-2-oxo-6,7-dihydrobenzo[a]quinolizine-3-carboxylate (650 mg) as a black solid, which was used directly in the next step without purification.

Step 8: Preparation of 6-(4-hydroxyphenyl)-10-methoxy-9-(3-methoxypropoxy)-2-oxo-6,7-dihydrobenzo[a]quinolizine-3-carboxylic Acid

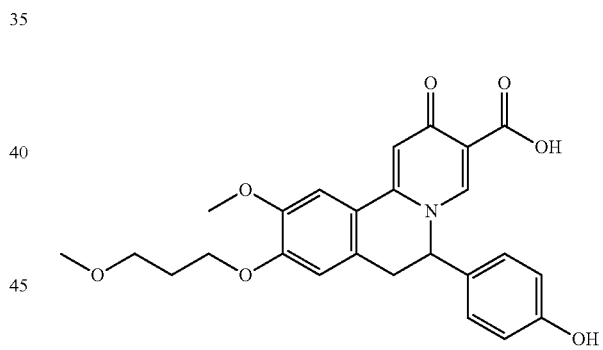

To a solution of ethyl 6-(4-hydroxyphenyl)-10-methoxy-9-(3-methoxypropoxy)-2-oxo-6,7-dihydrobenzo[a]quinolizine-3-carboxylate (200 mg, 417 μmol) in MeOH (5 mL) was added 2 M NaOH aqueous solution (0.625 mL, 1.25 mmol). After being stirred at 25° C. for 12 hrs, the resulting mixture was concentrated. The residue was diluted with H$_2$O (20 mL), acidified with 1 M hydrochloric acid to pH=3, and extracted with DCM (100 mL). The organic layer was washed with brine (50 mL), dried over anhydrous Na$_2$SO$_4$ and concentrated under reduced pressure. The residue was purified by prep-HPLC to give 6-(4-hydroxyphenyl)-10-methoxy-9-(3-methoxypropoxy)-2-oxo-6,7-dihydrobenzo[a]quinolizine-3-carboxylic acid (8.2 mg) as a white solid. $^1$H NMR (400 MHz, METHANOL-d$_4$): δ: 1.94-2.10 (m, 2H), 3.07-3.30 (m, 3H), 3.33-3.37 (m, 1H), 3.42-3.53 (m, 1H), 3.55 (t, 2H), 3.88 (br. s., 3H), 4.08 (br. s., 2H), 5.51 (br. s., 1H), 6.64 (br. s., 2H), 6.74-7.15 (m, 4H), 7.32 (br. s., 1H), 8.24 (br. s., 1H). MS obsd. (ESI$^+$) [(M+H)$^+$]: 452.

Example 5: 10-methoxy-6-(4-methoxyphenyl)-9-(3-methoxypropoxy)-2-oxo-6,7-dihydrobenzo[a]quinolizine-3-carboxylic Acid

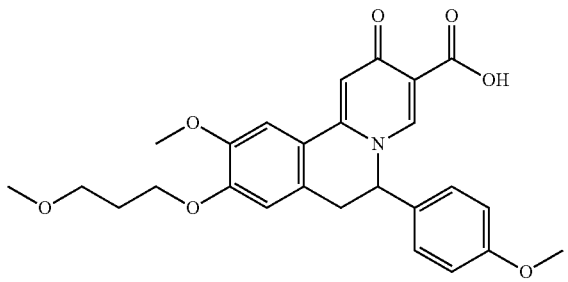

Step 1: Preparation of ethyl 10-methoxy-6-(4-methoxyphenyl)-9-(3-methoxypropoxy)-2-oxo-6,7-dihydrobenzo[a]quinolizine-3-carboxylate

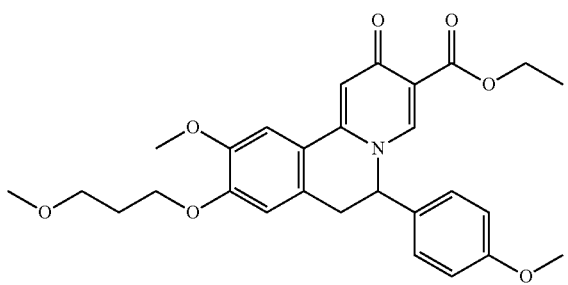

To a solution of ethyl 6-(4-hydroxyphenyl)-10-methoxy-9-(3-methoxypropoxy)-2-oxo-6,7-dihydrobenzo[a]quinolizine-3-carboxylate (450 mg, 938 μmol, from step 7 of Example 4) in DMF (10 mL) was added K$_2$CO$_3$ (389 mg, 2.82 mmol) and iodomethane (2.05 g, 14.4 mmol). The mixture was stirred at 25° C. for 24 hrs, and then partitioned between H$_2$O (50 mL) and EtOAc (100 mL). The organic layer was washed with brine (50 mL), dried over anhydrous Na$_2$SO$_4$ and concentrated under reduced pressure to afford crude ethyl 10-methoxy-6-(4-methoxyphenyl)-9-(3-methoxypropoxy)-2-oxo-6,7-dihydrobenzo[a]quinolizine-3-carboxylate (350 mg) as a brown oil, which was used directly in the next step without further purification.

Step 2: Preparation of 10-methoxy-6-(4-methoxyphenyl)-9-(3-methoxypropoxy)-2-oxo-6,7-dihydrobenzo[a]quinolizine-3-carboxylic Acid

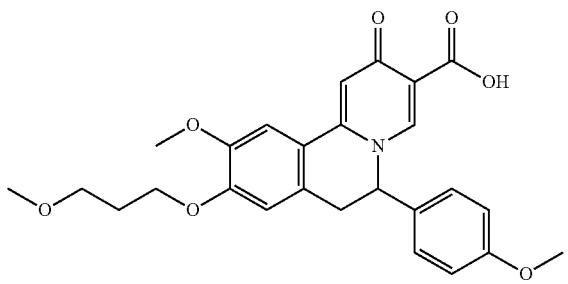

To a solution of ethyl 10-methoxy-6-(4-methoxyphenyl)-9-(3-methoxypropoxy)-2-oxo-6,7-dihydrobenzo[a]quinolizine-3-carboxylate (350 mg, 790 μmol) in MeOH (5 mL) was added 2 M NaOH aqueous solution (1.19 mL, 2.37 mmol). After being stirred at 25° C. for 12 hrs, the resulting reaction mixture was diluted with H$_2$O (20 mL), acidified with 1 M hydrochloric acid to pH=3 and extracted with DCM (100 mL). The organic layer was washed with brine (50 mL), dried over anhydrous Na$_2$SO$_4$ and concentrated under reduced pressure. The residue was purified by prep-HPLC to afford 10-methoxy-6-(4-methoxyphenyl)-9-(3-methoxypropoxy)-2-oxo-6,7-dihydrobenzo[a]quinolizine-3-carboxylic acid (27 mg) as a yellow solid. $^1$H NMR (400 MHz, CDCl$_3$): δ: 2.12 (q, 2H), 3.28 (dd, 1H), 3.34 (s, 3H), 3.55 (t, 3H), 3.60 (d, 1H), 3.77 (s, 3H) 3.94 (s, 3H), 4.13 (t, 2H), 5.39 (s, 1H), 6.69 (s, 1H), 6.79-6.86 (m, 2H), 6.88-6.95 (m, 2H), 7.15 (s, 1H), 7.20 (s, 1H), 8.45 (s, 1H). MS obsd. (ESI$^+$) [(M+H)$^+$]: 466.

Example 6: 6-(4-benzyloxyphenyl)-10-methoxy-9-(3-methoxypropoxy)-2-oxo-6,7-dihydrobenzo[a]quinolizine-3-carboxylic Acid

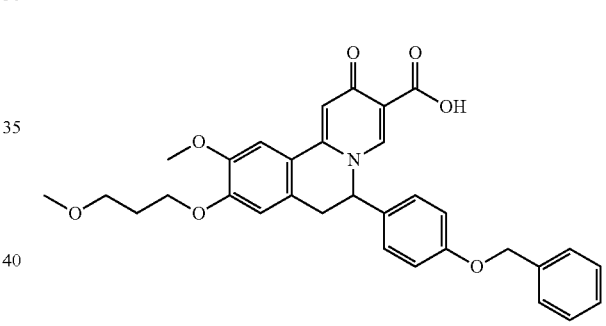

To a solution of ethyl 6-(4-benzyloxyphenyl)-10-methoxy-9-(3-methoxypropoxy)-2-oxo-6,7-dihydrobenzo[a]quinolizine-3-carboxylate (200 mg, 351 μmol, from step 6 of Example 4) in MeOH (5 mL) was added 2 M NaOH aqueous solution (0.526 mL, 1.05 mmol). After being stirred at 25° C. for 12 hrs, the resulting mixture was diluted with H$_2$O (20 mL), acidified with 1 M hydrochloric acid to pH=3 and extracted with DCM (100 mL). The organic layer was washed with brine (50 mL), dried over anhydrous Na$_2$SO$_4$ and concentrated under reduced pressure. The residue was purified by prep-HPLC to afford 6-(4-benzyloxyphenyl)-10-methoxy-9-(3-methoxypropoxy)-2-oxo-6,7-dihydrobenzo[a]quinolizine-3-carboxylic acid (31 mg) as a white solid. $^1$H NMR (400 MHz, CDCl$_3$): δ: 2.12 (q, 2H), 3.28 (dd, 1H), 3.34 (s, 3H), 3.55 (t, 3H), 3.93 (s, 3H), 4.13 (t, 2H), 5.02 (s, 2H), 5.40 (br. s., 1H), 6.69 (s, 1H), 6.82-6.96 (m, 4H), 7.17 (d, 2H), 7.31-7.45 (m, 5H), 8.46 (s, 1H). MS obsd. (ESI$^+$) [(M+H)$^+$]: 542.

Example 7: 10-methoxy-9-(3-methoxypropoxy)-6-(4-methyl-2-thienyl)-2-oxo-6,7-dihydrobenzo[a]quinolizine-3-carboxylic Acid

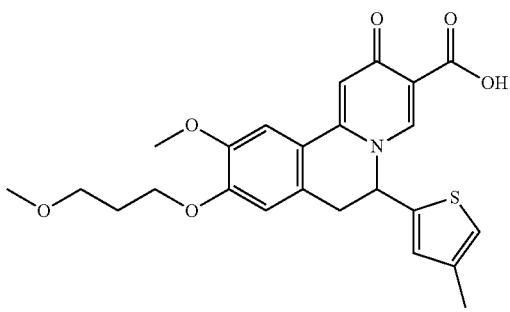 [SMILES: COCCCOc1cc2c(cc1OC)-c1cc(=O)c(C(=O)O)cn1C(c1cc(C)cs1)C2]

Step 1: Preparation of 2-[4-methoxy-3-(3-methoxypropoxy)phenyl]-1-(4-methyl-2-thienyl)ethanone

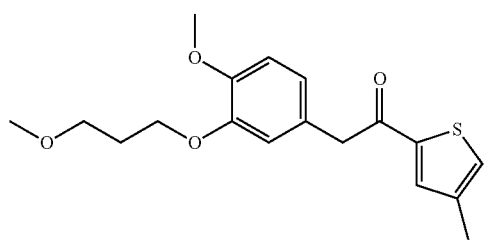 [SMILES: COCCCOc1cc(CC(=O)c2cc(C)cs2)ccc1OC]

A mixture of 4-bromo-1-methoxy-2-(3-methoxypropoxy)benzene (5.0 g, 18.2 mmol), 1-(4-methyl-2-thienyl)ethanone (3.82 g, 27.2 mmol), t-BuONa (2.80 g, 29.1 mmol), Pd$_2$(dba)$_3$ (350 mg) and Xantphos (440 mg) in THF (60 mL) was heated at 80° C. for 3 hrs. After being cooled to rt, the mixture was partitioned between DCM (200 mL) and H$_2$O (50 mL). The organic layer was separated, washed with brine (50 mL), dried over anhydrous Na$_2$SO$_4$ and concentrated under reduced pressure. The residue was purified by column chromatography to give 2-[4-methoxy-3-(3-methoxypropoxy)phenyl]-1-(4-methyl-2-thienyl)ethanone (3.7 g) as a yellow solid.

Step 2: Preparation of 2-[4-methoxy-3-(3-methoxypropoxy)phenyl]-1-(4-methyl-2-thienyl)ethanamine

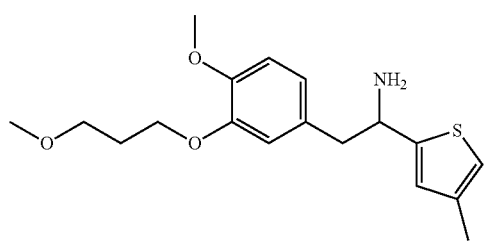 [SMILES: COCCCOc1cc(CC(N)c2cc(C)cs2)ccc1OC]

To a mixture of 2-[4-methoxy-3-(3-methoxypropoxy)phenyl]-1-(4-methyl-2-thienyl)ethanone (3.7 g, 11.1 mmol) in MeOH (50 mL) was added NH$_4$OAc (8.53 g, 111 mmol). The mixture was heated at 40° C. for 1 hr. Then to the resulting mixture was added NaBH$_3$CN (1.39 g, 22.2 mmol). The resulting mixture was heated at 70° C. for 48 hrs, and then concentrated under reduced pressure. The residue was diluted with DCM (200 mL). The organic mixture was separated, washed with water (100 mL) and brine (100 mL), dried over anhydrous Na$_2$SO$_4$ and concentrated under reduced pressure. The residue was purified by column chromatography to give crude 2-[4-methoxy-3-(3-methoxypropoxy)phenyl]-1-(4-methyl-2-thienyl)ethanamine (2.5 g) as a yellow oil.

Step 3: Preparation of N-[2-[4-methoxy-3-(3-methoxypropoxy)phenyl]-1-(4-methyl-2-thienyl)ethyl]formamide

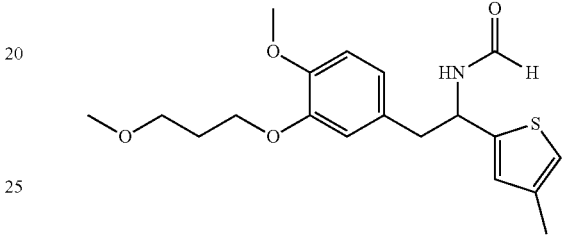

To a mixture of 2-[4-methoxy-3-(3-methoxypropoxy)phenyl]-1-(4-methyl-2-thienyl)ethanamine (2.5 g, 7.46 mmol) in dioxane (30 mL) was added formic acid (1.72 g, 37.3 mmol). The mixture was heated at reflux for 24 hrs. After being cooled to rt, the mixture was concentrated under reduced pressure and the residue was diluted with DCM (100 mL). Then the organic mixture was separated, washed with water (50 mL) and brine (50 mL), dried over anhydrous Na$_2$SO$_4$ and concentrated under reduced pressure. The residue was purified by column chromatography to give N-[2-[4-methoxy-3-(3-methoxypropoxy)phenyl]-1-(4-methyl-2-thienyl)ethyl]formamide (1.3 g) as a yellow oil.

Step 4: Preparation of 7-methoxy-6-(3-methoxypropoxy)-3-(4-methyl-2-thienyl)-3,4-dihydroisoquinoline

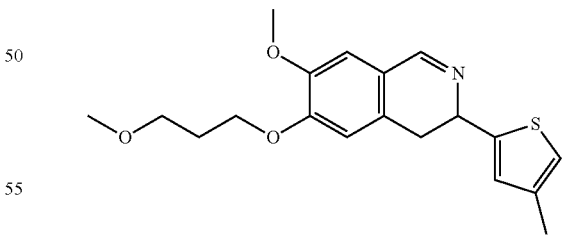

To a mixture of N-[2-[4-methoxy-3-(3-methoxypropoxy)phenyl]-1-(4-methyl-2-thienyl)ethyl]formamide (700 mg, 1.93 mmol) in DCM (10 mL) was added POCl$_3$ (442 mg, 2.89 mmol). The mixture was heated under reflux for 2 hrs. After being cooled to rt, the mixture was partitioned between ammonia water (20 mL) and DCM (100 mL). The organic layer was separated, washed with water (30 mL) and brine (30 mL), dried over anhydrous Na$_2$SO$_4$ and concentrated under reduced pressure. The residue was purified by column chromatography to give 7-methoxy-6-(3-methoxypropoxy)-3-(4-methyl-2-thienyl)-3,4-dihydroisoquinoline (390 mg) as a white solid.

Step 5: Preparation of ethyl 10-methoxy-9-(3-methoxypropoxy)-6-(4-methyl-2-thienyl)-2-oxo-1,6,7,11b-tetrahydrobenzo[a]quinolizine-3-carboxylate

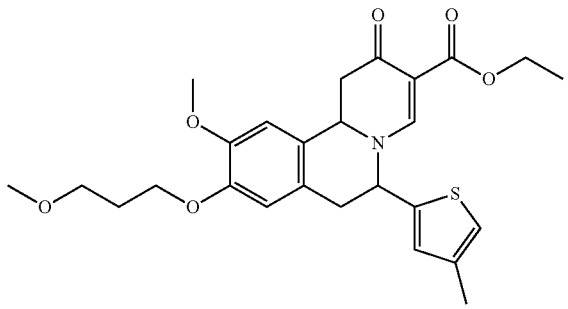 [SMILES: CCOC(=O)C1=CN2C(c3cc(C)cs3)Cc3cc(OCCCOC)c(OC)cc3C2CC1=O]

A mixture of 7-methoxy-6-(3-methoxypropoxy)-3-(4-methyl-2-thienyl)-3,4-dihydroisoquinoline (390 mg, 1.13 mmol) and ethyl 2-(ethoxymethylene)-3-oxo-butanoate (630 mg, 3.39 mmol) in EtOH (7 mL) was heated under reflux for 24 hrs. After being cooled to rt, the mixture was concentrated under reduced pressure to give crude ethyl 10-methoxy-9-(3-methoxypropoxy)-6-(4-methyl-2-thienyl)-2-oxo-1,6,7,11b-tetrahydrobenzo[a]quinolizine-3-carboxylate (1.0 g), which was used directly in the next step without further purification.

Step 6: Preparation of ethyl 10-methoxy-9-(3-methoxypropoxy)-6-(4-methyl-2-thienyl)-2-oxo-6,7-dihydrobenzo[a]quinolizine-3-carboxylate

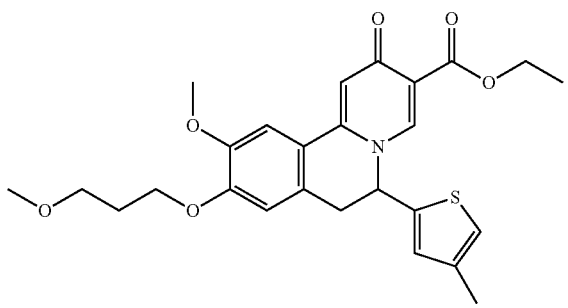 [SMILES: CCOC(=O)c1cn2c(cc1=O)-c1cc(OC)c(OCCCOC)cc1CC2c1cc(C)cs1]

A mixture of ethyl 10-methoxy-9-(3-methoxypropoxy)-6-(4-methyl-2-thienyl)-2-oxo-1,6,7,11b-tetrahydrobenzo[a]quinolizine-3-carboxylate (crude 1 g) and p-chloranil (277 mg, 1.13 mmol) in DME (10 mL) was heated under reflux for 3 hrs. Then the mixture was filtered. The filtrate was concentrated under reduced pressure. The residue was diluted with DCM. Then the organic mixture was washed with NaHCO$_3$ aqueous solution and brine, dried over anhydrous Na$_2$SO$_4$ and concentrated under reduced pressure to give crude ethyl 10-methoxy-9-(3-methoxypropoxy)-6-(4-methyl-2-thienyl)-2-oxo-6,7-dihydrobenzo[a]quinolizine-3-carboxylate (1 g), which was used directly in the next step without further purification.

Step 7: Preparation of 10-methoxy-9-(3-methoxypropoxy)-6-(4-methyl-2-thienyl)-2-oxo-6,7-dihydrobenzo[a]quinolizine-3-carboxylic Acid

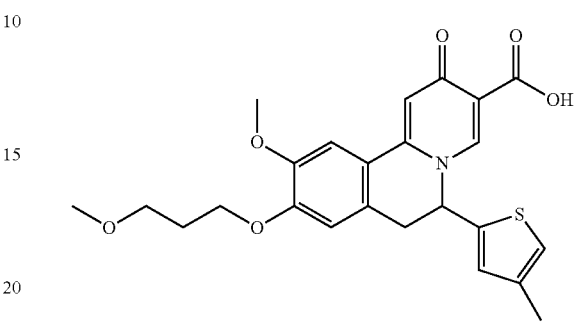

To a mixture of crude ethyl 10-methoxy-9-(3-methoxypropoxy)-6-(4-methyl-2-thienyl)-2-oxo-6,7-dihydrobenzo[a]quinolizine-3-carboxylate (1 g) in MeOH (10 mL) was added 2 M NaOH aqueous solution (1.1 mL). The mixture was stirred at 15° C. for 16 hrs. The mixture was concentrated under reduced pressure. The residue was acidified with 1 M hydrochloric acid to pH=3. The resulting aqueous mixture was extracted with DCM. The organic layer was dried over anhydrous Na$_2$SO$_4$ and concentrated under reduced pressure. The residue was treated with MeOH (5 mL), and then filtered. The filter cake was purified by prep-HPLC to give 10-methoxy-9-(3-methoxypropoxy)-6-(4-methyl-2-thienyl)-2-oxo-6,7-dihydrobenzo[a]quinolizine-3-carboxylic acid (64 mg) as a white solid. $^1$H NMR (400 MHz, DMSO-d6): δ 8.93 (s, 1H), 7.50-7.53 (m, 2H), 7.06 (s, 1H), 6.91 (s, 1H), 6.82 (s, 1H), 6.26 (s, 1H), 4.07 (t, J=6.4 Hz, 2H), 3.87 (s, 3H), 3.66-3.70 (m, 1H), 3.46 (t, J=6.4 Hz, 2H), 3.30-3.31 (m, 1H), 3.24 (s, 3H), 2.07 (s, 3H), 1.94-2.01 (m, 2H). MS obsd. (ESI$^+$) [(M+H)$^+$]: 456.

Example 8: 6-(3-chlorophenyl)-10-methoxy-9-(3-methoxypropoxy)-2-oxo-6,7-dihydrobenzo[a]quinolizine-3-carboxylic Acid

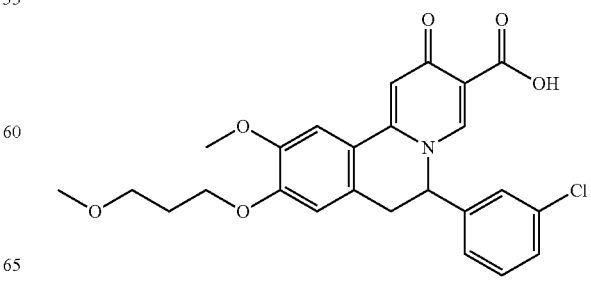

Step 1: Preparation of 1-(3-chlorophenyl)-2-[4-methoxy-3-(3-methoxypropoxy)phenyl]ethanone

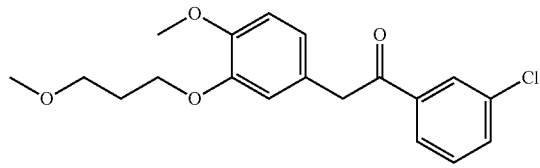 [SMILES: COCCCOc1cc(CC(=O)c2cccc(Cl)c2)ccc1OC]

A mixture of 4-bromo-1-methoxy-2-(3-methoxypropoxy) benzene (10.0 g, 36.3 mmol), 1-(3-chlorophenyl)ethanone (7.3 g, 47.2 mmol), t-BuONa (5.24 g, 54.5 mmol), Pd$_2$(dba)$_3$ (1.33 g, 1.45 mmol) and Xantphos (841 mg, 1.45 mmol) in THF (100 mL) was heated at 60° C. for 12 hrs under nitrogen atmosphere. After being cooled to rt, the reaction mixture was concentrated under reduced pressure. The residue was diluted with DCM (600 mL). The organic mixture was washed with water and brine, dried over anhydrous Na$_2$SO$_4$ and concentrated under reduced pressure. The residue was purified by column chromatography to give 1-(3-chlorophenyl)-2-[4-methoxy-3-(3-methoxypropoxy)phenyl]ethanone (9.0 g) as a light yellow oil.

Step 2: Preparation of 1-(3-chlorophenyl)-2-[4-methoxy-3-(3-methoxypropoxy)phenyl]ethanamine

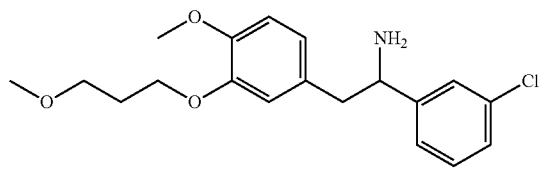 [SMILES: COCCCOc1cc(CC(N)c2cccc(Cl)c2)ccc1OC]

To a mixture of 1-(3-chlorophenyl)-2-[4-methoxy-3-(3-methoxypropoxy)phenyl]ethanone (9.0 g, 25.8 mmol) in MeOH (100 mL) was added NH$_4$OAc (13.9 g, 181 mmol) at 24° C. After the mixture was stirred for 1 hr, to the mixture was added NaBH$_3$CN (14.2 g, 226 mmol) at 0° C. The resulting mixture was heated at 70° C. for 12 hrs, then cooled to rt, and concentrated under reduced pressure to remove most of MeOH. The residue was partitioned between H$_2$O (100 mL) and DCM (500 mL). The organic layer was washed with brine (100 mL), dried over anhydrous Na$_2$SO$_4$ and concentrated under reduced pressure to afford crude 1-(3-chlorophenyl)-2-[4-methoxy-3-(3-methoxypropoxy)phenyl]ethanamine (9.0 g) as a yellow oil, which was used directly in the next step without further purification.

Step 3: Preparation of N-[1-(3-chlorophenyl)-2-[4-methoxy-3-(3-methoxypropoxy)phenyl]ethyl]formamide

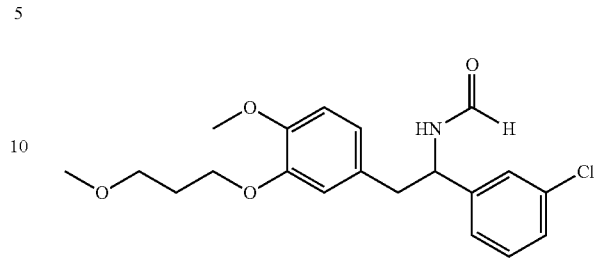

To a mixture of 1-(3-chlorophenyl)-2-[4-methoxy-3-(3-methoxypropoxy)phenyl]ethanamine (9.0 g, 33.4 mmol) in dioxane (120 mL) was added formic acid (5.92 g, 129 mmol) at 24° C. The mixture was refluxed for 12 hrs, then cooled to rt, and concentrated under reduced pressure to remove most of dioxane. The residue was partitioned between H$_2$O (100 mL) and DCM (500 mL). The organic layer was washed with brine (100 mL), dried over anhydrous Na$_2$SO$_4$ and concentrated under reduced pressure. The residue was purified by column chromatography to afford N-[1-(3-chlorophenyl)-2-[4-methoxy-3-(3-methoxypropoxy)phenyl]ethyl]formamide (2.0 g) as a light yellow solid.

Step 4: Preparation of 3-(3-chlorophenyl)-7-methoxy-6-(3-methoxypropoxy)-3,4-dihydroisoquinoline

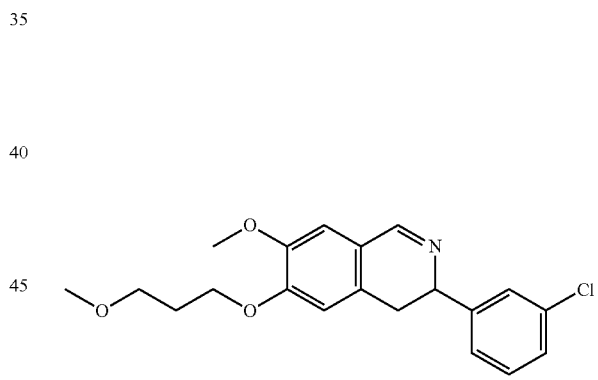

To a mixture of N-[1-(3-chlorophenyl)-2-[4-methoxy-3-(3-methoxypropoxy)phenyl]ethyl]formamide (1.0 g, 2.65 mmol) in DCM (10 mL) was added POCl$_3$ (608 mg, 3.97 mmol). The mixture was heated under reflux for 2 hrs. After being cooled to rt, the mixture was partitioned between ammonia water (20 mL) and DCM (100 mL). The organic layer was separated, washed with water (30 mL) and brine (30 mL), dried over anhydrous Na$_2$SO$_4$ and concentrated under reduced pressure. The residue was purified by column chromatography to give 3-(3-chlorophenyl)-7-methoxy-6-(3-methoxypropoxy)-3,4-dihydroisoquinoline (600 mg) as a brown oil.

Step 5: Preparation of ethyl 6-(3-chlorophenyl)-10-methoxy-9-(3-methoxypropoxy)-2-oxo-1,6,7,11b-tetrahydrobenzo[a]quinolizine-3-carboxylate

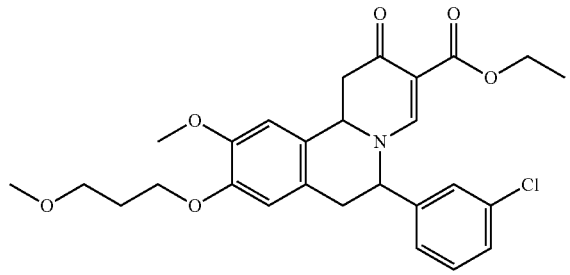 [SMILES: CCOC(=O)C1=CN2C(c3cccc(Cl)c3)Cc3cc(OCCCOC)c(OC)cc3C2CC1=O]

A mixture of 3-(3-chlorophenyl)-7-methoxy-6-(3-methoxypropoxy)-3,4-dihydroisoquinoline (600 mg, 1.67 mmol) and ethyl 2-(ethoxymethylene)-3-oxo-butanoate (930 mg, 5.00 mmol) in EtOH (10 mL) was heated under reflux for 48 hrs. After being cooled to rt, the mixture was concentrated under reduced pressure to give crude ethyl 6-(3-chlorophenyl)-10-methoxy-9-(3-methoxypropoxy)-2-oxo-1,6,7,11 b-tetrahydrobenzo[a]quinolizine-3-carboxylate (1.3 g), which was used directly in the next step without further purification.

Step 6: Preparation of ethyl 6-(3-chlorophenyl)-10-methoxy-9-(3-methoxypropoxy)-2-oxo-6,7-dihydrobenzo[a]quinolizine-3-carboxylate

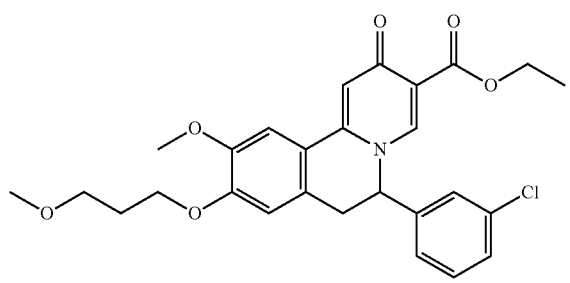 [SMILES: CCOC(=O)c1cn2c(cc1=O)-c1cc(OC)c(OCCCOC)cc1CC2c1cccc(Cl)c1]

A mixture of crude ethyl 6-(3-chlorophenyl)-10-methoxy-9-(3-methoxypropoxy)-2-oxo-1,6,7,11b-tetrahydrobenzo[a]quinolizine-3-carboxylate (1.3 g) and p-chloranil (410 mg, 1.67 mmol) in DME (15 mL) was heated under reflux for 3 hrs. Then the mixture was filtered. The filtrate was concentrated under reduced pressure and the residue was diluted with DCM. Then the organic mixture was washed with NaHCO₃ aqueous solution and brine, dried over anhydrous Na₂SO₄ and concentrated under reduced pressure to give crude ethyl 6-(3-chlorophenyl)-10-methoxy-9-(3-methoxypropoxy)-2-oxo-6,7-dihydrobenzo[a]quinolizine-3-carboxylate (1.4 g), which was used directly in the next step without further purification.

Step 7: Preparation of 6-(3-chlorophenyl)-10-methoxy-9-(3-methoxypropoxy)-2-oxo-6,7-dihydrobenzo[a]quinolizine-3-carboxylic Acid

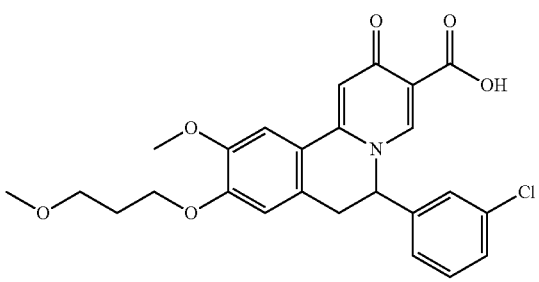 [SMILES: COCCCOc1cc2c(cc1OC)-c1cc(=O)c(C(=O)O)cn1C(c1cccc(Cl)c1)C2]

To a mixture of ethyl 6-(3-chlorophenyl)-10-methoxy-9-(3-methoxypropoxy)-2-oxo-6,7-dihydrobenzo[a]quinolizine-3-carboxylate (crude 700 mg) in MeOH (7 mL) was added 2 M NaOH aqueous solution (0.8 mL). The mixture was stirred at 15° C. for 16 hrs, and then concentrated under reduced pressure. The residue was acidified with 1 M hydrochloric acid to pH=3. The resulting aqueous mixture was extracted with DCM. The organic layer was dried over anhydrous Na$_2$SO$_4$ and concentrated under reduced pressure. The residue was treated with MeOH (5 mL) and then filtered. The filter cake was recrystallized with DMSO/MeCN to give 6-(3-chlorophenyl)-10-methoxy-9-(3-methoxypropoxy)-2-oxo-6,7-dihydrobenzo[a]quinolizine-3-carboxylic acid (36 mg) as a white solid. $^1$H NMR (400 MHz, DMSO-d6): δ 8.85 (s, 1H), 7.58 (s, 1H), 7.52 (s, 1H), 7.23-7.35 (m, 2H), 7.18 (s, 1H), 6.94 (s, 1H), 6.80 (d, 1H), 6.08 (d, 1H), 4.02 (t, 2H), 3.85 (s, 3H), 3.66-3.70 (m, 1H), 3.42-3.50 (m, 3H), 3.21 (s, 3H), 1.94-2.01 (m, 2H). MS obsd. (ESI$^+$) [(M+H)$^+$]: 470.

Example 9: 6-(4-fluorophenyl)-10-methoxy-9-(3-methoxypropoxy)-2-oxo-6,7-dihydrobenzo[a]quinolizine-3-carboxylic Acid

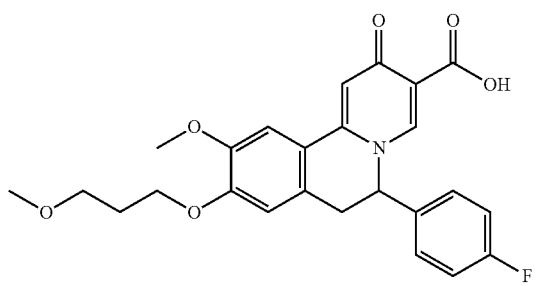 [SMILES: COCCCOc1cc2c(cc1OC)-c1cc(=O)c(C(=O)O)cn1C(c1ccc(F)cc1)C2]

Step 1: Preparation of 1-(4-fluorophenyl)-2-[4-methoxy-3-(3-methoxypropoxy)phenyl]ethanone

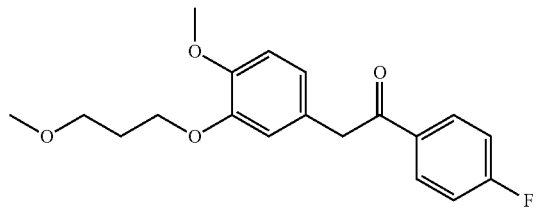 [SMILES: COCCCOc1cc(CC(=O)c2ccc(F)cc2)ccc1OC]

A mixture of 4-bromo-1-methoxy-2-(3-methoxypropoxy) benzene (8.0 g, 29.1 mmol), 1-(4-fluorophenyl)ethanone (6.02 g, 43.6 mmol), t-BuONa (4.47 g, 46.5 mmol), $Pd_2(dba)_3$ (550 mg), Xantphos (700 mg) in THF (100 mL) was heated at 80° C. for 3 hrs. After being cooled to rt, the mixture was concentrated under reduced pressure. The residue was partitioned between DCM (200 mL) and $H_2O$ (50 mL). The organic layer was washed with brine (50 mL), dried over anhydrous $Na_2SO_4$ and concentrated under reduced pressure. The residue was purified by column chromatography to give 1-(4-fluorophenyl)-2-[4-methoxy-3-(3-methoxypropoxy)phenyl]ethanone (8.9 g) as a yellow solid.

Step 2: Preparation of 1-(4-fluorophenyl)-2-[4-methoxy-3-(3-methoxypropoxy)phenyl]ethanamine

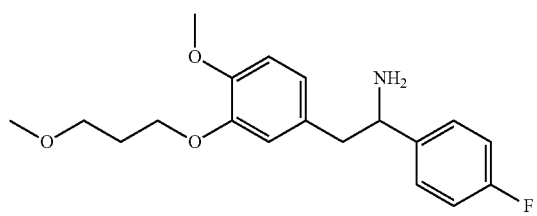 [SMILES: COCCCOc1cc(CC(N)c2ccc(F)cc2)ccc1OC]

To a mixture of 1-(4-fluorophenyl)-2-[4-methoxy-3-(3-methoxypropoxy)phenyl]ethanone (8.9 g, 26.8 mmol) in MeOH (100 mL) was added $NH_4OAc$ (20.6 g, 268 mmol). The mixture was stirred at 30° C. for 1 hr. Then to the mixture was added $NaBH_3CN$ (3.38 g, 53.6 mmol). The resulting mixture was heated at 40° C. for 16 hrs, and then concentrated under reduced pressure. The residue was diluted with DCM (200 mL). The organic mixture was washed with water (100 mL), brine (100 mL), dried over anhydrous $Na_2SO_4$ and concentrated under reduced pressure. The residue was purified by column chromatography to give 1-(4-fluorophenyl)-2-[4-methoxy-3-(3-methoxypropoxy)phenyl]ethanamine (6.0 g) as a yellow oil.

Step 3: Preparation of N-[1-(4-fluorophenyl)-2-[4-methoxy-3-(3-methoxypropoxy)phenyl]ethyl]formamide

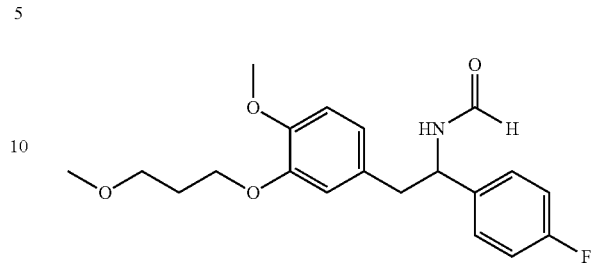

To a mixture of 1-(4-fluorophenyl)-2-[4-methoxy-3-(3-methoxypropoxy)phenyl]ethanamine (6.0 g, 18.0 mmol) in dioxane (80 mL) was added formic acid (4.14 g, 90.0 mmol). The mixture was heated under reflux for 48 hrs. After being cooled to rt, the mixture was concentrated under reduced pressure. The residue was diluted with DCM (100 mL), and the organic mixture was washed with water (50 mL) and brine (50 mL), dried over anhydrous $Na_2SO_4$ and concentrated under reduced pressure. The residue was purified by column chromatography to give N-[1-(4-fluorophenyl)-2-[4-methoxy-3-(3-methoxypropoxy)phenyl]ethyl]formamide (2.6 g) as a white solid.

Step 4: Preparation of 3-(4-fluorophenyl)-7-methoxy-6-(3-methoxypropoxy)-3,4-dihydroisoquinoline

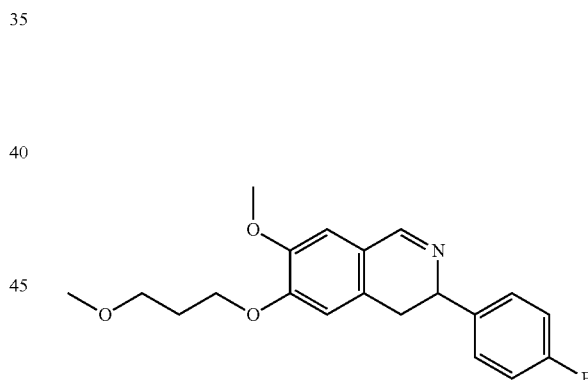

To a mixture of N-[1-(4-fluorophenyl)-2-[4-methoxy-3-(3-methoxypropoxy)phenyl]ethyl]formamide (1.0 g, 2.77 mmol) in DCM (10 mL) was added $POCl_3$ (636 mg, 4.16 mmol). The mixture was heated under reflux for 2 hrs. After being cooled to rt, the mixture was partitioned between ammonia water (20 mL) and DCM (100 mL). The organic layer was washed with water (30 mL) and brine (30 mL), dried over anhydrous $Na_2SO_4$ and concentrated under reduced pressure. The residue was purified by column chromatography to give 3-(4-fluorophenyl)-7-methoxy-6-(3-methoxypropoxy)-3,4-dihydroisoquinoline (650 mg) as a yellow oil.

Step 5: Preparation of ethyl 6-(4-fluorophenyl)-10-methoxy-9-(3-methoxypropoxy)-2-oxo-1,6,7,11b-tetrahydrobenzo[a]quinolizine-3-carboxylate

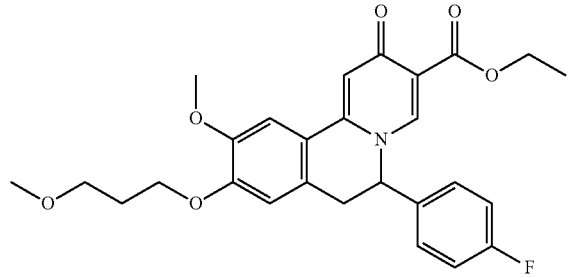 [SMILES: CCOC(=O)c1cn2c(cc1=O)-c1cc(OC)c(OCCCOC)cc1CC2c1ccc(F)cc1]

A mixture of 3-(4-fluorophenyl)-7-methoxy-6-(3-methoxypropoxy)-3,4-dihydroisoquinoline (650 mg, 1.89 mmol) and ethyl 2-(ethoxymethylene)-3-oxo-butanoate (1.06 g, 5.69 mmol) in EtOH (10 mL) was heated under reflux for 24 hrs. After being cooled to rt, the mixture was concentrated under reduced pressure to give crude ethyl 6-(4-fluorophenyl)-10-methoxy-9-(3-methoxypropoxy)-2-oxo-1,6,7,11b-tetrahydrobenzo[a]quinolizine-3-carboxylate (1.2 g), which was used directly in the next step without further purification.

Step 6: Preparation of ethyl 6-(4-fluorophenyl)-10-methoxy-9-(3-methoxypropoxy)-2-oxo-6,7-dihydrobenzo[a]quinolizine-3-carboxylate

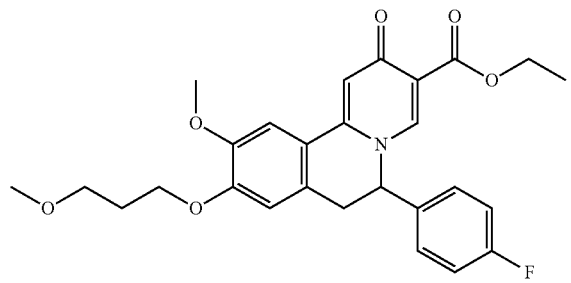 [SMILES: CCOC(=O)c1cn2c(cc1=O)-c1cc(OC)c(OCCCOC)cc1CC2c1ccc(F)cc1]

A mixture of ethyl 6-(4-fluorophenyl)-10-methoxy-9-(3-methoxypropoxy)-2-oxo-1,6,7,11 b-tetrahydrobenzo[a]quinolizine-3-carboxylate (crude 1.2 g) and p-chloranil (410 mg, 1.67 mmol) in DME (15 mL) was heated under reflux for 3 hrs. Then the mixture was filtered, and the filtrate was concentrated under reduced pressure. The residue was diluted with DCM. The organic mixture was washed with NaHCO₃ aqueous solution and brine, dried over anhydrous Na₂SO₄ and concentrated under reduced pressure to give crude ethyl 6-(4-fluorophenyl)-10-methoxy-9-(3-methoxypropoxy)-2-oxo-6,7-dihydrobenzo[a]quinolizine-3-carboxylate (1.4 g), which was used directly in the next step without further purification.

Step 7: Preparation of 6-(4-fluorophenyl)-10-methoxy-9-(3-methoxypropoxy)-2-oxo-6,7-dihydrobenzo[a]quinolizine-3-carboxylic Acid

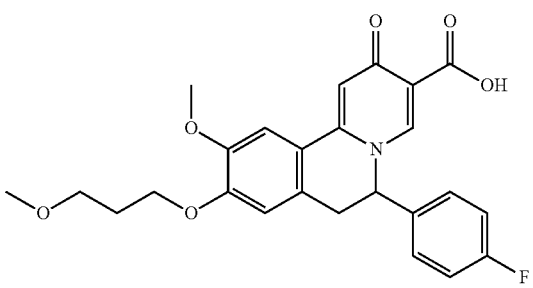 [SMILES: COCCCOc1cc2c(cc1OC)-c1cc(=O)c(C(=O)O)cn1C(c1ccc(F)cc1)C2]

To a mixture of ethyl 6-(4-fluorophenyl)-10-methoxy-9-(3-methoxypropoxy)-2-oxo-6,7-dihydrobenzo[a]quinolizine-3-carboxylate (crude 700 mg) in MeOH (7 mL) was added 2 M NaOH aqueous solution (0.8 mL). The mixture was stirred at 15° C. for 16 hrs, and then concentrated under reduced pressure. The residue was acidified with 1 M hydrochloric acid to pH=3, and extracted with DCM. The organic layer was dried over anhydrous Na₂SO₄ and concentrated under reduced pressure. The residue was treated with MeOH (5 mL), and then filtered. The filter cake was purified by prep-HPLC to give 6-(4-fluorophenyl)-10-methoxy-9-(3-methoxypropoxy)-2-oxo-6,7-dihydrobenzo[a]quinolizine-3-carboxylic acid (22 mg) as a white solid. $^1$H NMR (400 MHz, DMSO-d6): δ: 8.82 (s, 1H), 7.50-7.53 (m, 2H), 7.06-7.23 (m, 4H), 6.94 (s, 1H), 6.08 (s, 1H), 4.02 (t, 2H), 3.86 (s, 3H), 3.66-3.70 (m, 1H), 3.42-3.50 (m, 4H), 3.22 (s, 3H), 1.94-2.01 (m, 2H). MS obsd. (ESI⁺) [(M+H)⁺]: 454.

Example 10: 10-methoxy-9-(3-methoxypropoxy)-6-(o-tolyl)-2-oxo-6,7-dihydrobenzo[a]quinolizine-3-carboxylic Acid

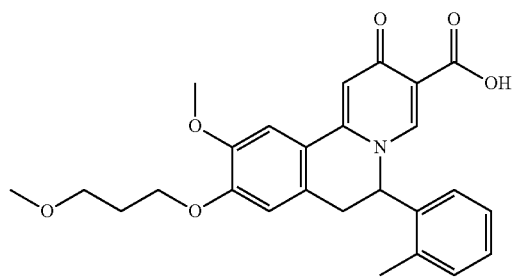 [SMILES: COCCCOc1cc2c(cc1OC)-c1cc(=O)c(C(=O)O)cn1C(c1ccccc1C)C2]

Step 1: Preparation of 2-[4-methoxy-3-(3-methoxypropoxy)phenyl]-1-(o-tolyl)ethanone

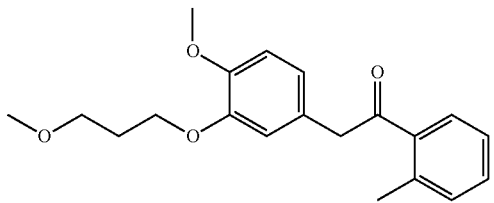 [SMILES: COCCCOc1cc(CC(=O)c2ccccc2C)ccc1OC]

A mixture of 4-bromo-1-methoxy-2-(3-methoxypropoxy)benzene (41.0 g, 155 mmol), 1-(o-tolyl)ethanone (17.5 g, 202 mmol), t-BuONa (27.0 g, 280 mmol), $Pd_2(dba)_3$ (11.4 g, 12.5 mmol) and Xantphos (3.61 g, 6.23 mmol) in THF (500 mL) was heated at 50° C. for 12 hrs. After being cooled to rt, the mixture was concentrated under reduced pressure. The residue was purified by column chromatography to give 2-[4-methoxy-3-(3-methoxypropoxy)phenyl]-1-(o-tolyl)ethanone (38.0 g) as a light yellow oil.

Step 2: Preparation of 2-[4-methoxy-3-(3-methoxypropoxy)phenyl]-1-(o-tolyl)ethanamine

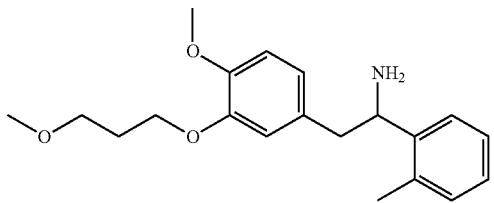 [SMILES: COCCCOc1cc(CC(N)c2ccccc2C)ccc1OC]

To a solution of 2-[4-methoxy-3-(3-methoxypropoxy)phenyl]-1-(o-tolyl)ethanone (10.5 g, 32 mmol) in MeOH (120 mL) was added $NH_4OAc$ (17.25 g, 224 mmol) at 24° C. After the mixture was stirred for 1 hr, to the mixture was added $NaBH_3CN$ (2.61 g, 2.61 mmol) at 0° C. The resulting mixture was heated under reflux for 12 hrs, then cooled to rt and concentrated under reduced pressure. The residue was partitioned between $H_2O$ (100 mL) and DCM (500 mL). The organic layer was washed with brine (100 mL), dried over anhydrous $Na_2SO_4$ and concentrated under reduced pressure to afford 2-[4-methoxy-3-(3-methoxypropoxy)phenyl]-1-(o-tolyl)ethanamine (11.0 g, crude) as yellow oil, which was used directly in next step without further purification.

Step 3: Preparation of N-[2-[4-methoxy-3-(3-methoxypropoxy)phenyl]-1-(o-tolyl)ethyl]formamide

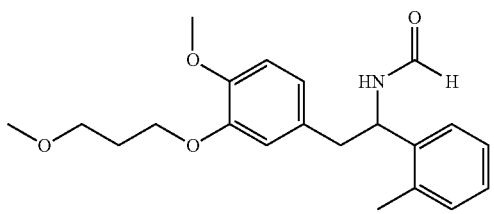 [SMILES: COCCCOc1cc(CC(NC=O)c2ccccc2C)ccc1OC]

To a solution of 2-[4-methoxy-3-(3-methoxypropoxy)phenyl]-1-(o-tolyl)ethanamine (11.0 g, 33.4 mmol) in dioxane (120 mL) was added formic acid (7.68 g, 147 mmol). The mixture was heated under reflux for 12 hrs. After being cooled to rt, the mixture was concentrated under reduced pressure. The residue was partitioned between $H_2O$ (100 mL) and DCM (500 mL). The organic layer was separated, washed with brine (100 mL), dried over anhydrous $Na_2SO_4$ and concentrated under reduced pressure. The residue was purified by column chromatography to afford N-[2-[4-methoxy-3-(3-methoxypropoxy)phenyl]-1-(o-tolyl)ethyl]formamide (5.0 g) as a light yellow solid.

Step 4: Preparation of 7-methoxy-6-(3-methoxypropoxy)-3-(o-tolyl)-3,4-dihydroisoquinoline

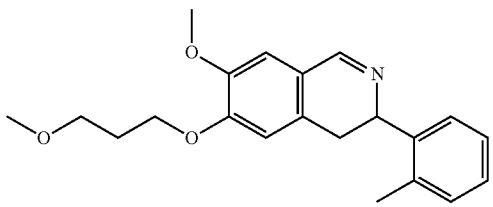 [SMILES: COCCCOc1cc2c(cc1OC)C=NC(c1ccccc1C)C2]

To a stirred solution of N-[2-[4-methoxy-3-(3-methoxypropoxy)phenyl]-1-(o-tolyl)ethyl]formamide (2.0 g, 5.6 mmol) in DCM (40 mL) was added $POCl_3$ (1.7 g, 11.1 mmol). The reaction mixture was stirred at 30° C. for 8 hrs, and then poured into a stirred mixture of DCM and ammonia water. The organic layer was separated, washed with brine, dried over anhydrous $Na_2SO_4$ and concentrated under reduced pressure. The residue was purified by the flash column chromatography to afford 7-methoxy-6-(3-methoxypropoxy)-3-(o-tolyl)-3,4-dihydroisoquinoline (1.12 g) as a yellow oil.

Step 5: Preparation of ethyl 10-methoxy-9-(3-methoxypropoxy)-6-(o-tolyl)-2-oxo-1,6,7,11b-tetrahydrobenzo[a]quinolizine-3-carboxylate

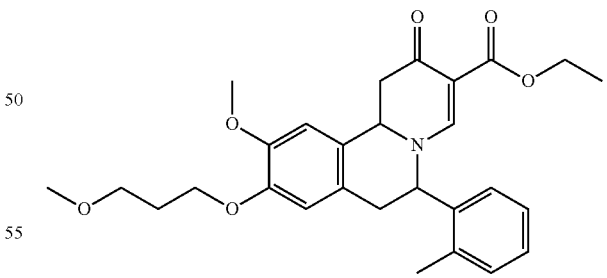

A mixture of 7-methoxy-6-(3-methoxypropoxy)-3-(o-tolyl)-3,4-dihydroisoquinoline (500 mg, 1.47 mmol) and ethyl 2-(ethoxymethylene)-3-oxo-butanoate (82 mg, 4.42 mmol) in EtOH (10 mL) was refluxed for 72 hrs. After being cooled to rt, the mixture was concentrated under reduced pressure to give crude ethyl 10-methoxy-9-(3-methoxypropoxy)-6-(o-tolyl)-2-oxo-1,6,7,11b-tetrahydrobenzo[a]quinolizine-3-carboxylate (750 mg), which was used directly in the next step without further purification.

Step 6: Preparation of ethyl 10-methoxy-9-(3-methoxypropoxy)-6-(o-tolyl)-2-oxo-6,7-dihydrobenzo[a]quinolizine-3-carboxylate

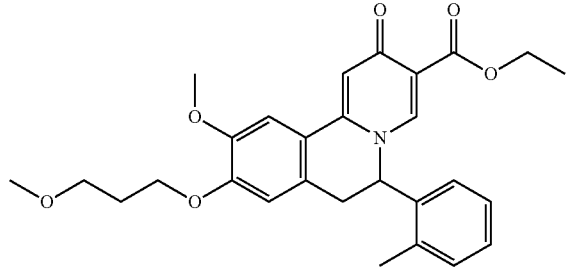 [SMILES: CCOC(=O)c1cn2c(cc1=O)-c1cc(OC)c(OCCCOC)cc1CC2c1ccccc1C]

A mixture of ethyl 10-methoxy-9-(3-methoxypropoxy)-6-(o-tolyl)-2-oxo-1,6,7,11b-tetrahydrobenzo[a]quinolizine-3-carboxylate (750 mg, 1.56 mmol) and p-chloranil (385 mg, 1.356 mmol) in DME (10 mL) was heated at 80° C. for 3 hrs. Then the reaction mixture was filtered. The filtrate was concentrated under reduced pressure to give crude ethyl 10-methoxy-9-(3-methoxypropoxy)-6-(o-tolyl)-2-oxo-6,7-dihydrobenzo[a]quinolizine-3-carboxylate (703 mg), which was used directly in the next step without further purification.

Step 7: Preparation of 10-methoxy-9-(3-methoxypropoxy)-6-(o-tolyl)-2-oxo-6,7-dihydrobenzo[a]quinolizine-3-carboxylic Acid

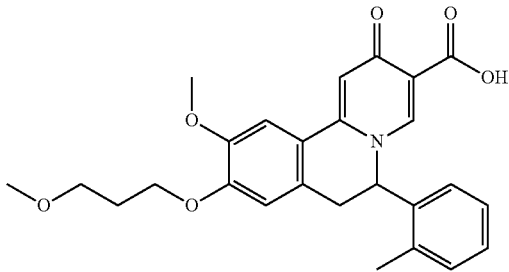 [SMILES: COCCCOc1cc2c(cc1OC)-c1cc(=O)c(C(=O)O)cn1C(c1ccccc1C)C2]

A mixture of crude ethyl 10-methoxy-9-(3-methoxypropoxy)-6-(o-tolyl)-2-oxo-6,7-dihydrobenzo[a]quinolizine-3-carboxylate (703 mg, 1.47 mmol) and NaOH (235 mg) in a mixture solvent of H$_2$O (3 mL) and MeOH (10 mL) was heated at 30° C. for 16 hrs. The mixture was concentrated under reduced pressure. The residue was diluted with H$_2$O and acidified with 1 M hydrochloric acid to pH=3-4. The resulting mixture was filtered. The filter cake was recrystallized with MeOH, and then purified by prep-HPLC to afford 10-methoxy-9-(3-methoxypropoxy)-6-(o-tolyl)-2-oxo-6,7-dihydrobenzo[a]quinolizine-3-carboxylic acid (51 mg) as a white solid. $^1$H NMR (400 MHz, MeOD): δ 1.95-2.07 (m, 2H), 2.53 (s, 3H), 3.29 (s, 3H), 3.35 (d, 1H), 3.53 (td, 2H), 3.62 (dd, 1H), 3.95 (s, 3H), 4.02-4.11 (m, 2H), 4.61 (s, 1H), 6.06 (br. s., 1H), 6.56 (d, 1H), 6.82 (s, 1H), 7.00 (t, 1H), 7.18 (t, 1H), 7.24-7.31 (m, 1H), 7.42 (s, 1H), 7.51 (s, 1H), 8.54 (s, 1H). MS obsd. (ESI$^+$) [(M+H)$^+$]: 450.

Example 11: 9-methoxy-8-methyl-2-oxo-6-(2-thienyl)-6,7-dihydrobenzo[a]quinolizine-3-carboxylic Acid

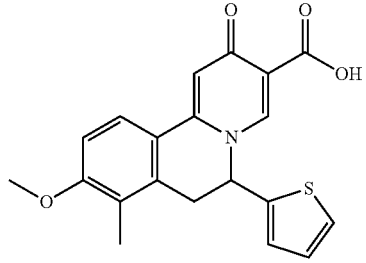 [SMILES: COc1ccc2c(c1C)CC(c1cccs1)n1cc(C(=O)O)c(=O)cc1-2]

Step 1: Preparation of 4-bromo-1-methoxy-2-(3-methoxypropoxy)benzene

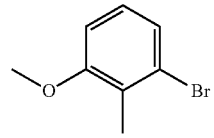

To a solution of 3-bromo-2-methyl-phenol (11.4 g, 60.95 mmol) in DMF (150 mL) was added K$_2$CO$_3$ (25.3 g, 183 mmol) and iodomethane (26.0 g, 183 mmol). The mixture was stirred at 25° C. for 12 hrs, and then concentrated under reduced pressure. The residue was diluted with EtOAc (200 mL). The organic mixture was washed with water and brine, dried over anhydrous Na$_2$SO$_4$ and concentrated under reduced pressure. The residue was purified by column chromatography to give 4-bromo-1-methoxy-2-(3-methoxypropoxy)benzene (11.0 g) as a colorless oil.

Step 2: Preparation of 2-(3-methoxy-2-methyl-phenyl)-1-(2-thienyl)ethanone

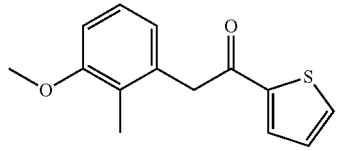 [SMILES: COc1cccc(CC(=O)c2cccs2)c1C]

To a solution of 4-bromo-1-methoxy-2-(3-methoxypropoxy)benzene (11.0 g, 54.7 mmol) in THF (120 mL) was added 1-(2-thienyl)ethanone (8.97 g, 71.1 mmol), t-BuONa (7.89 g, 82.1 mmol), Pd$_2$(dba)$_3$ (1 g, 1.09 mmol) and Xantphos (633 mg, 1.09 mmol) under nitrogen atmosphere. The mixture was heated at 50° C. for 4 hrs, and then concentrated under reduced pressure. The residue was diluted with DCM (600 mL). The resulting organic mixture was washed with water and brine, dried over anhydrous Na$_2$SO$_4$ and concentrated under reduced pressure. The residue was purified by column chromatography to afford 2-(3-methoxy-2-methyl-phenyl)-1-(2-thienyl)ethanone (13.0 g) as a brown oil.

Step 3: Preparation of 2-(3-methoxy-2-methyl-phenyl)-1-(2-thienyl)ethanamine

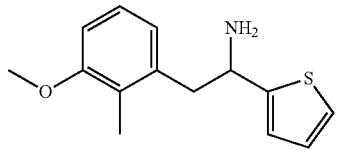 [SMILES: COc1cccc(CC(N)c2cccs2)c1C]

To a solution of 2-(3-methoxy-2-methyl-phenyl)-1-(2-thienyl)ethanone (13.0 g, 52.8 mmol) in MeOH (130 mL) was added NH$_4$OAc (40.7 g, 528 mmol) at 70° C. The mixture was heated at 70° C. for 1 hr, and then cooled to 0° C. To this mixture was added NaBH$_3$CN (6.63 g, 105 mmol) at 0° C. Then the resulting mixture was heated at 80° C. for 12 hrs. After being cooled to rt, the mixture was concentrated under reduced pressure to remove most of MeOH. The residue was partitioned between H$_2$O (100 mL) and DCM (500 mL). The organic layer was separated, washed with brine (100 mL), dried over anhydrous Na$_2$SO$_4$ and concentrated under reduced pressure. The residue was purified by column chromatography to afford 2-(3-methoxy-2-methyl-phenyl)-1-(2-thienyl)ethanamine (6.4 g, crude) as a yellow solid.

Step 4: Preparation of N-[2-(3-methoxy-2-methyl-phenyl)-1-(2-thienyl)ethyl]formamide

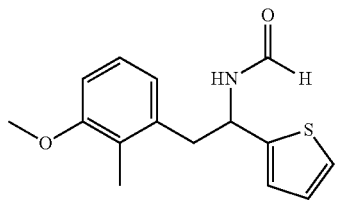 [SMILES: COc1cccc(CC(NC=O)c2cccs2)c1C]

To a solution of 2-(3-methoxy-2-methyl-phenyl)-1-(2-thienyl)ethanamine (5.4 g, 21.8 mmol) in dioxane (60 mL) was added formic acid (10.05 g, 218 mmol). The mixture was heated at 120° C. for 12 hrs. After being cooled to rt, the mixture was partitioned between H$_2$O (200 mL) and DCM (600 mL). The organic layer was washed with brine (200 mL), dried over anhydrous Na$_2$SO$_4$ and concentrated under reduced pressure. The residue was purified by column chromatography to afford N-[2-(3-methoxy-2-methyl-phenyl)-1-(2-thienyl)ethyl]formamide (3.4 g) as a brown oil.

Step 5: Preparation of 6-methoxy-5-methyl-3-(2-thienyl)-3,4-dihydroisoquinoline

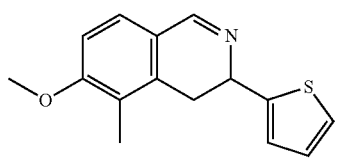 [SMILES: COc1ccc2c(c1C)CC(c1cccs1)N=C2]

To a mixture of N-[2-(3-methoxy-2-methyl-phenyl)-1-(2-thienyl)ethyl]formamide (2.9 g, 10.53 mmol) in dry DCM (40 mL) was added POCl$_3$ (5.41 g, 35.3 mmol) drop-wise at 0° C. Then the mixture was heated under reflux for 12 hrs. After being cooled to rt, the mixture was poured into a solution of ammonia water (30 mL) in H$_2$O (100 mL). Then the mixture was extracted with DCM (200 mL). The organic layer was washed with brine (100 mL), dried over anhydrous Na$_2$SO$_4$ and concentrated under reduced pressure to afford crude 6-methoxy-5-methyl-3-(2-thienyl)-3,4-dihydroisoquinoline (4.0 g) as a yellow oil, which was used directly in the next step without further purification.

Step 6: Preparation of ethyl 9-methoxy-8-methyl-2-oxo-6-(2-thienyl)-1,6,7,11b-tetrahydrobenzo[a]quinolizine-3-carboxylate

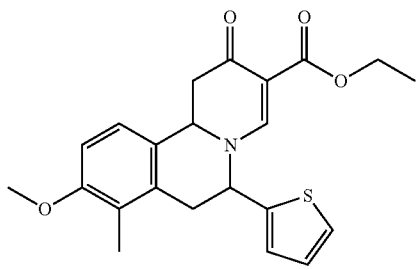 [SMILES: CCOC(=O)C1=CN2C(c3cccs3)Cc3c(ccc(OC)c3C)C2CC1=O]

A solution of 6-methoxy-5-methyl-3-(2-thienyl)-3,4-dihydroisoquinoline (2.0 g, 7.77 mmol) and ethyl 2-(ethoxymethylene)-3-oxo-butanoate (4.34 g, 23.3 mmol) in EtOH (30 mL) was heated at 100° C. for 48 hrs. After being cooled to rt, the mixture was concentrated under reduced pressure to give crude ethyl 9-methoxy-8-methyl-2-oxo-6-(2-thienyl)-1,6,7,11b-tetrahydrobenzo[a]quinolizine-3-carboxylate, which was used directly in the next step without further purification.

Step 7: Preparation of ethyl 9-methoxy-8-methyl-2-oxo-6-(2-thienyl)-6,7-dihydrobenzo[a]quinolizine-3-carboxylate

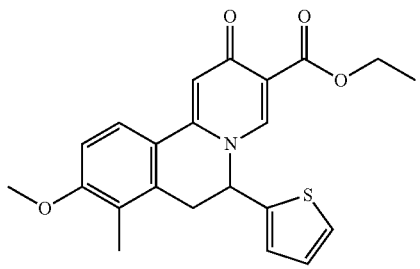 [SMILES: CCOC(=O)c1cn2c(cc1=O)-c1ccc(OC)c(C)c1CC2c1cccs1]

A solution of ethyl 9-methoxy-8-methyl-2-oxo-6-(2-thienyl)-1,6,7,11b-tetrahydrobenzo[a]quinolizine-3-carboxylate (3.0 g, 7.55 mmol) and p-chloranil (1.3 g, 5.28 mmol) in DME (30 mL) was heated at 80° C. for 3 hrs under nitrogen atmosphere. After being cooled to rt, the mixture was filtered. The filter cake was dried under reduced pressure to give ethyl 9-methoxy-8-methyl-2-oxo-6-(2-thienyl)-6,7-dihydrobenzo[a]quinolizine-3-carboxylate (1.3 g) as a yellow solid.

Step 8: Preparation of 9-methoxy-8-methyl-2-oxo-6-(2-thienyl)-6,7-dihydrobenzo[a]quinolizine-3-carboxylic Acid

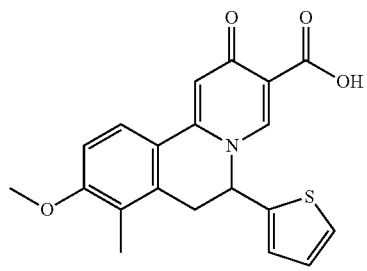 [SMILES: COc1ccc2c(c1C)CC(c1cccs1)n1cc(C(=O)O)c(=O)cc1-2]

To a solution of ethyl 9-methoxy-8-methyl-2-oxo-6-(2-thienyl)-6,7-dihydrobenzo[a]quinolizine-3-carboxylate (200 mg, 506 μmol) in MeOH (2 mL) was added 2 M NaOH aqueous solution (0.76 mL, 1.5 mmol). The mixture was stirred at 25° C. for 12 hrs, then diluted with H$_2$O (20 mL) and acidified with 1 M hydrochloric acid to pH=3. The mixture was extracted with DCM (100 mL). The organic layer was washed with brine (50 mL), dried over anhydrous Na$_2$SO$_4$ and concentrated under reduced pressure. The residue was purified by prep-HPLC to afford 9-methoxy-8-methyl-2-oxo-6-(2-thienyl)-6,7-dihydrobenzo[a]quinolizine-3-carboxylic acid (12 mg) as a yellow solid. $^1$H NMR (400 MHz, CDCl$_3$): δ: 2.22 (s, 3H), 3.37-3.69 (m, 2H), 3.93 (s, 3H), 5.73 (br. s., 1H), 6.81 (d, 1H), 6.85-6.91 (m, 1H), 6.95 (d, 1H), 7.12 (s, 1H), 7.18 (d, 1H), 7.66 (d, 1H), 8.59 (s, 1H). MS obsd. (ESI$^+$) [(M+H)$^+$]: 368.

Example 12: 9-benzyloxy-10-methoxy-2-oxo-6-(2-thienyl)-6,7-dihydrobenzo[a]quinolizine-3-carboxylic Acid

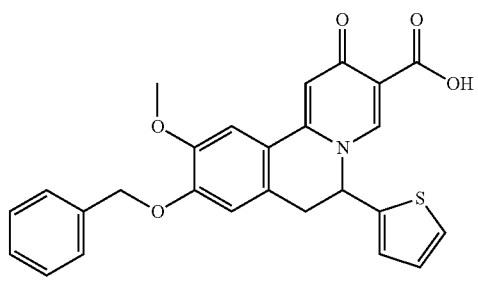 [SMILES: COc1cc2c(cc1OCc1ccccc1)CC(c1cccs1)n1cc(C(=O)O)c(=O)cc1-2]

Step 1: Preparation of 2-benzyloxy-4-bromo-1-methoxy-benzene

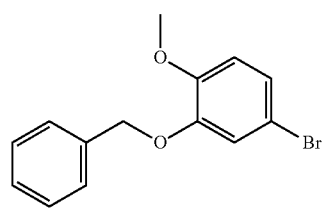 [SMILES: COc1ccc(Br)cc1OCc1ccccc1]

A mixture of 5-bromo-2-methoxy-phenol (100.0 g, 0.49 mol), K$_2$CO$_3$ (102.0 g, 0.74 mol) and bromomethylbenzene (101.0 g, 0.59 mol) in acetone (1.5 L) was heated under reflux for 16 hrs. After being cooled to rt, the mixture was filtered. The filtrate was concentrated under reduced pressure. The residue was purified by trituration (PE, 300 mL) to give 2-benzyloxy-4-bromo-1-methoxy-benzene (140.0 g) as a white solid.

Step 2: Preparation of 2-(3-benzyloxy-4-methoxy-phenyl)-1-(2-thienyl)ethanone

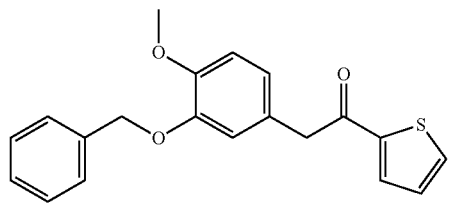 [SMILES: COc1ccc(CC(=O)c2cccs2)cc1OCc1ccccc1]

A mixture of 2-benzyloxy-4-bromo-1-methoxy-benzene (50.0 g, 0.17 mol), 1-(2-thienyl)ethanone (32.3 g, 0.26 mol), t-BuONa (29.5 g, 0.31 mol), Xantphos (4.9 g, 8.53 mmol) and Pd$_2$(dba)$_3$ (3.9 g, 4.26 mmol) in THF (800 ml) was heated at 60° C. for 5 hrs under nitrogen atmosphere. After being cooled to rt, the mixture was filtered. The filtrate was concentrated under reduced pressure. The residue was purified by the flash column chromatography to afford 2-(3-benzyloxy-4-methoxy-phenyl)-1-(2-thienyl)ethanone (31.0 g) as a light yellow solid.

Step 3: Preparation of 2-(3-benzyloxy-4-methoxy-phenyl)-1-(2-thienyl)ethanamine

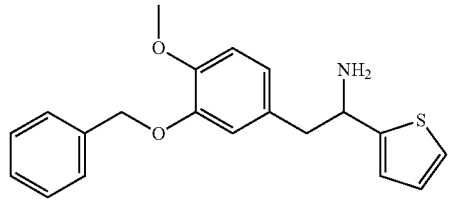 [SMILES: COc1ccc(CC(N)c2cccs2)cc1OCc1ccccc1]

A mixture of 2-(3-benzyloxy-4-methoxy-phenyl)-1-(2-thienyl)ethanone (31.0 g, 0.092 mol) and NH$_4$OAc (49.4 g, 0.64 mol) in MeOH (500 ml) was refluxed for 6 hrs. The resulting mixture was cooled to rt, and then to the mixture was added NaBH$_3$CN (8.6 g, 0.14 mol) portion wise. The resulting mixture was refluxed for 16 hrs. After being cooled to rt, the resulting reaction mixture was concentrated under reduced pressure, and the residue was partitioned between EtOAc and H$_2$O. The organic layer was washed with brine, dried over anhydrous Na$_2$SO$_4$ and concentrated under reduced pressure to give 2-(3-benzyloxy-4-methoxy-phenyl)-1-(2-thienyl)ethanamine (38.0 g), which was used directly in the next step without further purification.

Step 4: Preparation of N-[2-(3-benzyloxy-4-methoxy-phenyl)-1-(2-thienyl)ethyl]formamide

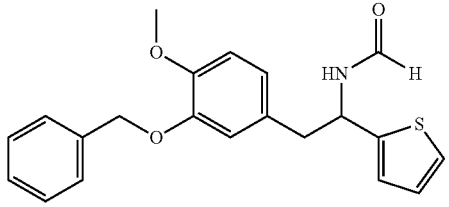 [SMILES: COc1ccc(CC(NC=O)c2cccs2)cc1OCc1ccccc1]

A mixture of 2-(3-benzyloxy-4-methoxy-phenyl)-1-(2-thienyl)ethanamine (85.0 g, 0.25 mol) and formic acid (57.6 g, 1.25 mol) in 1,4-dioxane (850 ml) was refluxed for 48 hrs. The resulting mixture was cooled to rt and concentrated under reduced pressure. The residue was partitioned between EtOAc and saturated NaHCO₃ aqueous solution. The organic layer was separated, washed with brine, dried over anhydrous Na₂SO₄ and concentrated under reduced pressure. The residue was purified by column chromatography to afford N-[2-(3-benzyloxy-4-methoxy-phenyl)-1-(2-thienyl)ethyl]formamide (41.5 g) as a yellow oil.

Step 5: Preparation of 6-benzyloxy-7-methoxy-3-(2-thienyl)-3,4-dihydroisoquinoline

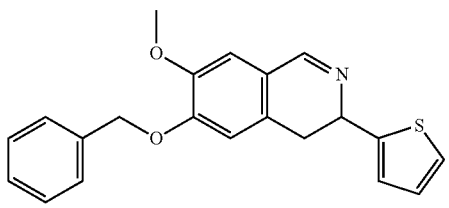 [SMILES: COc1cc2c(cc1OCc1ccccc1)CC(c1cccs1)N=C2]

To a stirred solution of N-[2-(3-benzyloxy-4-methoxy-phenyl)-1-(2-thienyl)ethyl]formamide (35.0 g, 0.095 mol) in DCM (400 ml) was added POCl₃ (31.59 g, 0.21 mol) at rt. The mixture was heated at 50° C. for 1 hr. After being cooled to rt, the mixture was poured into a stirred mixture of ammonia water and DCM. The organic phase was separated, washed with brine, dried over anhydrous Na₂SO₄ and concentrated under reduced pressure. The residue was purified by the flash column chromatography to afford 6-benzyloxy-7-methoxy-3-(2-thienyl)-3,4-dihydroisoquinoline (25.3 g) as a light yellow solid.

Step 6: Preparation of ethyl 9-benzyloxy-10-methoxy-2-oxo-6-(2-thienyl)-1,6,7,11b-tetrahydrobenzo[a]quinolizine-3-carboxylate

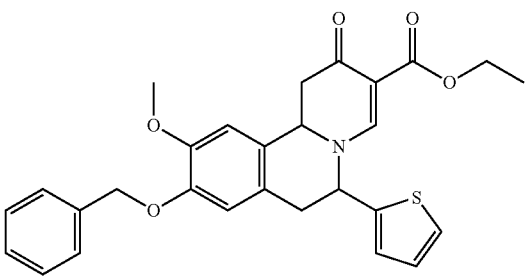

A mixture of 6-benzyloxy-7-methoxy-3-(2-thienyl)-3,4-dihydroisoquinoline (17.2 g, 0.049 mol) and ethyl 2-(ethoxymethylene)-3-oxo-butanoate (27.5 g, 0.15 mol) in EtOH (200 ml) was heated under reflux for 72 hrs. After being cooled to rt, the mixture was concentrated under reduced pressure to give crude ethyl 9-benzyloxy-10-methoxy-2-oxo-6-(2-thienyl)-1,6,7,11b-tetrahydrobenzo[a]quinolizine-3-carboxylate (24.0 g), which was used directly in the next step without further purification.

Step 7: Preparation of ethyl 9-benzyloxy-10-methoxy-2-oxo-6-(2-thienyl)-6,7-dihydrobenzo[a]quinolizine-3-carboxylate

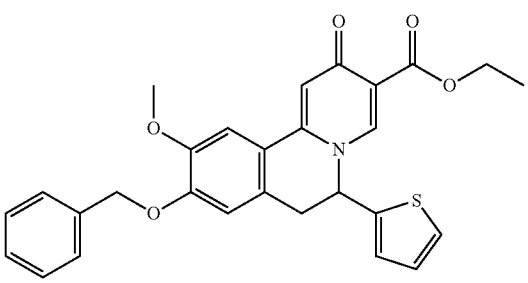 [SMILES: CCOC(=O)c1cn2c(cc1=O)-c1cc(OC)c(OCc3ccccc3)cc1CC2c1cccs1]

A mixture of ethyl 9-benzyloxy-10-methoxy-2-oxo-6-(2-thienyl)-1,6,7,11b-tetrahydrobenzo[a]quinolizine-3-carboxylate (14.6 g, 0.029 mol) and p-chloranil (7.3 g, 0.029 mol) in DME (150 ml) was heated at 80° C. for 3 hrs. The mixture was cooled to rt and filtered. The filter cake was dried to afford ethyl 9-benzyloxy-10-methoxy-2-oxo-6-(2-thienyl)-6,7-dihydrobenzo[a]quinolizine-3-carboxylate (7.0 g, yield: 48%) as a light yellow solid.

Step 8: Preparation of 9-benzyloxy-10-methoxy-2-oxo-6-(2-thienyl)-6,7-dihydrobenzo[a]quinolizine-3-carboxylic Acid

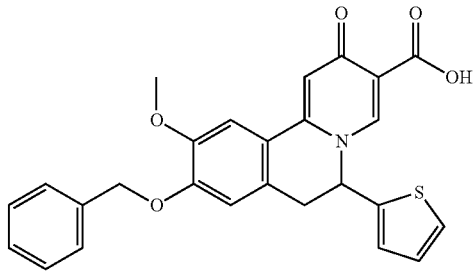 [SMILES: COc1cc2c(cc1OCc1ccccc1)CC(c1cccs1)n1cc(C(=O)O)c(=O)cc1-2]

A mixture of ethyl 9-benzyloxy-10-methoxy-2-oxo-6-(2-thienyl)-6,7-dihydrobenzo[a]quinolizine-3-carboxylate (100 mg, 0.21 mmol) and NaOH (16 mg) in a mixture solvent of H₂O (0.2 mL) and THF (5 mL) was stirred at room temperature for 16 hrs. The mixture was concentrated under reduced pressure. The residue was diluted with H₂O and acidified with 1 M hydrochloric acid to pH=2-3. Then the mixture was filtered. The filter cake was dried under reduced pressure to afford 9-benzyloxy-10-methoxy-2-oxo-6-(2-thienyl)-6,7-dihydrobenzo[a]quinolizine-3-carboxylic acid (54 mg) as a yellow solid. ¹H NMR (400 MHz, DMSO-d6) δ: δ 3.30-3.39 (m, 1H), 3.73 (dd, 1H), 3.88 (s, 3H), 5.16 (s, 2H), 6.35 (d, 1H), 6.87-6.94 (m, 1H), 7.02 (d, 1H), 7.20 (s, 1H), 7.32-7.43 (m, 4H), 7.44-7.50 (m, 2H), 7.54 (d, 2H), 8.99 (s, 1H). MS obsd. (ESI⁺) [(M+H)⁺]: 460.

Example 13: 9,10-dimethoxy-2-oxo-6-(2-thienyl)-6,7-dihydrobenzo[a]quinolizine-3-carboxylic Acid

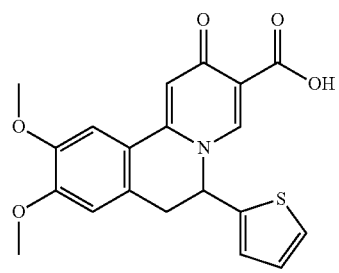 [SMILES: COc1cc2c(cc1OC)-c1cc(=O)c(C(=O)O)cn1C(c1cccs1)C2]

Step 1: Preparation of ethyl 9-hydroxy-10-methoxy-2-oxo-6-(2-thienyl)-6,7-dihydrobenzo[a]quinolizine-3-carboxylate

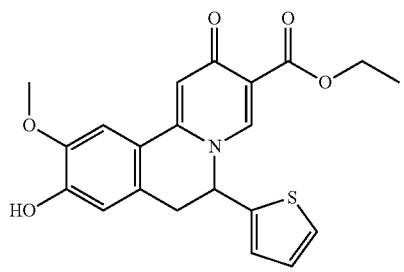 [SMILES: CCOC(=O)c1cn2c(cc1=O)-c1cc(OC)c(O)cc1CC2c1cccs1]

A solution of ethyl 9-benzyloxy-10-methoxy-2-oxo-6-(2-thienyl)-6,7-dihydrobenzo[a]quinolizine-3-carboxylate (5.0 g, 0.01 mol, from step 7 of Example 12) and thioanisole (13.66 g, 0.11 mmol) in TFA (50 mL) was stirred at room temperature for 16 hrs. The resulting mixture was partitioned between DCM and H₂O. The organic layer was separated, washed with saturated NaHCO₃ aqueous solution and brine, dried over anhydrous Na₂SO₄ and concentrated under reduced pressure. The residue was recrystallized from DCM/hexane to afford ethyl 9-hydroxy-10-methoxy-2-oxo-6-(2-thienyl)-6,7-dihydrobenzo[a]quinolizine-3-carboxylate (3.50 g) as a yellow solid.

Step 2: Preparation of ethyl 9,10-dimethoxy-2-oxo-6-(2-thienyl)-6,7-dihydrobenzo[a]quinolizine-3-carboxylate

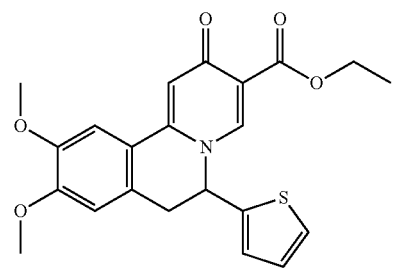 [SMILES: CCOC(=O)c1cn2c(cc1=O)-c1cc(OC)c(OC)cc1CC2c1cccs1]

A mixture of ethyl 9-hydroxy-10-methoxy-2-oxo-6-(2-thienyl)-6,7-dihydrobenzo[a]quinolizine-3-carboxylate (210 mg, 0.53 mmol), K₂CO₃ (132 mg, 0.95 mmol) and iodomethane (113 mg, 0.79 mmol) in acetone (5 mL) was heated at 50° C. for 16 hrs. The mixture was concentrated under reduced pressure and the residue was partitioned between EtOAc and H₂O. The organic layer was separated, dried over anhydrous Na₂SO₄ and concentrated under reduced pressure. The residue was recrystallized from a mixture solvent (PE:EA=1:1) to afford ethyl 9,10-dimethoxy-2-oxo-6-(2-thienyl)-6,7-dihydrobenzo[a]quinolizine-3-carboxylate (200 mg) as a light yellow solid.

Step 3: Preparation of 9,10-dimethoxy-2-oxo-6-(2-thienyl)-6,7-dihydrobenzo[a]quinolizine-3-carboxylic Acid

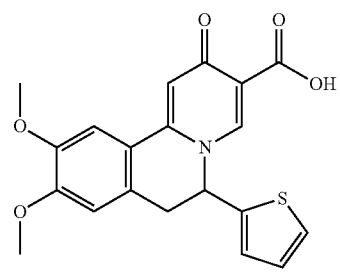 [SMILES: COc1cc2c(cc1OC)-c1cc(=O)c(C(=O)O)cn1C(c1cccs1)C2]

A mixture of ethyl 9,10-dimethoxy-2-oxo-6-(2-thienyl)-6,7-dihydrobenzo[a]quinolizine-3-carboxylate (100 mg, 0.24 mmol) and NaOH (20 mg) in MeOH (2 mL) and H₂O (0.2 mL) was stirred at room temperature for 16 hrs. The resulting mixture was concentrated under reduced pressure. The residue was diluted with H₂O and acidified by 1 M hydrochloric acid to pH=2-3. The mixture was filtered. The filter cake was dried under reduced pressure to afford 9,10-dimethoxy-2-oxo-6-(2-thienyl)-6,7-dihydrobenzo[a]quinolizine-3-carboxylic acid (46 mg) as a white solid. $^1$H NMR (400 MHz, DMSO-d6) δ: 3.37-3.39 (m, 1H), 3.73 (dd, 1H), 3.85 (d, 6H), 6.35 (d, 1H), 6.90 (t, 1H), 6.99-7.12 (m, 2H), 7.36 (d, 1H), 7.51 (d, 2H), 8.98 (s, 1H). MS obsd. (ESI$^+$) [(M+H)$^+$]: 384.

Example 14: 9-isobutoxy-10-methoxy-2-oxo-6-(2-thienyl)-6,7-dihydrobenzo[a]quinolizine-3-carboxylic Acid

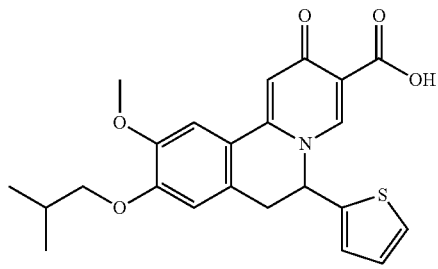 [SMILES: COc1cc2c(cc1OCC(C)C)CC(c1cccs1)n1cc(C(=O)O)c(=O)cc1-2]

Step 1: Preparation of ethyl 9-isobutoxy-10-methoxy-2-oxo-6-(2-thienyl)-6,7-dihydrobenzo[a]quinolizine-3-carboxylate

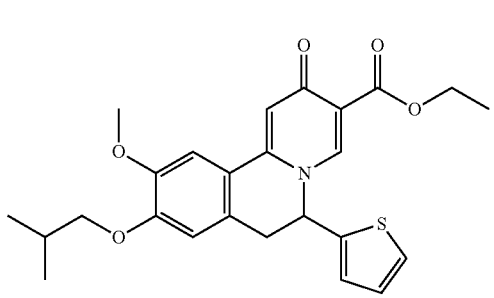 [SMILES: CCOC(=O)c1cn2c(cc1=O)-c1cc(OC)c(OCC(C)C)cc1CC2c1cccs1]

A mixture of ethyl 9-hydroxy-10-methoxy-2-oxo-6-(2-thienyl)-6,7-dihydrobenzo[a]quinolizine-3-carboxylate (150 mg, 0.38 mmol), 1-bromo-2-methyl-propane (78 mg, 0.57 mmol) and K$_2$CO$_3$ (78 mg, 0.57 mmol) in DMF (5 ml) was heated at 50° C. for 16 hrs. The mixture was partitioned between H$_2$O and DCM. The organic layer was separated, washed with brine, dried over anhydrous Na$_2$SO$_4$ and concentrated under reduced pressure. The residue was recrystallized from PE/EtOAc to afford ethyl 9-isobutoxy-10-methoxy-2-oxo-6-(2-thienyl)-6,7-dihydrobenzo[a]quinolizine-3-carboxylate (110 mg) as a light yellow solid.

Step 2: Preparation of 9-isobutoxy-10-methoxy-2-oxo-6-(2-thienyl)-6,7-dihydrobenzo[a]quinolizine-3-carboxylic Acid

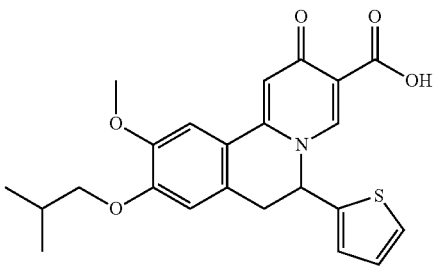 [SMILES: COc1cc2c(cc1OCC(C)C)CC(c1cccs1)n1cc(C(=O)O)c(=O)cc1-2]

A mixture of ethyl 9-isobutoxy-10-methoxy-2-oxo-6-(2-thienyl)-6,7-dihydrobenzo[a]quinolizine-3-carboxylate (80 mg, 0.18 mmol) and NaOH (14 mg) in MeOH (2 mL) and H$_2$O (0.2 mL) was stirred at room temperature for 16 hrs. The mixture was concentrated under reduced pressure. The residue was diluted with H$_2$O and acidified with 1 M hydrochloric acid to pH=2-3. The resulting mixture was filtered. The filter cake was dried under reduced pressure to afford 9-isobutoxy-10-methoxy-2-oxo-6-(2-thienyl)-6,7-dihydrobenzo[a]quinolizine-3-carboxylic acid (38 mg) as a white solid. $^1$H NMR (400 MHz, DMSO-d6) δ: 0.98 (d, 6H), 1.98-2.12 (m, 1H), 3.37 (br. s., 1H), 3.70 (dd, 1H), 3.80 (d, 2H), 3.88 (s, 3H), 6.27-6.39 (m, 1H), 6.88-6.93 (m, 1H), 7.02 (d, 1H), 7.07 (s, 1H), 7.36 (d, 1H), 7.50 (d, 2H), 8.98 (s, 1H). MS obsd. (ESI$^+$) [(M+H)$^+$]: 426.

Example 15: 9-(cyclopropylmethoxy)-10-methoxy-2-oxo-6-(2-thienyl)-6,7-dihydrobenzo[a]quinolizine-3-carboxylic Acid

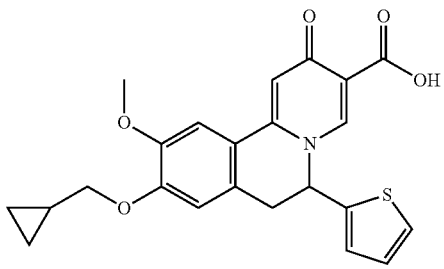 [SMILES: COc1cc2c(cc1OCC1CC1)CC(c1cccs1)n1cc(C(=O)O)c(=O)cc1-2]

Step 1: Preparation of ethyl 9-(cyclopropylmethoxy)-10-methoxy-2-oxo-6-(2-thienyl)-6,7-dihydrobenzo[a]quinolizine-3-carboxylate

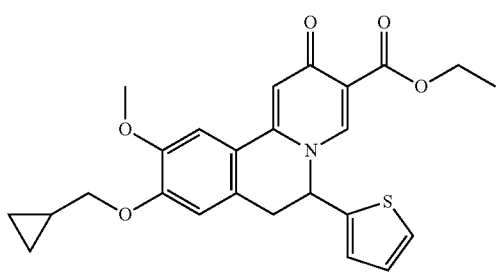 [SMILES: CCOC(=O)c1cn2c(cc1=O)-c1cc(OC)c(OCC3CC3)cc1CC2c1cccs1]

A mixture of ethyl 9-hydroxy-10-methoxy-2-oxo-6-(2-thienyl)-6,7-dihydrobenzo[a]quinolizine-3-carboxylate (150 mg, 0.38 mmol), bromomethylcyclopropane (76 mg, 0.57 mmol) and K₂CO₃ (78 mg, 0.57 mmol) in DMF (5 ml) was stirred at room temperature for 16 hrs. The resulting mixture was partitioned between H₂O and DCM. The organic layer was washed with brine, dried over anhydrous Na₂SO₄ and concentrated under reduced pressure. The residue was recrystallized from PE/EA to afford ethyl 9-(cyclopropylmethoxy)-10-methoxy-2-oxo-6-(2-thienyl)-6,7-dihydrobenzo[a]quinolizine-3-carboxylate (140 mg) as a light yellow solid.

Step 2: Preparation of 9-(cyclopropylmethoxy)-10-methoxy-2-oxo-6-(2-thienyl)-6,7-dihydrobenzo[a]quinolizine-3-carboxylic Acid

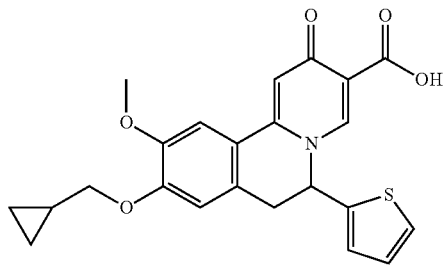 [SMILES: COc1cc2c(cc1OCC1CC1)CC(c1cccs1)n1cc(C(=O)O)c(=O)cc1-2]

A mixture of ethyl 9-(cyclopropylmethoxy)-10-methoxy-2-oxo-6-(2-thienyl)-6,7-dihydrobenzo[a]quinolizine-3-carboxylate (70 mg, 0.16 mmol) and NaOH (12 mg) in MeOH (2 mL) and H₂O (0.1 mL) was stirred at room temperature for 16 hrs. The resulting mixture was concentrated under reduced pressure. The residue was diluted with H₂O and acidified with 1 M hydrochloric acid to pH=2-3. The mixture was filtered and the filter cake was dried under reduced pressure to afford 9-(cyclopropylmethoxy)-10-methoxy-2-oxo-6-(2-thienyl)-6,7-dihydrobenzo[a]quinolizine-3-carboxylic acid. $^1$H NMR (400 MHz, DMSO-d6) δ: 0.26-0.39 (m, 2H), 0.53-0.64 (m, 2H), 1.17-1.33 (m, 1H), 3.31 (s, 1H), 3.70 (dd, 1H), 3.81-3.95 (m, 5H), 6.34 (d, 1H), 6.90 (dd, 1H), 6.98-7.07 (m, 2H), 7.35 (dd, 1H), 7.51 (d, 2H), 8.98 (s, 1H). MS obsd. (ESI⁺) [(M+H)⁺]: 424.

Example 16: 10-methoxy-2-oxo-9-(3-pyrazol-1-ylpropoxy)-6-(2-thienyl)-6,7-dihydrobenzo[a]quinolizine-3-carboxylic Acid

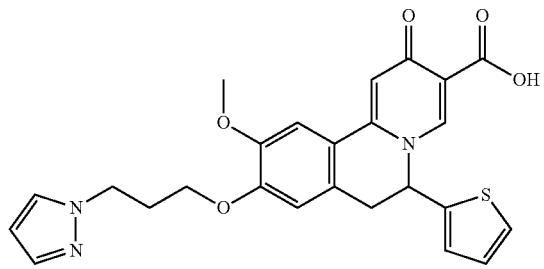 [SMILES: COc1cc2c(cc1OCCCn1cccn1)CC(c1cccs1)n1cc(C(=O)O)c(=O)cc1-2]

Step 1: Preparation of 1-(3-bromopropyl)pyrazole

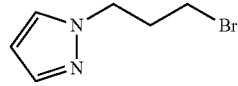

To a solution of 1H-pyrazole (1 g, 14.7 mmol) in acetone (20 mL) was added K₂CO₃ (4.06 g, 29.4 mmol) and 1,3-dibromopropane (14.8 g, 73.4 mmol). The mixture was heated at 30° C. for 12 hrs. The mixture was concentrated under reduced pressure and the residue was partitioned between H₂O (150 mL) and EtOAc (200 mL). The organic layer was separated, washed with brine (150 mL), dried over anhydrous Na₂SO₄ and concentrated under reduced pressure. The residue was purified by column chromatography to afford compound 1-(3-bromopropyl)pyrazole (500 mg) as a yellow oil.

Step 2: Preparation of ethyl 10-methoxy-2-oxo-9-(3-pyrazol-1-ylpropoxy)-6-(2-thienyl)-6,7-dihydrobenzo[a]quinolizine-3-carboxylate

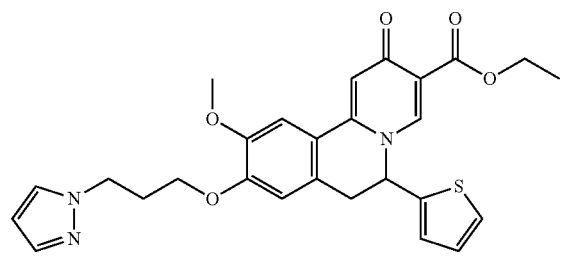 [SMILES: CCOC(=O)c1cn2c(cc1=O)-c1cc(OC)c(OCCCn3cccn3)cc1CC2c1cccs1]

A solution of compound ethyl 9-hydroxy-10-methoxy-2-oxo-6-(2-thienyl)-6,7-dihydrobenzo[a]quinolizine-3-carboxylate (150 mg, 377 μmol) in DMF (3 mL) was added K₂CO₃ (104 mg, 754 μmol) and 1-(3-bromopropyl)pyrazole (85.6 mg, 453 μmol). The mixture was heated at 30° C. for 12 hrs and then partitioned between H₂O (50 mL) and EtOAc (100 mL). The organic layer was separated, washed with brine (50 mL), dried over anhydrous Na₂SO₄ and concentrated under reduced pressure. The residue was purified by column chromatography to afford crude ethyl 10-methoxy-2-oxo-9-(3-pyrazol-1-ylpropoxy)-6-(2-thienyl)-6,7-dihydrobenzo[a]quinolizine-3-carboxylate (100 mg) as a yellow oil.

Step 3: Preparation of 10-methoxy-2-oxo-9-(3-pyrazol-1-ylpropoxy)-6-(2-thienyl)-6,7-dihydrobenzo[a]quinolizine-3-carboxylic Acid

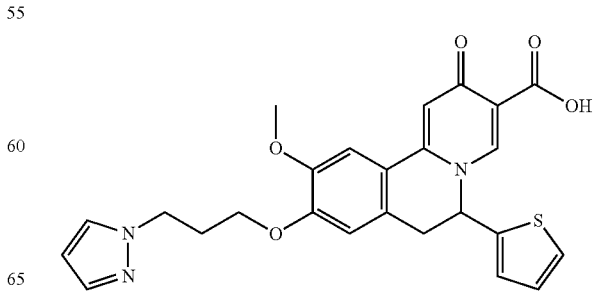

To a solution of ethyl 10-methoxy-2-oxo-9-(3-pyrazol-1-ylpropoxy)-6-(2-thienyl)-6,7-dihydrobenzo[a]quinolizine-3-carboxylate (100 mg, 198 μmol) in MeOH (2 mL) was added 2 M NaOH aqueous solution (0.197 mL, 395 μmol). The mixture was stirred at 30° C. for 12 hrs, and then concentrated under reduced pressure. The residue was diluted with H₂O (20 mL) and acidified with 1 M hydrochloric acid to pH=3. Then the resulting mixture was extracted with DCM (100 mL). The organic layer was washed with brine (50 mL), dried over anhydrous Na₂SO₄ and concentrated under reduced pressure. The residue was purified by prep-HPLC to afford 10-methoxy-2-oxo-9-(3-pyrazol-1-ylpropoxy)-6-(2-thienyl)-6,7-dihydrobenzo[a]quinolizine-3-carboxylic acid (13.8 mg) as a white solid. $^1$H NMR (400 MHz, DMSO-d6) δ: 2.25 (t, 2H), 3.23-3.28 (m, 1H), 3.70 (dd, 1H), 3.90 (s, 3H), 3.94-4.07 (m, 2H), 4.27 (t, 2H), 6.23 (t, 1H), 6.33 (d, 1H), 6.90 (dd, 1H), 7.02 (s, 2H), 7.36 (d, 1H), 7.44 (d, 1H), 7.52 (d, 2H), 7.72 (d, 1H), 8.98 (s, 1H). MS obsd. (ESI$^+$) [(M+H)$^+$]: 478.

Example 17: 9-(3-hydroxypropoxy)-10-methoxy-2-oxo-6-(2-thienyl)-6,7-dihydrobenzo[a]quinolizine-3-carboxylic Acid

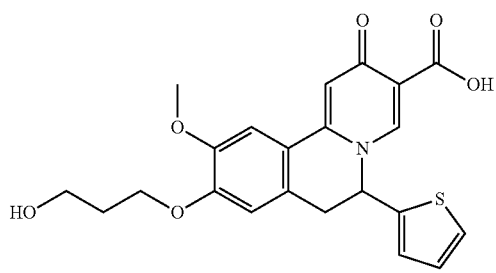

Step 1: Preparation of ethyl 9-(3-hydroxypropoxy)-10-methoxy-2-oxo-6-(2-thienyl)-6,7-dihydrobenzo[a]quinolizine-3-carboxylate

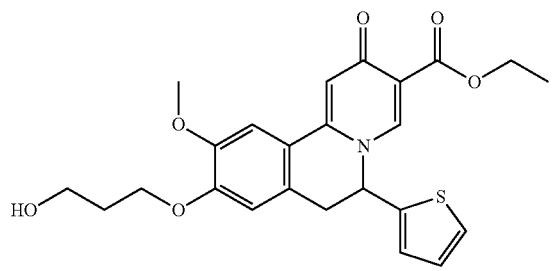

To a solution of compound ethyl 9-hydroxy-10-methoxy-2-oxo-6-(2-thienyl)-6,7-dihydrobenzo[a]quinolizine-3-carboxylate (150 mg, 377 μmol) in DMF (3 mL) was added K₂CO₃ (78 mg, 566 μmol) and 3-bromopropan-1-ol (79 mg, 566 μmol). The mixture was heated at 30° C. for 12 hrs, and then partitioned between H₂O (50 mL) and EtOAc (100 mL). The organic layer was separated, washed with brine (50 mL), dried over anhydrous Na₂SO₄ and concentrated under reduced pressure to afford crude ethyl 9-(3-hydroxypropoxy)-10-methoxy-2-oxo-6-(2-thienyl)-6,7-dihydrobenzo[a]quinolizine-3-carboxylate (200 mg) as brown oil, which was used directly in the next step without further purification.

Step 2: Preparation of 9-(3-hydroxypropoxy)-10-methoxy-2-oxo-6-(2-thienyl)-6,7-dihydrobenzo[a]quinolizine-3-carboxylic Acid

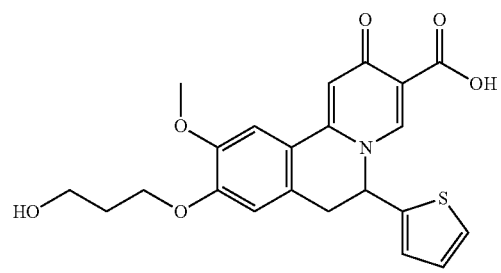

To a solution of ethyl 9-(3-hydroxypropoxy)-10-methoxy-2-oxo-6-(2-thienyl)-6,7-dihydrobenzo[a]quinolizine-3-carboxylate (200 mg, 439 μmol) in MeOH (2 mL) was added 2 M NaOH aqueous solution (0.439 mL, 878 μmol). The mixture was stirred at 30° C. for 12 hrs, and then concentrated under reduced pressure. The residue was diluted with H₂O (20 mL) and acidified with 1 M hydrochloric acid to pH=3. Then the resulting mixture was extracted with DCM (100 mL). The organic layer was washed with brine (50 mL), dried over anhydrous Na₂SO₄ and concentrated under reduced pressure. The residue was purified by prep-HPLC to afford 9-(3-hydroxypropoxy)-10-methoxy-2-oxo-6-(2-thienyl)-6,7-dihydrobenzo[a]quinolizine-3-carboxylic acid (7.9 mg) as a yellow solid. $^1$H NMR (400 MHz, DMSO-d6) δ: 1.89 (t, 2H), 3.33 (br. s., 1H), 3.55 (t, 2H), 3.71 (d, 1H), 3.87 (s, 3H), 4.09 (t, 2H), 4.60 (br. s., 1H), 6.33 (br. s., 1H), 6.82-6.94 (m, 1H), 6.96-7.13 (m, 2H), 7.35 (d, 1H), 7.50 (br. s., 2H), 8.97 (br. s., 1H). MS obsd. (ESI$^+$) [(M+H)$^+$]: 428.

Example 18: 10-methoxy-2-oxo-9-[3-(1-piperidyl)propoxy]-6-(2-thienyl)-6,7-dihydrobenzo[a]quinolizine-3-carboxylic Acid Formate

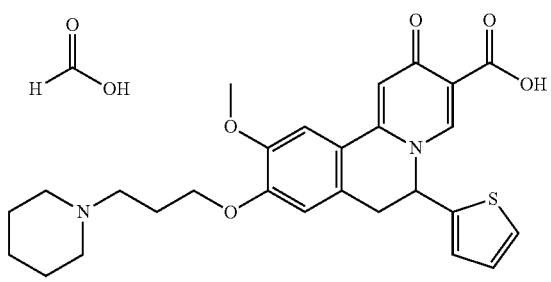 [SMILES: COc1cc2c(cc1OCCCN1CCCCC1)CC(c1cccs1)n1cc(C(=O)O)c(=O)cc1-2 ; O=CO]

Step 1: Preparation of ethyl 9-(3-bromopropoxy)-10-methoxy-2-oxo-6-(2-thienyl)-6,7-dihydrobenzo[a]quinolizine-3-carboxylate

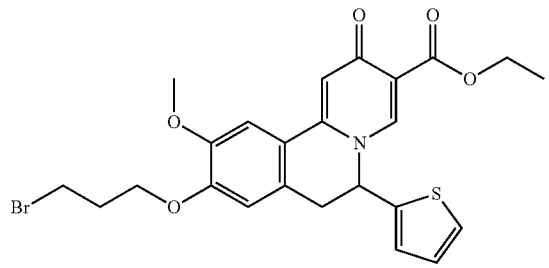 [SMILES: CCOC(=O)c1cn2c(cc1=O)-c1cc(OC)c(OCCCBr)cc1CC2c1cccs1]

A mixture of ethyl 9-hydroxy-10-methoxy-2-oxo-6-(2-thienyl)-6,7-dihydrobenzo[a]quinolizine-3-carboxylate (400 mg, 1.0 mmol), 1,3-dibromopropane (244 mg, 1.21 mmol) and $K_2CO_3$ (209 mg, 1.51 mmol) in DMF (7 mL) was stirred at room temperature for 16 hrs. The mixture was partitioned between $H_2O$ and DCM. The organic layer was separated, washed with brine, dried over anhydrous $Na_2SO_4$ and concentrated under reduced pressure to give crude ethyl 9-(3-bromopropoxy)-10-methoxy-2-oxo-6-(2-thienyl)-6,7-dihydrobenzo[a]quinolizine-3-carboxylate (500 mg), which was used directly in the next step without further purification.

Step 2: Preparation of ethyl 10-methoxy-2-oxo-9-[3-(1-piperidyl)propoxy]-6-(2-thienyl)-6,7-dihydrobenzo[a]quinolizine-3-carboxylate

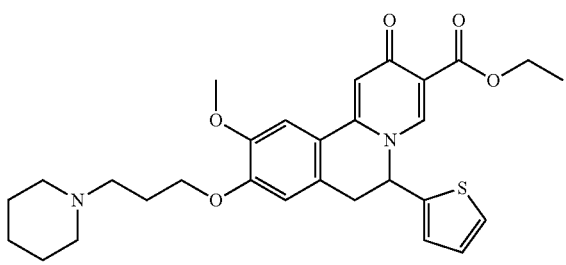 [SMILES: CCOC(=O)c1cn2c(cc1=O)-c1cc(OC)c(OCCCN3CCCCC3)cc1CC2c1cccs1]

A mixture of ethyl 9-(3-bromopropoxy)-10-methoxy-2-oxo-6-(2-thienyl)-6,7-dihydrobenzo[a]quinolizine-3-carboxylate (200 mg, 0.39 mmol), piperidine (164 mg, 1.93 mmol) and $K_2CO_3$ (267 mg, 1.93 mmol) in DMF (5 mL) was stirred at room temperature for 16 hrs. The mixture was partitioned between $H_2O$ and DCM. The organic layer was separated, washed with brine, dried over anhydrous $Na_2SO_4$ and concentrated under reduced pressure to give crude ethyl 10-methoxy-2-oxo-9-[3-(1-piperidyl)propoxy]-6-(2-thienyl)-6,7-dihydrobenzo[a]quinolizine-3-carboxylate (140 mg), which was used directly in the next step without further purification.

Step 3: Preparation of 10-methoxy-2-oxo-9-[3-(1-piperidyl)propoxy]-6-(2-thienyl)-6,7-dihydrobenzo[a]quinolizine-3-carboxylic Acid Formate

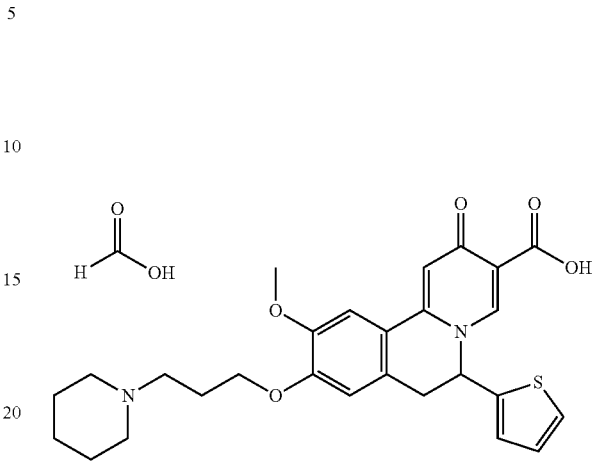

A mixture of ethyl 10-methoxy-2-oxo-9-[3-(1-piperidyl)propoxy]-6-(2-thienyl)-6,7-dihydrobenzo[a]quinolizine-3-carboxylate (140 mg, 0.27 mmol) and NaOH (21 mg) in MeOH (3 mL) and $H_2O$ (0.3 mL) was stirred at room temperature for 16 hrs. The mixture was concentrated under reduced pressure. The residue was diluted with $H_2O$ and acidified with 1 M hydrochloric acid to pH=2-3. The resulting mixture was filtered. The filter cake was dried and purified by prep-HPLC (formic acid as additive) to afford 10-methoxy-2-oxo-9-[3-(1-piperidyl)propoxy]-6-(2-thienyl)-6,7-dihydrobenzo[a]quinolizine-3-carboxylic acid formate (23 mg) as a white solid. $^1$H NMR (400 MHz, DMSO-d6) δ: 1.39 (d, 2H), 1.46-1.57 (m, 4H), 1.91 (t, 2H), 2.36-2.48 (m, 6H), 3.34 (s., 1H), 3.72 (dd, 1H), 3.88 (s, 3H), 4.07 (t, 2H), 6.34 (d, 1H), 6.85-6.95 (m, 1H), 7.00-7.11 (m, 2H), 7.36 (d, 1H), 7.45-7.56 (m, 2H), 8.21 (s, 1H), 8.98 (s, 1H). MS obsd. (ESI$^+$) [(M+H)$^+$]: 495.

Example 19: 9-(3-cyanopropoxy)-10-methoxy-2-oxo-6-(2-thienyl)-6,7-dihydrobenzo[a]quinolizine-3-carboxylic Acid

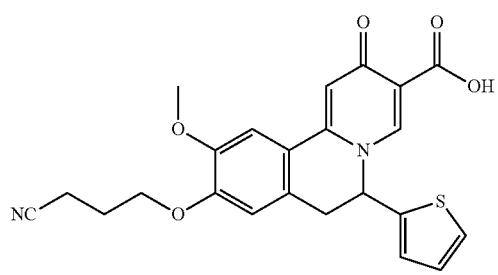 [SMILES: COc1cc2c(cc1OCCCC#N)CC(c1cccs1)n1cc(C(=O)O)c(=O)cc1-2]

Step 1: Preparation of ethyl 9-(3-cyanopropoxy)-10-methoxy-2-oxo-6-(2-thienyl)-6,7-dihydrobenzo[a]quinolizine-3-carboxylate

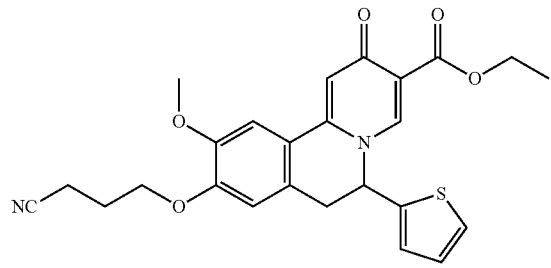 [SMILES: CCOC(=O)c1cn2c(cc1=O)-c1cc(OC)c(OCCCC#N)cc1CC2c1cccs1]

To a solution of compound ethyl 9-hydroxy-10-methoxy-2-oxo-6-(2-thienyl)-6,7-dihydrobenzo[a]quinolizine-3-carboxylate (150 mg, 377 μmol) in DMF (3 mL) was added $K_2CO_3$ (78 mg, 566 μmol) and 4-bromobutanenitrile (84 mg, 566 μmol). Then the mixture was stirred at 30° C. for 12 hrs. The mixture partitioned between $H_2O$ (50 mL) and EtOAc (100 mL). The organic layer was separated, washed with brine (50 mL), dried over anhydrous $Na_2SO_4$ and concentrated under reduced pressure to afford crude ethyl 9-(3-cyanopropoxy)-10-methoxy-2-oxo-6-(2-thienyl)-6,7-dihydrobenzo[a]quinolizine-3-carboxylate (190 mg) as brown oil, which was used directly in the next step without further purification.

Step 2: Preparation of 9-(3-cyanopropoxy)-10-methoxy-2-oxo-6-(2-thienyl)-6,7-dihydrobenzo[a]quinolizine-3-carboxylic Acid

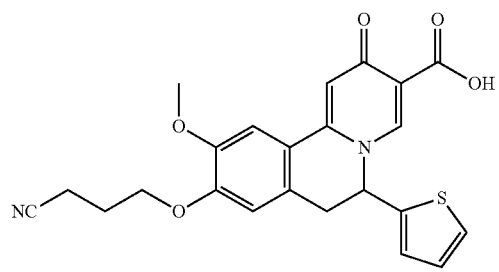 [SMILES: COc1cc2c(cc1OCCCC#N)CC(c1cccs1)n1cc(C(=O)O)c(=O)cc1-2]

A solution of ethyl 9-(3-cyanopropoxy)-10-methoxy-2-oxo-6-(2-thienyl)-6,7-dihydrobenzo[a]quinolizine-3-carboxylate (190 mg, 409 μmol) in THF (2 mL) was added 2 M LiOH aqueous solution (0.409 mL, 818 μmol). The mixture was stirred at 30° C. for 12 hrs, and then concentrated under reduced pressure. The residue was diluted with $H_2O$ (20 mL) and acidified with 1 M hydrochloric acid to pH=3. Then the resulting mixture was extracted with DCM (100 mL). The organic layer was washed with brine (50 mL), dried over anhydrous $Na_2SO_4$ and concentrated under reduced pressure. The residue was purified by prep-HPLC to afford 9-(3-cyanopropoxy)-10-methoxy-2-oxo-6-(2-thienyl)-6,7-dihydrobenzo[a]quinolizine-3-carboxylic acid (32.5 mg) as a white solid. $^1$H NMR (400 MHz, DMSO-d6) δ: 1.97-2.15 (m, 2H), 2.65 (t, 2H), 3.42-3.49 (m, 1H), 3.72 (dd, 1H), 3.89 (s, 3H), 4.10 (t, 2H), 6.35 (br. s., 1H), 6.91 (dd, 1H), 7.03 (br. s., 1H), 7.11 (s, 1H), 7.30-7.41 (m, 1H), 7.53 (d, 2H), 8.99 (s, 1H). MS obsd. (ESI$^+$) [(M+H)$^+$]: 437.

Example 20: 10-methoxy-2-oxo-9-[2-(2-oxopyrrolidin-1-yl)ethoxy]-6-(2-thienyl)-6,7-dihydrobenzo[a]quinolizine-3-carboxylic Acid

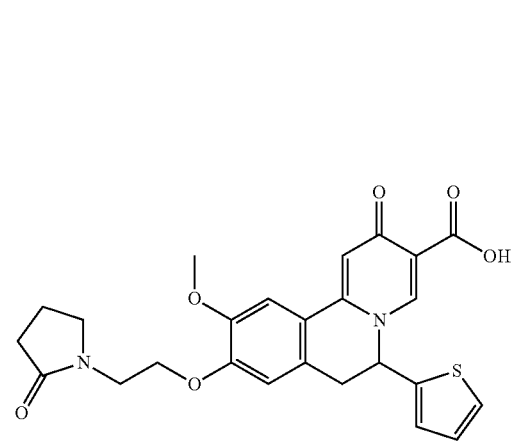 [SMILES: COc1cc2c(cc1OCCN1CCCC1=O)CC(c1cccs1)n1cc(C(=O)O)c(=O)cc1-2]

Step 1: Preparation of ethyl 9-(2-bromoethoxy)-10-methoxy-2-oxo-6-(2-thienyl)-6,7-dihydrobenzo[a]quinolizine-3-carboxylate

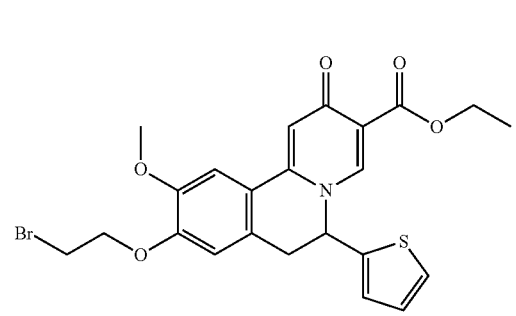 [SMILES: CCOC(=O)c1cn2c(cc1=O)-c1cc(OC)c(OCCBr)cc1CC2c1cccs1]

A mixture of ethyl 9-hydroxy-10-methoxy-2-oxo-6-(2-thienyl)-6,7-dihydrobenzo[a]quinolizine-3-carboxylate (100 mg, 0.25 mmol), 1,2-dibromoethane (57 mg, 0.30 mmol) and $K_2CO_3$ (53 mg, 0.38 mmol) in DMF (3 ml) was stirred at room temperature for 16 hrs. The mixture was partitioned between $H_2O$ and DCM. The organic layer was separated, washed with brine, dried over anhydrous $Na_2SO_4$ and concentrated under reduced pressure to give crude ethyl 9-(2-bromoethoxy)-10-methoxy-2-oxo-6-(2-thienyl)-6,7-dihydrobenzo[a]quinolizine-3-carboxylate (130 mg), which was used directly in the next step without further purification.

Step 2: Preparation of 10-methoxy-2-oxo-9-[2-(2-oxopyrrolidin-1-yl)ethoxy]-6-(2-thienyl)-6,7-dihydrobenzo[a]quinolizine-3-carboxylic Acid

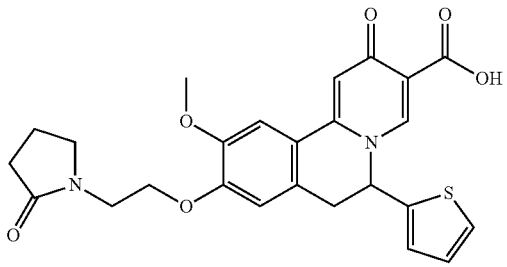 [SMILES: COc1cc2c(cc1OCCN1CCCC1=O)CC(c1cccs1)n1cc(C(=O)O)c(=O)cc1-2]

To a cooled and stirred solution of pyrrolidin-2-one (290 mg, 3.41 mmol) in DMF (2 mL) was added NaH (50 mg, 1.25 mmol) at 0° C. After the addition, the resulting mixture was warmed up to room temperature and stirred for 10 min. Then to the mixture was added ethyl 9-(2-bromoethoxy)-10-methoxy-2-oxo-6-(2-thienyl)-6,7-dihydrobenzo[a]quinolizine-3-carboxylate (130 mg, 0.25 mmol) and the resulting mixture was stirred at rt for 16 hrs. The reaction was quenched by addition of saturated NH₄Cl aqueous solution, and then the mixture was extracted with EtOAc. The organic layer was washed with brine, dried over anhydrous Na₂SO₄ and concentrated under reduced pressure. The residue was purified by prep-HPLC to afford 10-methoxy-2-oxo-9-[2-(2-oxopyrrolidin-1-yl)ethoxy]-6-(2-thienyl)-6,7-dihydrobenzo[a]quinolizine-3-carboxylic acid (7.0 mg) as a white solid. $^1$H NMR (400 MHz, DMSO-d6) δ: 1.91 (quin, 2H), 2.15-2.26 (m, 2H), 3.31-3.32 (m, 1H), 3.48 (t, 2H), 3.56 (t, 2H), 3.71 (dd, 1H), 3.88 (s, 3H), 4.13 (t, 2H), 6.34 (d, 1H), 6.90 (dd, 1H), 7.01 (d, 1H), 7.10 (s, 1H), 7.36 (d, 1H), 7.52 (d, 2H), 8.92-9.03 (m, 1H). MS obsd. (ESI$^+$) [(M+H)$^+$]: 481.

Example 21: 9-[6-(tert-butoxycarbonylamino)hexoxy]-10-methoxy-2-oxo-6-(2-thienyl)-6,7-dihydrobenzo[a]quinolizine-3-carboxylic Acid

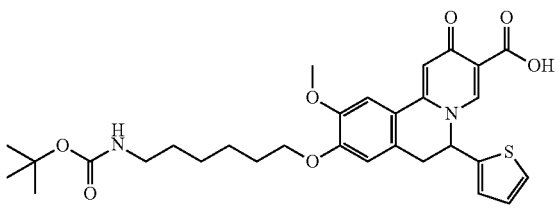 [SMILES: COc1cc2c(cc1OCCCCCCNC(=O)OC(C)(C)C)CC(c1cccs1)n1cc(C(=O)O)c(=O)cc1-2]

Step 1: Preparation of ethyl 9-[6-(tert-butoxycarbonylamino)hexoxy]-10-methoxy-2-oxo-6-(2-thienyl)-6,7-dihydrobenzo[a]quinolizine-3-carboxylate

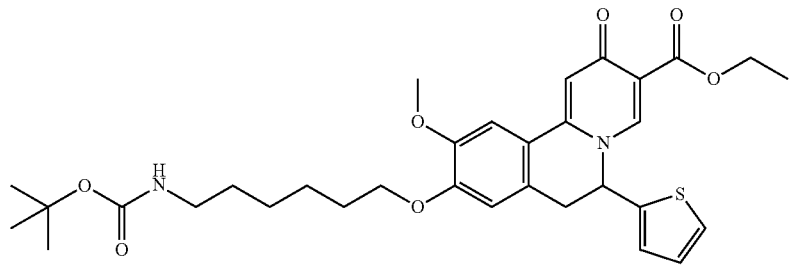 [SMILES: CCOC(=O)c1cn2c(cc1=O)-c1cc(OC)c(OCCCCCCNC(=O)OC(C)(C)C)cc1CC2c1cccs1]

To a solution of ethyl 9-hydroxy-10-methoxy-2-oxo-6-(2-thienyl)-6,7-dihydrobenzo[a]quinolizine-3-carboxylate (120 mg, 0.3 mmol) in DMF (3 mL) was added K₂CO₃ (83 mg, 0.6 mmol) and tert-butyl (6-bromohexyl)carbamate (101 mg, 0.36 mmol). The mixture was stirred at 30° C. for 12 hrs, and then partitioned between H₂O (50 mL) and EtOAc (100 mL). The organic layer was separated, washed with brine (50 mL), dried over anhydrous Na₂SO₄ and concentrated under reduced pressure to afford crude ethyl 9-[6-(tert-butoxycarbonylamino)hexoxy]-10-methoxy-2-oxo-6-(2-thienyl)-6,7-dihydrobenzo[a]quinolizine-3-carboxylate (140 mg) as a yellow oil, which was used directly in the next step without further purification.

Step 2: Preparation of 9-[6-(tert-butoxycarbonylamino)hexoxy]-10-methoxy-2-oxo-6-(2-thienyl)-6,7-dihydrobenzo[a]quinolizine-3-carboxylic Acid Step 1: Preparation of ethyl 9-(6-aminohexoxy)-10-methoxy-2-oxo-6-(2-thienyl)-6,7-dihydrobenzo[a]quinolizine-3-carboxylate hydrochloride

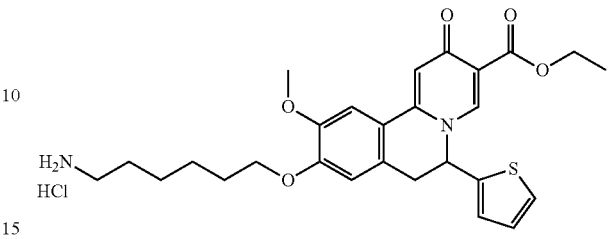

A solution of ethyl 9-[6-(tert-butoxycarbonylamino)hexoxy]-10-methoxy-2-oxo-6-(2-thienyl)-6,7-dihydrobenzo[a]quinolizine-3-carboxylate (70 mg, 117 μmol) in HCl/dioxane (3 mL) was stirred at 30° C. for 12 h. The mixture was concentrated under reduced pressure to afford crude ethyl 9-(6-aminohexoxy)-10-methoxy-2-oxo-6-(2-thienyl)-6,7-dihydrobenzo[a]quinolizine-3-carboxylate hydrochloride (60 mg) as a yellow oil, which was used directly in the next step without further purification.

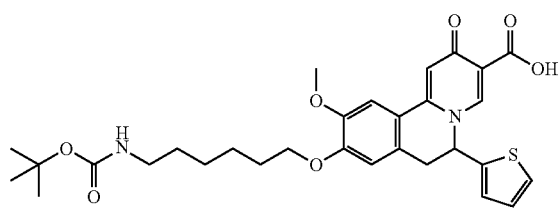 [SMILES: COc1cc2c(cc1OCCCCCCNC(=O)OC(C)(C)C)CC(c1cccs1)n1cc(C(=O)O)c(=O)cc1-2]

To a solution of crude ethyl 9-[6-(tert-butoxycarbonylamino)hexoxy]-10-methoxy-2-oxo-6-(2-thienyl)-6,7-dihydrobenzo[a]quinolizine-3-carboxylate (70 mg, 0.117 mmol) in MeOH (1 mL) was added 2 M NaOH aqueous solution (0.117 mL, 0.234 mmol). The mixture was stirred at 30° C. for 2 hrs, and then diluted with $H_2O$ (20 mL). The resulting mixture was acidified with 1 M hydrochloric acid to pH=3, and extracted with DCM (100 mL). The organic layer was washed with brine (50 mL), dried over anhydrous $Na_2SO_4$ and concentrated under reduced pressure. The residue was purified by prep-HPLC to afford 9-[6-(tert-butoxycarbonylamino)hexoxy]-10-methoxy-2-oxo-6-(2-thienyl)-6,7-dihydrobenzo[a]quinolizine-3-carboxylic acid (18.1 mg) as white solid. $^1$H NMR (400 MHz, DMSO-d6) δ: 1.36 (s, 15H) 1.71 (d, 2H) 2.81-2.98 (m, 2H) 3.11-3.28 (m, 1H) 3.70 (d, 1H) 3.87 (s, 3H) 4.01 (t, 2H) 6.33 (br. s., 1H) 6.77 (br. s., 1H) 6.84-6.95 (m, 1H) 6.96-7.12 (m, 2H) 7.35 (d, 1H) 7.50 (br. s., 2H) 8.96 (br. s., 1H). MS obsd. (ESI$^+$) [(M+H)$^+$]: 569.

Step 2: Preparation of 9-(6-aminohexoxy)-10-methoxy-2-oxo-6-(2-thienyl)-6,7-dihydrobenzo[a]quinolizine-3-carboxylic Acid Formate

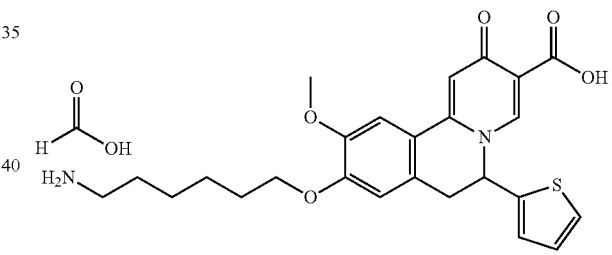

To a solution of ethyl 9-(6-aminohexoxy)-10-methoxy-2-oxo-6-(2-thienyl)-6,7-dihydrobenzo[a]quinolizine-3-carboxylate hydrochloride (60 mg, 0.112 mmol) in MeOH (1 mL) was added 2 M NaOH (0.112 mL, 0.224 mmol). The mixture was stirred at 30° C. for 2 hrs, and then concentrated under reduced pressure. The residue was diluted with $H_2O$ (20 mL) and acidified with 1 M hydrochloric acid to pH=3. Then the mixture was extracted with DCM (60 mL). The organic layer was washed with brine (50 mL), dried over anhydrous $Na_2SO_4$ and concentrated under reduced pressure. The residue was purified by prep-HPLC (formic acid as additive) to afford compound 9-(6-aminohexoxy)-10-methoxy-2-oxo-6-(2-thienyl)-6,7-dihydrobenzo[a]quinolizine-3-carboxylic acid formate (12 mg) as a yellow solid. $^1$H NMR (400 MHz, DMSO-d6) δ: 1.38 (br. s., 4H), 1.48-1.63 (m, 2H), 1.64-1.82 (m, 2H), 2.74 (t, 2H), 3.31 (br. s., 1H), 3.72 (d, 1H), 3.87 (s, 3H), 4.01 (t, 2H), 6.33 (br. s., 1H), 6.90 (dd, 1H), 6.95-7.11 (m, 2H), 7.35 (d, 1H), 7.45-7.52 (m, 1H), 8.40 (br. s., 1H), 8.95 (br. s., 1H). MS obsd. (ESI$^+$) [(M+H)$^+$]: 469.

Example 22: 9-(6-aminohexoxy)-10-methoxy-2-oxo-6-(2-thienyl)-6,7-dihydrobenzo[a]quinolizine-3-carboxylic Acid Formate

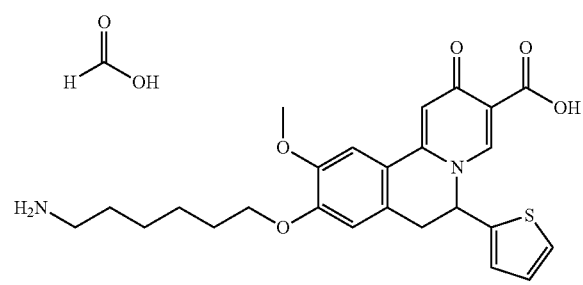 [SMILES: COc1cc2c(cc1OCCCCCCN)CC(c1cccs1)n1cc(C(=O)O)c(=O)cc1-2 ; O=CO]

Example 23: 9-(6-acetamidohexoxy)-10-methoxy-2-oxo-6-(2-thienyl)-6,7-dihydrobenzo[a]quinolizine-3-carboxylic Acid

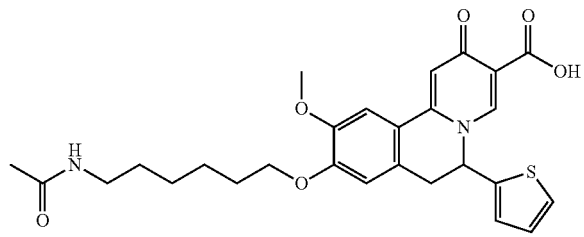 [SMILES: COc1cc2c(cc1OCCCCCCNC(C)=O)CC(c1cccs1)n1cc(C(=O)O)c(=O)cc1-2]

Step 1: Preparation of ethyl 9-(6-acetamidohexoxy)-10-methoxy-2-oxo-6-(2-thienyl)-6,7-dihydrobenzo[a]quinolizine-3-carboxylate

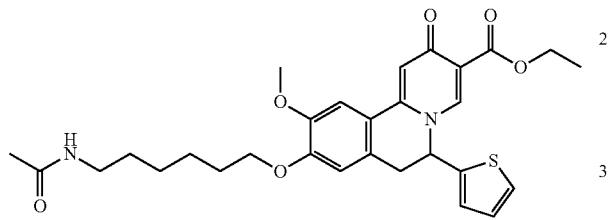

To a solution of ethyl 9-(6-aminohexoxy)-10-methoxy-2-oxo-6-(2-thienyl)-6,7-dihydrobenzo[a]quinolizine-3-carboxylate hydrochloride (80 mg, 0.15 mmol) in DCM (3 mL) was added DIPEA (97 mg, 0.75 mmol) and acetyl chloride (95 mg, 0.75 mmol). The mixture was stirred at 30° C. for 12 hrs, and then diluted with $H_2O$ (20 mL). The resulting mixture was extracted with DCM (60 mL). The organic layer was washed with brine (50 mL), dried over anhydrous $Na_2SO_4$ and concentrated under reduced pressure to give crude ethyl 9-(6-acetamidohexoxy)-10-methoxy-2-oxo-6-(2-thienyl)-6,7-dihydrobenzo[a]quinolizine-3-carboxylate (100 mg) as a yellow oil, which was used directly in the next step without further purification.

Step 2: Preparation of 9-(6-acetamidohexoxy)-10-methoxy-2-oxo-6-(2-thienyl)-6,7-dihydrobenzo[a]quinolizine-3-carboxylic Acid

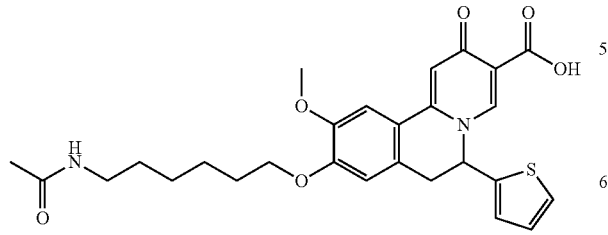

To a solution of ethyl 9-(6-acetamidohexoxy)-10-methoxy-2-oxo-6-(2-thienyl)-6,7-dihydrobenzo[a]quinolizine-3-carboxylate (100 mg, 0.185 mmol) in MeOH (2 mL) was added 2 M NaOH aqueous solution (0.186 mL, 0.371 mmol). The mixture was stirred at 30° C. for 2 hrs, and then concentrated under reduced pressure. The residue was diluted with $H_2O$ (20 mL) and acidified with 1 M hydrochloric acid to pH=3. Then the mixture was extracted with DCM (60 mL). The organic layer was washed with brine (50 mL), dried over anhydrous $Na_2SO_4$ and concentrated under reduced pressure. The residue was purified by prep-HPLC to afford 9-(6-acetamidohexoxy)-10-methoxy-2-oxo-6-(2-thienyl)-6,7-dihydrobenzo[a]quinolizine-3-carboxylic acid (17.5 mg) as a white solid. $^1$H NMR (400 MHz, DMSO-d6) δ: 1.25-1.48 (m, 6H), 1.66-1.76 (m, 2H), 1.77 (s, 3H), 3.01 (q, 2H), 3.39-3.47 (m, 1H), 3.71 (dd, 1H), 3.87 (s, 3H), 4.02 (t, 2H), 6.34 (d, 1H), 6.90 (dd, 1H), 7.00-7.11 (m, 2H), 7.36 (dd, 1H), 7.51 (d, 2H), 7.78 (br. s., 1H), 8.98 (s, 1H). MS obsd. (ESI$^+$) [(M+H)$^+$]: 511.

Example 24: 9-[6-(methanesulfonamido)hexoxy]-10-methoxy-2-oxo-6-(2-thienyl)-6,7-dihydrobenzo[a]quinolizine-3-carboxylic Acid

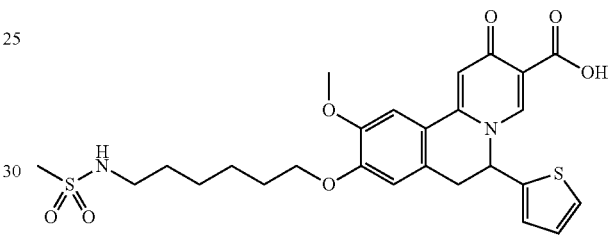

Step 1: Preparation of ethyl 9-[6-(methanesulfonamido)hexoxy]-10-methoxy-2-oxo-6-(2-thienyl)-6,7-dihydrobenzo[a]quinolizine-3-carboxylate

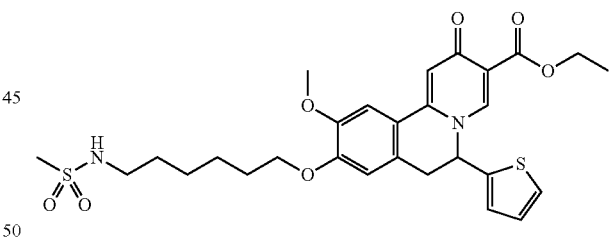

To a solution of ethyl 9-(6-aminohexoxy)-10-methoxy-2-oxo-6-(2-thienyl)-6,7-dihydrobenzo[a]quinolizine-3-carboxylate hydrochloride (100 mg, 0.187 mmol) in DCM (3 mL) was added DIPEA (121 mg, 0.937 mmol) and methanesulfonyl chloride (107 mg, 937 μmol). The mixture was stirred at 30° C. for 12 hrs, and then concentrated under reduced pressure. The residue was partitioned between $H_2O$ (20 mL) and DCM (60 mL). The organic layer was separated, washed with brine (50 mL), dried over anhydrous $Na_2SO_4$ and concentrated under reduced pressure to afford crude ethyl 9-[6-(methanesulfonamido)hexoxy]-10-methoxy-2-oxo-6-(2-thienyl)-6,7-dihydrobenzo[a]quinolizine-3-carboxylate (100 mg) as a yellow oil, which was used directly in the next step without further purification.

Step 2: Preparation of 9-[6-(methanesulfonamido)hexoxy]-10-methoxy-2-oxo-6-(2-thienyl)-6,7-dihydrobenzo[a]quinolizine-3-carboxylic Acid

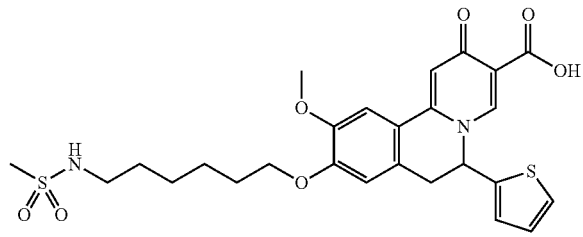 [SMILES: COc1cc2c(cc1OCCCCCCNS(C)(=O)=O)CC(c1cccs1)n1cc(C(=O)O)c(=O)cc1-2]

To a solution of ethyl 9-[6-(methanesulfonamido)hexoxy]-10-methoxy-2-oxo-6-(2-thienyl)-6,7-dihydrobenzo[a]quinolizine-3-carboxylate (100 mg, 0.174 mmol) in MeOH (2 mL) was added 2 M NaOH (0.174 mL, 0.348 mmol). The mixture was stirred at 30° C. for 2 hrs, then diluted with H$_2$O (20 mL) and acidified with 1 M hydrochloric acid to pH=3. Then the resulting mixture was extracted with DCM (60 mL). The organic layer was washed with brine (50 mL), dried over anhydrous Na$_2$SO$_4$ and concentrated under reduced pressure. The residue was purified by prep-HPLC to afford 9-[6-(methanesulfonamido)hexoxy]-10-methoxy-2-oxo-6-(2-thienyl)-6,7-dihydrobenzo[a]quinolizine-3-carboxylic acid (53.3 mg) as a yellow solid. $^1$H NMR (400 MHz, DMSO-d6) δ: 1.32-1.53 (m, 6H), 1.66-1.81 (m, 2H), 2.87 (s, 3H), 2.92 (q, 2H), 3.40-3.48 (m, 1H), 3.71 (dd, 1H), 3.87 (s, 3H), 4.02 (t, 2H), 6.34 (d, 1H), 6.85-6.96 (m, 2H), 6.98-7.11 (m, 2H), 7.36 (dd, 1H), 7.50 (d, 2H), 8.98 (s, 1H). MS obsd. (ESI$^+$) [(M+H)$^+$]: 547.

Example 25: 9-(6-hydroxyhexoxy)-10-methoxy-2-oxo-6-(2-thienyl)-6,7-dihydrobenzo[a]quinolizine-3-carboxylic Acid

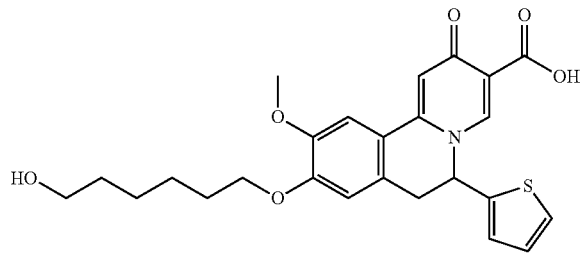 [SMILES: COc1cc2c(cc1OCCCCCCO)CC(c1cccs1)n1cc(C(=O)O)c(=O)cc1-2]

Step 1: Preparation of ethyl 9-(6-hydroxyhexoxy)-10-methoxy-2-oxo-6-(2-thienyl)-6,7-dihydrobenzo[a]quinolizine-3-carboxylate To a solution of compound ethyl 9-hydroxy-10-methoxy-2-oxo-6-(2-thienyl)-6,7-dihydrobenzo[a]quinolizine-3-carboxylate (150 mg, 0.377 mmol) in DMF (3 mL) was added K$_2$CO$_3$ (104 mg, 754 μmol) and 6-bromohexan-1-ol (102 mg, 0.566 mmol). The mixture was stirred at 30° C. for 12 hrs, and then partitioned between H$_2$O (50 mL) and EtOAc (100 mL). The organic layer was separated, washed with brine (50 mL), dried over anhydrous Na$_2$SO$_4$ and concentrated under reduced pressure to give ethyl 9-(6-hydroxyhexoxy)-10-methoxy-2-oxo-6-(2-thienyl)-6,7-dihydrobenzo[a]quinolizine-3-carboxylate (90 mg), which was used directly in the next step without further purification.

Step 2: Preparation of 9-(6-hydroxyhexoxy)-10-methoxy-2-oxo-6-(2-thienyl)-6,7-dihydrobenzo[a]quinolizine-3-carboxylic Acid

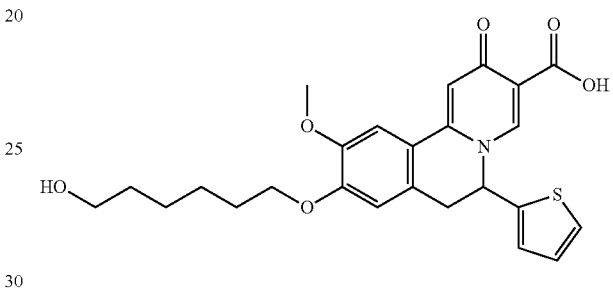

To a solution of ethyl 9-(6-hydroxyhexoxy)-10-methoxy-2-oxo-6-(2-thienyl)-6,7-dihydrobenzo[a]quinolizine-3-carboxylate (90 mg, 0.181 mmol) in MeOH (2 mL) was added 2 M NaOH aqueous solution (0.181 mL, 0.362 mmol). The mixture was stirred at 30° C. for 12 hrs, then diluted with H$_2$O (20 mL) and acidified with 1 M hydrochloric acid to pH=3. The resulting mixture was extracted with DCM (100 mL). The organic layer was washed with brine (50 mL), dried over anhydrous Na$_2$SO$_4$ and concentrated under reduced pressure. The residue was purified by prep-HPLC to afford 9-(6-hydroxyhexoxy)-10-methoxy-2-oxo-6-(2-thienyl)-6,7-dihydrobenzo[a]quinolizine-3-carboxylic acid (48 mg) as white solid. $^1$H NMR (400 MHz, DMSO-d6) δ: 1.15-1.55 (m, 6H), 1.73 (br. s., 2H), 3.12-3.30 (m, 1H), 3.73 (br. s., 1H), 3.86 (br. s., 3H), 4.01 (br. s., 2H), 4.39 (br. s., 2H), 6.33 (br. s., 1H), 6.90 (d, 1H), 7.04 (d, 2H), 7.35 (br. s., 1H), 7.50 (br. s., 2H), 8.97 (br. s., 1H). MS obsd. (ESI$^+$) [(M+H)$^+$]: 470.

Example 26: 9-(3-hydroxy-2,2-dimethyl-propoxy)-10-methoxy-2-oxo-6-(2-thienyl)-6,7-dihydrobenzo[a]quinolizine-3-carboxylic Acid

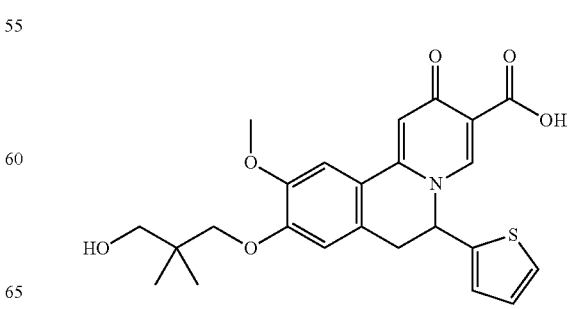

Step 1: Preparation of ethyl 9-(3-hydroxy-2,2-dimethyl-propoxy)-10-methoxy-2-oxo-6-(2-thienyl)-6,7-dihydrobenzo[a]quinolizine-3-carboxylate

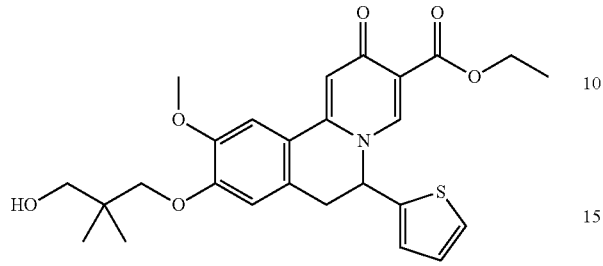

A mixture of ethyl 9-hydroxy-10-methoxy-2-oxo-6-(2-thienyl)-6,7-dihydrobenzo[a]quinolizine-3-carboxylate (100 mg, 0.25 mmol), 3-bromo-2,2-dimethyl-propan-1-ol (63 mg, 0.38 mmol) and K$_2$CO$_3$ (52 mg, 0.38 mmol) in DMF (3 ml) was heated at 80° C. 16 hrs. After being cooled to rt, the mixture was partitioned between H$_2$O and DCM. The organic layer was separated, washed with brine, dried over anhydrous Na$_2$SO$_4$ and concentrated under reduced pressure to give crude ethyl 9-(3-hydroxy-2,2-dimethyl-propoxy)-10-methoxy-2-oxo-6-(2-thienyl)-6,7-dihydrobenzo[a]quinolizine-3-carboxylate (130 mg), which was used directly in the next step without further purification.

Step 2: Preparation of 9-(3-hydroxy-2,2-dimethyl-propoxy)-10-methoxy-2-oxo-6-(2-thienyl)-6,7-dihydrobenzo[a]quinolizine-3-carboxylic Acid

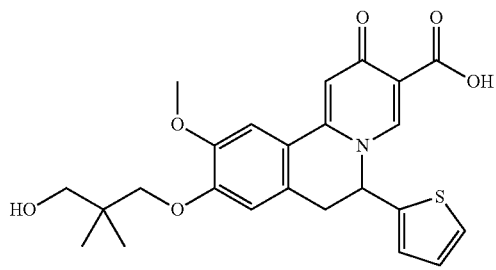 [SMILES: COc1cc2c(cc1OCC(C)(C)CO)CC(c1cccs1)n1cc(C(=O)O)c(=O)cc1-2]

A mixture of ethyl 9-(3-hydroxy-2,2-dimethyl-propoxy)-10-methoxy-2-oxo-6-(2-thienyl)-6,7-dihydrobenzo[a]quinolizine-3-carboxylate (130 mg, 0.27 mmol) and NaOH (22 mg) in H$_2$O (0.3 mL) and MeOH (2 mL) was stirred at room temperature for 16 hrs. The mixture was concentrated under reduced pressure. The residue was diluted with H$_2$O and acidified with 1 M hydrochloric acid to pH=2-3. The resulting mixture was filtered. The filter cake was purified by prep-HPLC to afford 9-(3-hydroxy-2,2-dimethyl-propoxy)-10-methoxy-2-oxo-6-(2-thienyl)-6,7-dihydrobenzo[a]quinolizine-3-carboxylic acid (52 mg) as a yellow solid. $^1$H NMR (400 MHz, DMSO-d6) δ: 0.93 (s, 6H), 3.29 (br. s., 2H), 3.32-3.33 (m, 1H), 3.66-3.74 (m, 1H), 3.74-3.79 (m, 2H), 3.88 (s, 3H), 6.34 (d, 1H), 6.90 (dd, 1H), 7.01 (d, 1H), 7.06 (s, 1H), 7.32-7.38 (m, 1H), 7.50 (d, 2H), 8.97 (s, 1H). MS obsd. (ESI$^+$) [(M+H)$^+$]: 456.

Example 27: 10-methoxy-2-oxo-6-(2-thienyl)-9-(2,2,2-trifluoroethoxy)-6,7-dihydrobenzo[a]quinolizine-3-carboxylic Acid

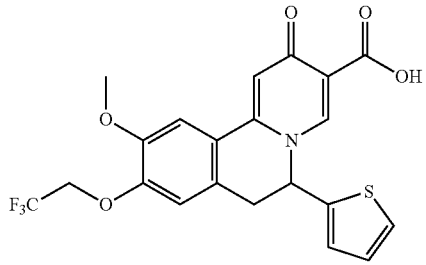 [SMILES: COc1cc2c(cc1OCC(F)(F)F)CC(c1cccs1)n1cc(C(=O)O)c(=O)cc1-2]

Step 1: Preparation of ethyl 10-methoxy-2-oxo-6-(2-thienyl)-9-(2,2,2-trifluoroethoxy)-6,7-dihydrobenzo[a]quinolizine-3-carboxylate

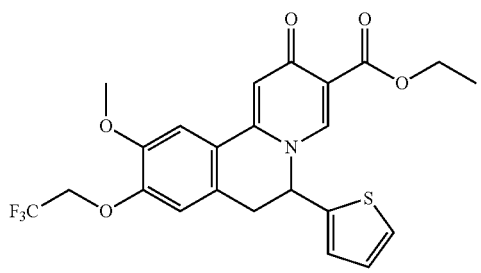 [SMILES: CCOC(=O)c1cn2c(cc1=O)-c1cc(OC)c(OCC(F)(F)F)cc1CC2c1cccs1]

A mixture of ethyl 9-hydroxy-10-methoxy-2-oxo-6-(2-thienyl)-6,7-dihydrobenzo[a]quinolizine-3-carboxylate (150 mg, 0.38 mmol), 1,1,1-trifluoro-2-iodo-ethane (119 mg, 0.57 mmol) and K$_2$CO$_3$ (78 mg, 0.57 mmol) in DMF (5 ml) was heated at 70° C. for 6 hrs. The mixture was partitioned between H$_2$O and DCM. The organic layer was separated, washed with brine, dried over anhydrous Na$_2$SO$_4$ and concentrated under reduced pressure. The residue was recrystallized from PE/EA to afford ethyl 10-methoxy-2-oxo-6-(2-thienyl)-9-(2,2,2-trifluoroethoxy)-6,7-dihydrobenzo[a]quinolizine-3-carboxylate (100 mg) as a white solid.

Step 2: Preparation of 10-methoxy-2-oxo-6-(2-thienyl)-9-(2,2,2-trifluoroethoxy)-6,7-dihydrobenzo[a]quinolizine-3-carboxylic Acid

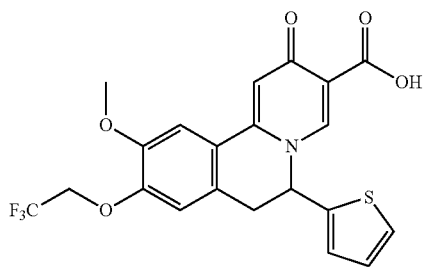 [SMILES: COc1cc2c(cc1OCC(F)(F)F)CC(c1cccs1)n1cc(C(=O)O)c(=O)cc1-2]

A mixture of ethyl 10-methoxy-2-oxo-6-(2-thienyl)-9-(2,2,2-trifluoroethoxy)-6,7-dihydrobenzo[a]quinolizine-3-carboxylate (70 mg, 0.15 mmol) and NaOH (12 mg) in H₂O (0.1 mL) and THF (2 mL) was stirred at room temperature for 16 hrs. The mixture was concentrated under reduced pressure. The residue was diluted with H₂O and acidified with 1 M hydrochloric acid to pH=2-3. The resulting mixture was filtered. The filter cake was purified by prep-HPLC to afford 10-methoxy-2-oxo-6-(2-thienyl)-9-(2,2,2-trifluoroethoxy)-6,7-dihydrobenzo[a]quinolizine-3-carboxylic acid (25 mg) as a white solid. ¹H NMR (400 MHz, DMSO-d6) δ: 3.30 (s, 1H), 3.75 (dd, 1H), 3.90 (s, 3H), 4.82 (q, 2H) 6.37 (d, 1H), 6.90 (dd, 1H), 7.02 (d, 1H), 7.21 (s, 1H), 7.32-7.42 (m, 1H), 7.60 (d, 2H), 9.02 (s, 1H). MS obsd. (ESI⁺) [(M+H)⁺]: 452.

Example 28: 10-methoxy-9-(3-morpholinopropoxy)-2-oxo-6-(2-thienyl)-6,7-dihydrobenzo[a]quinolizine-3-carboxylate

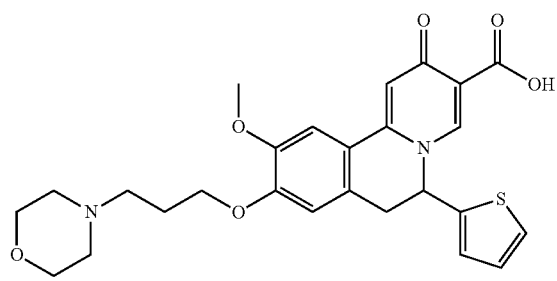 [SMILES: COc1cc2c(cc1OCCCN1CCOCC1)CC(c1cccs1)n1cc(C(=O)O)c(=O)cc1-2]

Step 1: Preparation of ethyl 10-methoxy-9-(3-morpholinopropoxy)-2-oxo-6-(2-thienyl)-6,7-dihydrobenzo[a]quinolizine-3-carboxylate

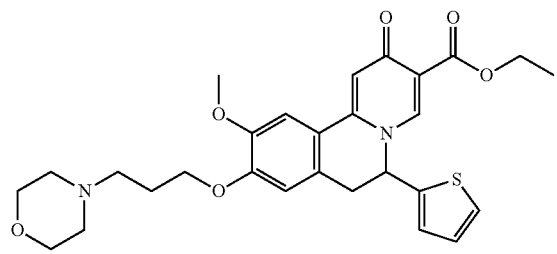 [SMILES: CCOC(=O)c1cn2c(cc1=O)-c1cc(OC)c(OCCCN3CCOCC3)cc1CC2c1cccs1]

A mixture of ethyl 9-(3-bromopropoxy)-10-methoxy-2-oxo-6-(2-thienyl)-6,7-dihydrobenzo[a]quinolizine-3-carboxylate (130 mg, 0.25 mmol, step 1 of Example 18), morpholine (109 mg, 1.25 mmol) and K₂CO₃ (173 mg, 1.25 mmol) in DMF (3 ml) was stirred at room temperature for 16 hrs. The mixture was partitioned between H₂O and DCM. The organic layer was washed with brine, dried over anhydrous Na₂SO₄ and concentrated under reduced pressure. The residue was purified by flash column chromatography to give ethyl 10-methoxy-9-(3-morpholinopropoxy)-2-oxo-6-(2-thienyl)-6,7-dihydrobenzo[a]quinolizine-3-carboxylate (100 mg) as a yellow oil.

Step 2: Preparation of 10-methoxy-9-(3-morpholinopropoxy)-2-oxo-6-(2-thienyl)-6,7-dihydrobenzo[a]quinolizine-3-carboxylate

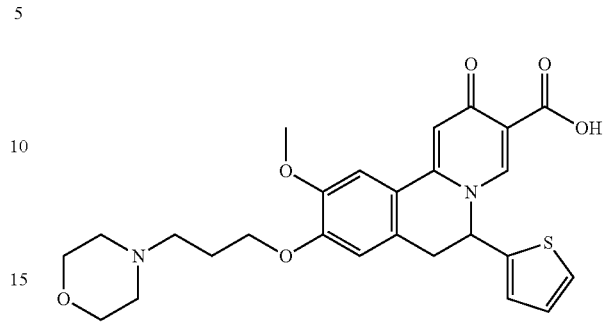

A mixture of ethyl 10-methoxy-9-(3-morpholinopropoxy)-2-oxo-6-(2-thienyl)-6,7-dihydrobenzo[a]quinolizine-3-carboxylate (100 mg, 0.27 mmol) and NaOH (15 mg) in MeOH (2 mL) and H₂O (0.2 mL) was stirred at room temperature for 16 hrs. The mixture was concentrated under reduced pressure. The residue was diluted with H₂O and acidified with 1 M hydrochloric acid to pH=2-3. The resulting mixture was filtered. The filter cake was purified by prep-HPLC to afford 10-methoxy-9-(3-morpholinopropoxy)-2-oxo-6-(2-thienyl)-6,7-dihydrobenzo[a]quinolizine-3-carboxylate (7 mg) as a white solid. ¹H NMR (400 MHz, DMSO-d6) δ: 1.90 (quin, 2H), 2.35 (m, 4H), 2.41 (t, 2H), 3.33 (m, 1H), 3.56 (t, 4H), 3.70 (dd, 1H), 3.87 (s, 3H), 4.07 (t, 2H), 6.32 (m, 1H), 6.91 (dd, 1H), 6.97-7.13 (m, 2H), 7.29-7.40 (m, 1H), 7.45-7.54 (m, 1H), 8.33 (s, 1H), 8.94 (s, 1H). MS obsd. (ESI⁺) [(M+H)⁺]: 497.

Example 29: 10-methoxy-2-oxo-6-(2-thienyl)-9-[3-(1,2,4-triazol-1-yl)propoxy]-6,7-dihydrobenzo[a]quinolizine-3-carboxylic Acid

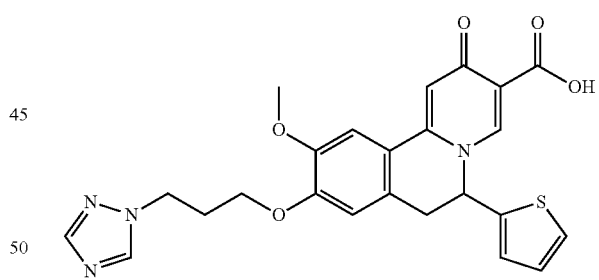

Step 1: Preparation of 1-(3-bromopropyl)-1,2,4-triazole

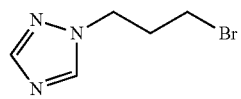

To a solution of 1H-1,2,4-triazole (1 g, 14.5 mmol) in DMF (10 mL) was added NaH (596 mg, 14.9 mmol) and the mixture was stirred for 15 min. Then to the mixture was added 1,3-dibromopropane (14.6 g, 72.4 mmol). The resulting mixture was stirred at 30° C. for 12 hrs, and then partitioned between H₂O (150 mL) and EtOAc (200 mL). The organic layer was separated, washed with brine (150 mL), dried over anhydrous Na₂SO₄ and concentrated under reduced pressure. The residue was purified by column chromatography to afford crude 1-(3-bromopropyl)-1,2,4-triazole (300 mg) as a yellow oil.

Step 2: Preparation of ethyl 10-methoxy-2-oxo-6-(2-thienyl)-9-[3-(1,2,4-triazol-1-yl)propoxy]-6,7-dihydrobenzo[a]quinolizine-3-carboxylate

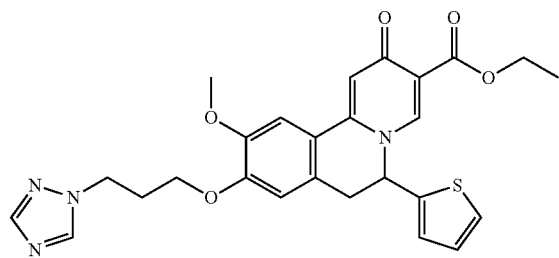 [SMILES: CCOC(=O)c1cn2c(cc1=O)-c1cc(OC)c(OCCCn3cncn3)cc1CC2c1cccs1]

To a solution of ethyl 9-hydroxy-10-methoxy-2-oxo-6-(2-thienyl)-6,7-dihydrobenzo[a]quinolizine-3-carboxylate (150 mg, 0.377 mmol) in DMF (3 mL) was added K₂CO₃ (104 mg, 754 μmol) and 1-(3-bromopropyl)-1,2,4-triazole (107 mg, 0.566 mmol). The mixture was stirred at 30° C. for 12 hrs, and then partitioned between H₂O (50 mL) and EtOAc (100 mL). The organic layer was washed with brine (50 mL), dried over anhydrous Na₂SO₄ and concentrated under reduced pressure to afford crude ethyl 10-methoxy-2-oxo-6-(2-thienyl)-9-[3-(1,2,4-triazol-1-yl)propoxy]-6,7-dihydrobenzo[a]quinolizine-3-carboxylate (200 mg) as a brown oil, which was used directly in the next step without further purification.

Step 3: Preparation of 10-methoxy-2-oxo-6-(2-thienyl)-9-[3-(1,2,4-triazol-1-yl)propoxy]-6,7-dihydrobenzo[a]quinolizine-3-carboxylic Acid

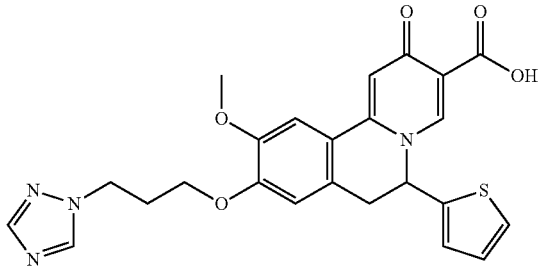 [SMILES: COc1cc2c(cc1OCCCn1cncn1)CC(c1cccs1)n1cc(C(=O)O)c(=O)cc1-2]

To a solution of ethyl 10-methoxy-2-oxo-6-(2-thienyl)-9-[3-(1,2,4-triazol-1-yl)propoxy]-6,7-dihydrobenzo[a]quinolizine-3-carboxylate (200 mg, 0.395 mmol) in MeOH (2 mL) was added 2 M NaOH aqueous solution (0.395 mL, 0.790 mmol). The mixture was stirred at 30° C. for 12 hrs, and then concentrated under reduced pressure. The residue was diluted with H₂O (20 mL) and acidified with 1 M hydrochloric acid to pH=3. The resulting mixture was extracted with DCM (100 mL). The organic layer was washed with brine (50 mL), dried over anhydrous Na₂SO₄ and concentrated under reduced pressure. The residue was purified by prep-HPLC to afford 10-methoxy-2-oxo-6-(2-thienyl)-9-[3-(1,2,4-triazol-1-yl)propoxy]-6,7-dihydrobenzo[a]quinolizine-3-carboxylic acid (61 mg) as a white solid. ¹H NMR (400 MHz, DMSO-d6) δ: 2.28 (t, 2H), 3.23-3.31 (m, 1H), 3.71 (dd, 1H), 3.90 (s, 3H), 4.05 (d, 2H), 4.35 (t, 2H), 6.34 (d, 1H), 6.91 (dd, 1H), 6.99-7.08 (m, 2H), 7.36 (dd, 1H), 7.53 (d, 2H), 7.98 (s, 1H), 8.53 (s, 1H), 8.99 (s, 1H). MS obsd. (ESI⁺) [(M+H)⁺]: 479.

Example 30: 9-(3-carboxypropoxy)-10-methoxy-2-oxo-6-(2-thienyl)-6,7-dihydrobenzo[a]quinolizine-3-carboxylic Acid

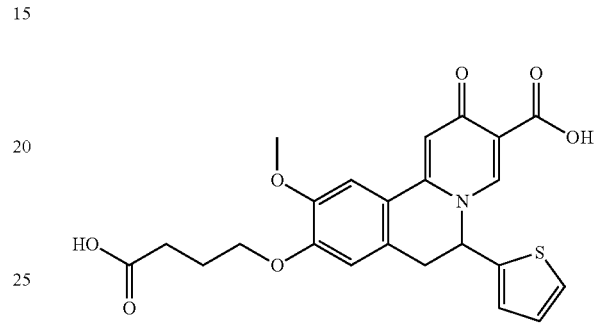

Step 1: Preparation of ethyl 9-(4-ethoxy-4-oxo-butoxy)-10-methoxy-2-oxo-6-(2-thienyl)-6,7-dihydrobenzo[a]quinolizine-3-carboxylate

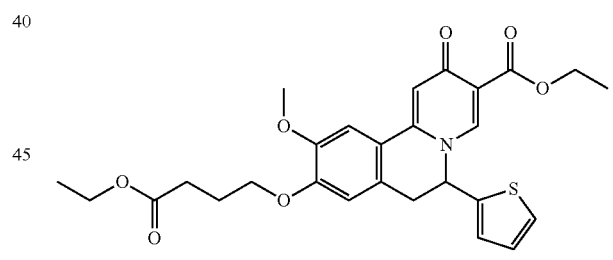

A mixture of ethyl 9-hydroxy-10-methoxy-2-oxo-6-(2-thienyl)-6,7-dihydrobenzo[a]quinolizine-3-carboxylate (100 mg, 0.25 mmol), ethyl 4-bromobutanoate (74 mg, 0.38 mmol) and K₂CO₃ (52 mg, 0.38 mmol) in DMF (3 mL) was stirred at room temperature for 16 hrs. The mixture was partitioned between H₂O and DCM. The organic layer was separated, washed with brine, dried over anhydrous Na₂SO₄ and concentrated under reduced pressure. The residue was recrystallized from PE/EA to afford ethyl 9-(4-ethoxy-4-oxo-butoxy)-10-methoxy-2-oxo-6-(2-thienyl)-6,7-dihydrobenzo[a]quinolizine-3-carboxylate (60 mg) as a white solid.

Step 2: Preparation of 9-(3-carboxypropoxy)-10-methoxy-2-oxo-6-(2-thienyl)-6,7-dihydrobenzo[a]quinolizine-3-carboxylic Acid

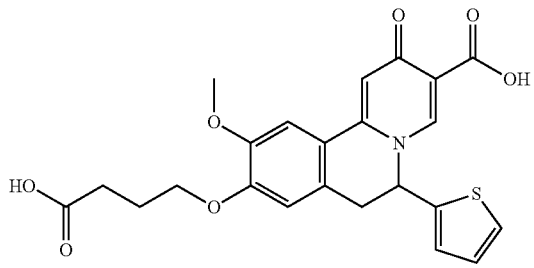 [SMILES: COc1cc2c(cc1OCCCC(=O)O)CC(c1cccs1)n1cc(C(=O)O)c(=O)cc1-2]

A mixture of ethyl 9-(4-ethoxy-4-oxo-butoxy)-10-methoxy-2-oxo-6-(2-thienyl)-6,7-dihydrobenzo[a]quinolizine-3-carboxylate (60 mg, 0.12 mmol) and NaOH (20 mg) in MeOH (2 mL) and H₂O (0.1 mL) was stirred at room temperature for 16 hrs. The mixture was concentrated under reduced pressure. The residue was diluted with H₂O and acidified with 1 M hydrochloric acid to pH=2-3. The resulting mixture was filtered, and the filter cake was dried under reduced pressure to afford 9-(3-carboxypropoxy)-10-methoxy-2-oxo-6-(2-thienyl)-6,7-dihydrobenzo[a]quinolizine-3-carboxylic acid (26 mg) as a white solid. $^1$H NMR (400 MHz, DMSO-d6) δ: 1.96 (t, 2H), 2.39 (t, 2H), 3.36 (m, 1H), 3.71 (d, 1H), 3.88 (s, 3H), 4.05 (br. s., 2H), 6.35 (br. s., 1H), 6.90 (br. s., 1H), 7.05 (d, 2H), 7.35 (d, 1H), 7.51 (d, 2H), 8.98 (s, 1H), 12.17 (br. s., 1H). MS obsd. (ESI⁺) [(M+H)⁺]: 456.

Example 31: 10-methoxy-9-(3-methylsulfanylpropoxy)-2-oxo-6-(2-thienyl)-6,7-dihydrobenzo[a]quinolizine-3-carboxylic Acid

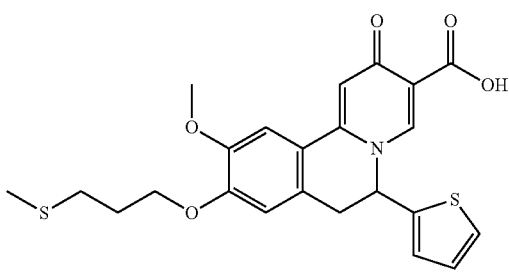 [SMILES: COc1cc2c(cc1OCCCSC)CC(c1cccs1)n1cc(C(=O)O)c(=O)cc1-2]

Step 1: Preparation of 3-methylsulfanylpropyl methanesulfonate

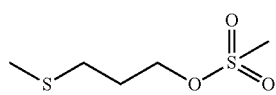

To a solution of 3-methylsulfanylpropan-1-ol (500 mg, 4.71 mmol) in DCM (5 mL) was added Et₃N (2.38 g, 23.5 mmol) and methanesulfonyl chloride (2.86 g, 25.0 mmol). The mixture was stirred at 30° C. for 12 hrs, and then partitioned between H₂O (20 mL) and DCM (60 mL). The organic layer was separated, washed with brine (50 mL), dried over anhydrous Na₂SO₄ and concentrated under reduced pressure to afford crude 3-methylsulfanylpropyl methanesulfonate (600 mg) as a yellow oil, which was used directly in the next step without further purification.

Step 2: Preparation of ethyl 10-methoxy-9-(3-methylsulfanylpropoxy)-2-oxo-6-(2-thienyl)-6,7-dihydrobenzo[a]quinolizine-3-carboxylate

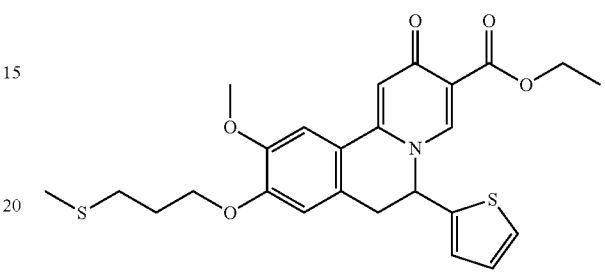

To a solution of ethyl 9-hydroxy-10-methoxy-2-oxo-6-(2-thienyl)-6,7-dihydrobenzo[a]quinolizine-3-carboxylate (100 mg, 0.251 mmol) in DMF (3 mL) was added K₂CO₃ (69.6 mg, 0.503 mmol) and 3-methylsulfanylpropyl methanesulfonate (69.6 mg, 0.377 mmol). Then the mixture was stirred at 30° C. for 12 hrs, and then partitioned between H₂O (50 mL) and EtOAc (100 mL). The organic layer was separated, washed with brine (50 mL), dried over anhydrous Na₂SO₄ and concentrated under reduced pressure to afford crude ethyl 10-methoxy-9-(3-methylsulfanylpropoxy)-2-oxo-6-(2-thienyl)-6,7-dihydrobenzo[a]quinolizine-3-carboxylate (120 mg) as a yellow oil, which was used directly in the next step without further purification.

Step 3: Preparation of 10-methoxy-9-(3-methylsulfanylpropoxy)-2-oxo-6-(2-thienyl)-6,7-dihydrobenzo[a]quinolizine-3-carboxylic Acid

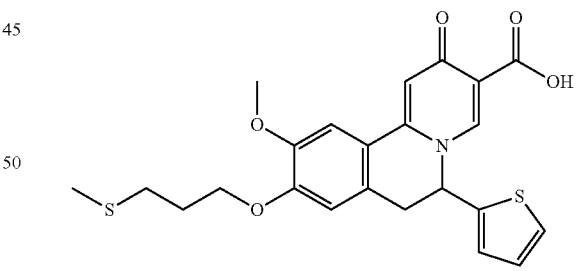

To a solution of ethyl 10-methoxy-9-(3-methylsulfanylpropoxy)-2-oxo-6-(2-thienyl)-6,7-dihydrobenzo[a]quinolizine-3-carboxylate (120 mg, 0.247 mmol) in MeOH (1 mL) was added 2 M NaOH aqueous solution (0.247 mL, 0.494 mmol). The mixture was stirred at 30° C. for 2 hrs, and then concentrated under reduced pressure. The residue was diluted with H₂O (20 mL) and acidified with 1 M hydrochloric acid to pH=3. Then the resulting mixture was extracted with DCM (60 mL).

The organic layer was washed with brine (50 mL), dried over anhydrous Na₂SO₄ and concentrated under reduced pressure. The residue was purified by prep-HPLC to afford 10-methoxy-9-(3-methylsulfanylpropoxy)-2-oxo-6-(2-thienyl)-6,7-dihydrobenzo[a]quinolizine-3-carboxylic acid (14.9 mg) as a white solid. ¹H NMR (400 MHz, DMSO-d6) δ:1.94-2.03 (m, 2H), 2.04-2.10 (m, 3H), 2.61 (t, 2H), 3.41-3.52 (m, 1H), 3.72 (dd, 1H), 3.88 (s, 3H), 4.11 (t, 2H), 6.34 (d, 1H), 6.90 (dd, 1H), 6.99-7.15 (m, 2H), 7.36 (dd, 1H), 7.51 (d, 2H), 8.98 (s, 1H). MS obsd. (ESI⁺) [(M+H)⁺]: 458.

Example 32: 10-methoxy-9-(3-methylsulfonylpropoxy)-2-oxo-6-(2-thienyl)-6,7-dihydrobenzo[a]quinolizine-3-carboxylic Acid

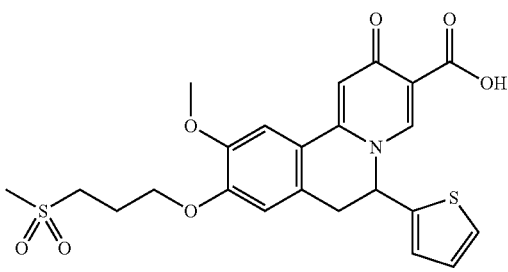 [SMILES: COc1cc2c(cc1OCCCS(C)(=O)=O)CC(c1cccs1)n1cc(C(=O)O)c(=O)cc1-2]

Step 1: Preparation of 3-methylsulfonylpropyl methanesulfonate

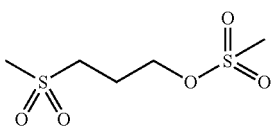

To a solution of 3-methylsulfonylpropan-1-ol (200 mg, 1.45 mmol) in DCM (5 mL) was added Et₃N (732 mg, 23.5 mmol) and methanesulfonyl chloride (2.84 g, 24.9 mmol). The mixture was stirred at 30° C. for 12 hrs, and then partitioned between H₂O (20 mL) and DCM (60 mL). The organic layer was separated, washed with brine (50 mL), dried over anhydrous Na₂SO₄ and concentrated under reduced pressure to afford crude 3-methylsulfonylpropyl methanesulfonate (300 mg) as a yellow oil, which was used directly in the next step without further purification.

Step 2: Preparation of ethyl 10-methoxy-9-(3-methylsulfonylpropoxy)-2-oxo-6-(2-thienyl)-6,7-dihydrobenzo[a]quinolizine-3-carboxylate

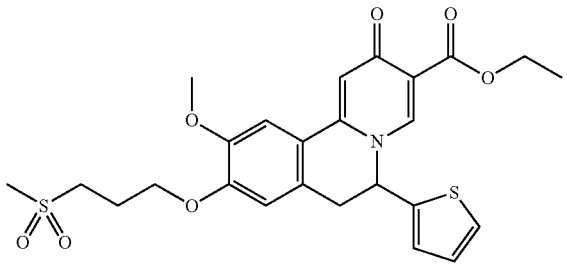 [SMILES: CCOC(=O)c1cn2c(cc1=O)-c1cc(OC)c(OCCCS(C)(=O)=O)cc1CC2c1cccs1]

To a solution of ethyl 9-hydroxy-10-methoxy-2-oxo-6-(2-thienyl)-6,7-dihydrobenzo[a]quinolizine-3-carboxylate (100 mg, 0.251 mmol) in DMF (3 mL) was added K₂CO₃ (69.6 mg, 0.503 mmol) and 3-methylsulfonylpropyl methanesulfonate (81.6 mg, 0.377 mmol). The mixture was stirred at 30° C. for 12 hrs, and then partitioned between H₂O (50 mL) and EtOAc (100 mL). The organic layer was separated, washed with brine (50 mL), dried over anhydrous Na₂SO₄ and concentrated under reduced pressure to afford crude ethyl 10-methoxy-9-(3-methylsulfonylpropoxy)-2-oxo-6-(2-thienyl)-6,7-dihydrobenzo[a]quinolizine-3-carboxylate (90 mg) as a yellow oil, which was used directly in the next step without further purification.

Step 3: Preparation of 10-methoxy-9-(3-methylsulfonylpropoxy)-2-oxo-6-(2-thienyl)-6,7-dihydrobenzo[a]quinolizine-3-carboxylic Acid

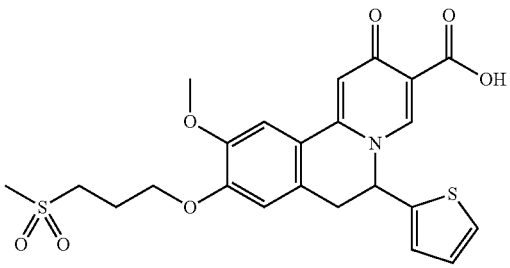 [SMILES: COc1cc2c(cc1OCCCS(C)(=O)=O)CC(c1cccs1)n1cc(C(=O)O)c(=O)cc1-2]

To a solution of ethyl 10-methoxy-9-(3-methylsulfonylpropoxy)-2-oxo-6-(2-thienyl)-6,7-dihydrobenzo[a]quinolizine-3-carboxylate (90 mg, 0.174 mmol) in MeOH (1 mL) was added 2 M NaOH aqueous solution (0.174 mL, 0.348 mmol). The mixture was stirred at 30° C. for 2 hrs, and then concentrated under reduced pressure. The residue was diluted with H₂O (20 mL) and acidified with 1 M hydrochloric acid to pH=3. The resulting mixture was extracted with DCM (60 mL). The organic layer was washed with brine (50 mL), dried over anhydrous Na₂SO₄ and concentrated under reduced pressure. The residue was purified by prep-HPLC to afford 10-methoxy-9-(3-methyl sulfonylpropoxy)-2-oxo-6-(2-thienyl)-6,7-dihydrobenzo[a]quinolizine-3-carboxylic acid (14.4 mg) as a yellow solid. ¹H NMR (400 MHz, DMSO-d6) δ: 2.12-2.25 (m, 2H) 3.03 (s, 3H), 3.23-3.30 (m, 2H), 3.34 (br. s., 1H), 3.72 (dd, 1H), 3.89 (s, 3H), 4.16 (t, 2H), 6.35 (br. s., 1H), 6.86-6.94 (m, 1H), 6.97-7.13 (m, 2H), 7.35 (d, 1H), 7.52 (d, 2H), 8.98 (s, 1H). MS obsd. (ESI⁺) [(M+H)⁺]: 490.

Example 33: 10-methoxy-9-methyl-2-oxo-6-(2-thienyl)-6,7-dihydrobenzo[a]quinolizine-3-carboxylic Acid

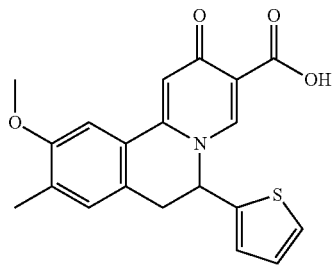 [SMILES: COc1cc2c(cc1C)CC(c1cccs1)n1cc(C(=O)O)c(=O)cc1-2]

Step 1: Preparation of ethyl 10-methoxy-2-oxo-6-(2-thienyl)-9-(trifluoromethylsulfonyloxy)-6,7-dihydrobenzo[a]quinolizine-3-carboxylate

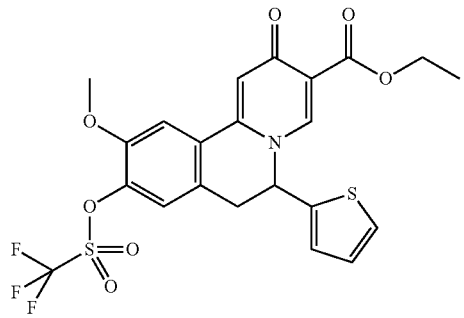 [SMILES: CCOC(=O)c1cn2c(cc1=O)-c1cc(OC)c(OS(=O)(=O)C(F)(F)F)cc1CC2c1cccs1]

To a stirred solution of ethyl 9-hydroxy-10-methoxy-2-oxo-6-(2-thienyl)-6,7-dihydrobenzo[a]quinolizine-3-carboxylate (1.5 g, 3.77 mmol) and Et₃N (1.15 g, 11.32 mmol) in DCM (15 mL) was added a solution of N-phenyl-bis(trifluoromethanesulfonimide) (2.0 g, 5.66 mmol) in DCM (10 mL) drop wise at 0° C. The mixture was warmed up to rt, and stirred at rt for 16 hrs. The reaction mixture was diluted with DCM, and washed with 1 M hydrochloric acid and brine. The organic phase was dried over anhydrous Na₂SO₄ and concentrated under reduced pressure. The residue was purified by column chromatography to afford ethyl 10-methoxy-2-oxo-6-(2-thienyl)-9-(trifluoromethyl sulfonyloxy)-6,7-dihydrobenzo[a]quinolizine-3-carboxylate (1.55 g) as a yellow solid.

Step 2: Preparation of ethyl 10-methoxy-9-methyl-2-oxo-6-(2-thienyl)-6,7-dihydrobenzo[a]quinolizine-3-carboxylate

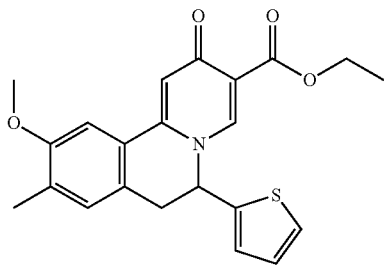 [SMILES: CCOC(=O)c1cn2c(cc1=O)-c1cc(OC)c(C)cc1CC2c1cccs1]

A mixture of ethyl 10-methoxy-2-oxo-6-(2-thienyl)-9-(trifluoromethylsulfonyloxy)-6,7-dihydrobenzo[a]quinolizine-3-carboxylate (200 mg, 0.38 mmol), methylboronic acid (34 mg, 0.57 mmol), K₂CO₃ (157 mg, 1.13 mmol) and Pd(dppf)Cl₂·CH₂Cl₂ (31 mg, 0.04 mmol) in THF/H₂O (4 mL/1 mL) was heated at 60° C. for 12 hrs under nitrogen atmosphere. The mixture was concentrated under reduced pressure, and the residue was purified by flash column chromatography to afford crude ethyl 10-methoxy-9-methyl-2-oxo-6-(2-thienyl)-6,7-dihydrobenzo[a]quinolizine-3-carboxylate (310 mg) as a dark yellow solid, which was used directly in the next step without further purification.

Step 3: Preparation of 10-methoxy-9-methyl-2-oxo-6-(2-thienyl)-6,7-dihydrobenzo[a]quinolizine-3-carboxylic Acid

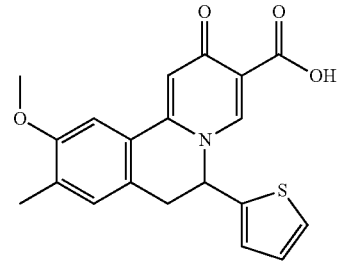 [SMILES: COc1cc2c(cc1C)CC(c1cccs1)n1cc(C(=O)O)c(=O)cc1-2]

A mixture of ethyl 10-methoxy-9-methyl-2-oxo-6-(2-thienyl)-6,7-dihydrobenzo[a]quinolizine-3-carboxylate (310 mg, 0.78 mmol) and NaOH (63 mg) in MeOH (3 mL) and H₂O (0.8 mL) was stirred at room temperature for 16 hrs. The mixture was concentrated under reduced pressure. The residue was diluted with H₂O and acidified with 1 M hydrochloric acid to pH=2-3. The resulting mixture was filtered. The filter cake was purified by prep-HPLC to afford 10-methoxy-9-methyl-2-oxo-6-(2-thienyl)-6,7-dihydrobenzo[a]quinolizine-3-carboxylic acid (26 mg) as a light yellow solid. ¹H NMR (400 MHz, DMSO-d6) δ: 2.20 (s, 3H), 3.31 (m, 1H), 3.68-3.71 (m, 1H), 3.91 (s, 3H), 6.37 (br. s., 1H), 6.90 (dd, 1H), 7.00 (br. s., 1H), 7.24 (s, 1H), 7.36 (d, 1H), 7.50 (s, 1H) 7.62 (s, 1H), 9.02 (s, 1H). MS obsd. (ESI⁺) [(M+H)⁺]: 368.

Example 34: 9-ethyl-10-methoxy-2-oxo-6-(2-thienyl)-6,7-dihydrobenzo[a]quinolizine-3-carboxylic Acid

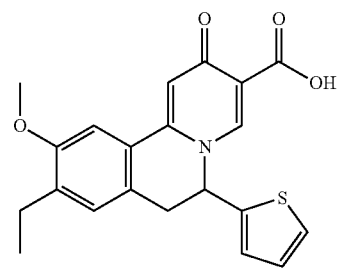

Step 1: Preparation of ethyl 9-ethyl-10-methoxy-2-oxo-6-(2-thienyl)-6,7-dihydrobenzo[a]quinolizine-3-carboxylate

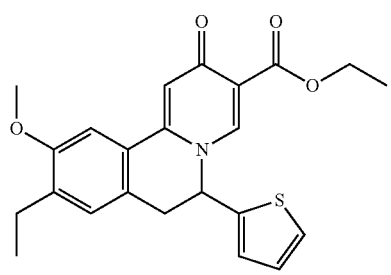

A mixture of ethyl 10-methoxy-2-oxo-6-(2-thienyl)-9-(trifluoromethylsulfonyloxy)-6,7-dihydrobenzo[a]quinolizine-3-carboxylate (200 mg, 0.38 mmol, from step 1 of Example 33), ethylboronic acid (42 mg, 0.57 mmol), K$_2$CO$_3$ (157 mg, 1.13 mmol) and Pd(dppf)Cl$_2$·CH$_2$Cl$_2$ (31 mg, 0.04 mmol) in THF/H$_2$O (4 mL/1 mL) was heated at 60° C. for 12 hrs under nitrogen atmosphere. The mixture was concentrated under reduced pressure. The residue was purified by flash column chromatography to afford crude ethyl 9-ethyl-10-methoxy-2-oxo-6-(2-thienyl)-6,7-dihydrobenzo[a]quinolizine-3-carboxylate (140 mg) as a yellow oil, which was used directly in the next step without further purification.

Step 2: Preparation of 9-ethyl-10-methoxy-2-oxo-6-(2-thienyl)-6,7-dihydrobenzo[a]quinolizine-3-carboxylic Acid

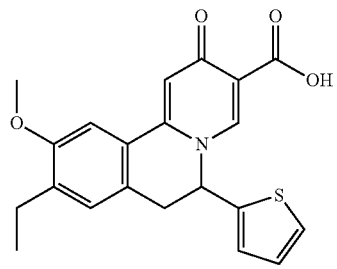

A mixture of ethyl 9-ethyl-10-methoxy-2-oxo-6-(2-thienyl)-6,7-dihydrobenzo[a]quinolizine-3-carboxylate (140 mg, 0.34 mmol) and NaOH (27 mg) in H$_2$O (0.3 mL) and MeOH (2 mL) was stirred at room temperature for 16 hrs. The mixture was concentrated under reduced pressure. The residue was diluted with H$_2$O and acidified with 1 M hydrochloric acid to pH=2-3. The resulting mixture was filtered. The filter cake was purified by prep-HPLC to afford 9-ethyl-10-methoxy-2-oxo-6-(2-thienyl)-6,7-dihydrobenzo[a]quinolizine-3-carboxylic acid (21 mg) as a light yellow solid. $^1$H NMR (400 MHz, DMSO-d6) δ: 1.15 (t, 3H), 2.55-2.71 (m, 2H), 3.37 (m, 1H), 3.68-3.73 (m, 1H), 3.92 (s, 3H), 6.37 (br. s., 1H), 6.91 (dd, 1H), 7.01 (br. s., 1H), 7.24 (s, 1H), 7.36 (d, 1H), 7.51 (s, 1H), 7.62 (s, 1H), 9.02 (s, 1H). MS obsd. (ESI$^+$) [(M+H)$^+$]: 382.

Example 35: 10-methoxy-2-oxo-9-propyl-6-(2-thienyl)-6,7-dihydrobenzo[a]quinolizine-3-carboxylic Acid

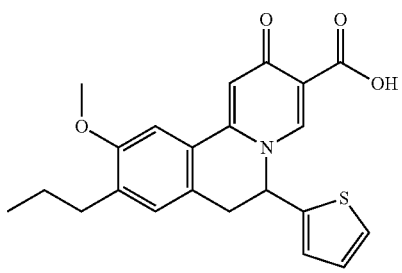 [SMILES: CCCc1cc2c(cc1OC)-c1cc(=O)c(C(=O)O)cn1C(c1cccs1)C2]

Step 1: Preparation of ethyl 10-methoxy-2-oxo-9-propyl-6-(2-thienyl)-6,7-dihydrobenzo[a]quinolizine-3-carboxylate

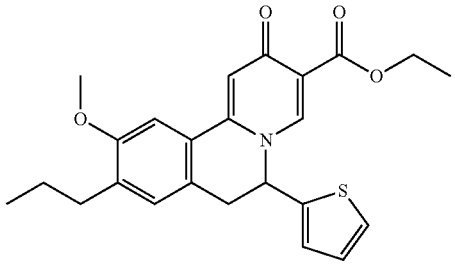 [SMILES: CCCc1cc2c(cc1OC)-c1cc(=O)c(C(=O)OCC)cn1C(c1cccs1)C2]

A mixture of ethyl 10-methoxy-2-oxo-6-(2-thienyl)-9-(trifluoromethylsulfonyloxy)-6,7-dihydrobenzo[a]quinolizine-3-carboxylate (200 mg, 0.38 mmol), propylboronic acid (50 mg, 0.57 mmol), K$_2$CO$_3$ (157 mg, 1.13 mmol) and Pd(dppf)Cl$_2$·CH$_2$Cl$_2$ (31 mg, 0.04 mmol) in THF/H$_2$O (4 mL/1 mL) was heated at 70° C. for 12 hrs under nitrogen atmosphere. The mixture was concentrated under reduced pressure. The residue was purified by flash column chromatography to afford crude ethyl 10-methoxy-2-oxo-9-propyl-6-(2-thienyl)-6,7-dihydrobenzo[a]quinolizine-3-carboxylate (100 mg) as a brown solid, which was used directly in the next step without further purification.

Step 2: Preparation of 10-methoxy-2-oxo-9-propyl-6-(2-thienyl)-6,7-dihydrobenzo[a]quinolizine-3-carboxylic Acid

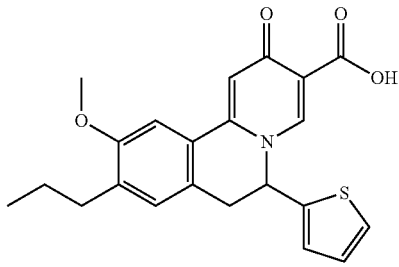 [SMILES: CCCc1cc2c(cc1OC)-c1cc(=O)c(C(=O)O)cn1C(c1cccs1)C2]

A mixture of ethyl 10-methoxy-2-oxo-9-propyl-6-(2-thienyl)-6,7-dihydrobenzo[a]quinolizine-3-carboxylate (100 mg, 0.24 mmol) and NaOH (19 mg) in H$_2$O (0.2 mL) and MeOH (2 mL) was stirred at room temperature for 16 hrs. The mixture was concentrated under reduced pressure. The residue was diluted with H$_2$O and acidified with 1 M hydrochloric acid to pH=2-3. The resulting mixture was filtered. The filter cake was purified by prep-HPLC to afford 10-methoxy-2-oxo-9-propyl-6-(2-thienyl)-6,7-dihydrobenzo[a]quinolizine-3-carboxylic acid (15 mg) as a white solid. $^1$H NMR (400 MHz, DMSO-d6) δ: 0.89 (t, 3H), 1.56 (sxt, 2H), 2.53-2.62 (m, 2H), 3.31-3.33 (m, 1H), 3.65-3.74 (m, 1H), 3.90 (s, 3H), 6.36 (br. s., 1H), 6.90 (dd, H), 7.02 (br. s., 1H), 7.21 (s, 1H), 7.35 (d, 1H), 7.50 (s, 1H), 7.61 (s, 1H), 9.02 (s, 1H). MS obsd. (ESI$^+$) [(M+H)$^+$]: 396.

Example 36: 10-methoxy-2-oxo-9-pyrrolidin-1-yl-6-(2-thienyl)-6,7-dihydrobenzo[a]quinolizine-3-carboxylic Acid

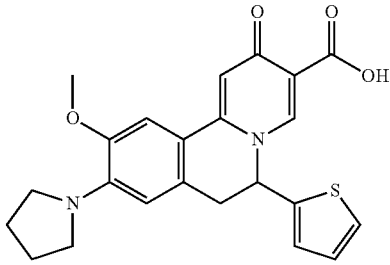 [SMILES: COc1cc2c(cc1N1CCCC1)CC(c1cccs1)n1cc(C(=O)O)c(=O)cc1-2]

Step 1: Preparation of ethyl 10-methoxy-2-oxo-9-pyrrolidin-1-yl-6-(2-thienyl)-6,7-dihydrobenzo[a]quinolizine-3-carboxylate

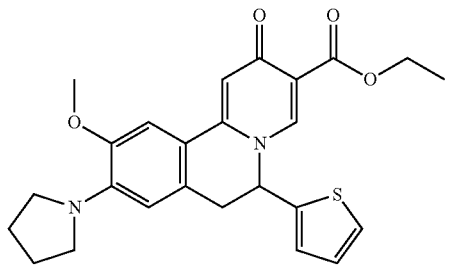 [SMILES: CCOC(=O)c1cn2c(cc1=O)-c1cc(OC)c(N3CCCC3)cc1CC2c1cccs1]

To a solution of ethyl 10-methoxy-2-oxo-6-(2-thienyl)-9-(trifluoromethylsulfonyloxy)-6,7-dihydrobenzo[a]quinolizine-3-carboxylate (100 mg, 0.189 mmol) in NMP (20 mL) was added pyrrolidine (67 mg, 0.944 mmol). The reaction vessel was sealed and heated in microwave reactor at 150° C. for 1 hr. Then the resulting mixture was purified by column chromatography to give crude product (3 g) as yellow oil, which was partitioned between H$_2$O (50 mL) and EtOAc (100 mL). The organic layer was separated, washed with brine (50 mL), dried over anhydrous Na$_2$SO$_4$ and concentrated under reduced pressure to afford ethyl 10-methoxy-2-oxo-9-pyrrolidin-1-yl-6-(2-thienyl)-6,7-dihydrobenzo[a]quinolizine-3-carboxylate (60 mg) as a brown oil, which was used directly in the next step without further purification.

Step 2: Preparation of 10-methoxy-2-oxo-9-pyrrolidin-1-yl-6-(2-thienyl)-6,7-dihydrobenzo[a]quinolizine-3-carboxylic Acid

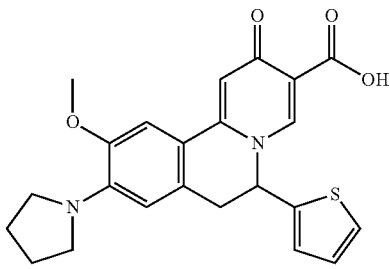 [SMILES: COc1cc2c(cc1N1CCCC1)CC(c1cccs1)n1cc(C(=O)O)c(=O)cc1-2]

To a solution of ethyl 10-methoxy-2-oxo-9-pyrrolidin-1-yl-6-(2-thienyl)-6,7-dihydrobenzo[a]quinolizine-3-carboxylate (60 mg, 0.133 mmol) in MeOH (1 mL) was added 2 M NaOH (0.2 mL, 0.399 mmol). The resulting mixture was stirred at 30° C. for 0.5 hr, and then concentrated under reduced pressure. The residue was diluted with H$_2$O (20 mL) and acidified with 1 M hydrochloric acid to pH=3. The resulting mixture was extracted with DCM (60 mL). The organic layer was washed with brine (50 mL), dried over anhydrous Na$_2$SO$_4$ and concentrated under reduced pressure. The residue was purified by prep-HPLC to afford 10-methoxy-2-oxo-9-pyrrolidin-1-yl-6-(2-thienyl)-6,7-dihydrobenzo[a]quinolizine-3-carboxylic acid (13.8 mg) as a yellow solid. $^1$H NMR (400 MHz, DMSO-d6) δ: 1.78-1.92 (m, 4H), 3.24 (br. s., 1H) 3.44 (d, 4H), 3.63 (dd, 1H), 3.84 (s, 3H), 6.29 (d, 1H), 6.54 (s, 1H), 6.91 (dd, 1H), 7.02 (d, 1H), 7.26-7.42 (m, 3H), 8.90 (s, 1H). MS obsd. (ESI$^+$) [(M+H)$^+$]: 423.

Example 37: 6-(benzothiophen-2-yl)-10-chloro-9-(3-methoxypropoxy)-2-oxo-6,7-dihydrobenzo[a]quinolizine-3-carboxylic Acid

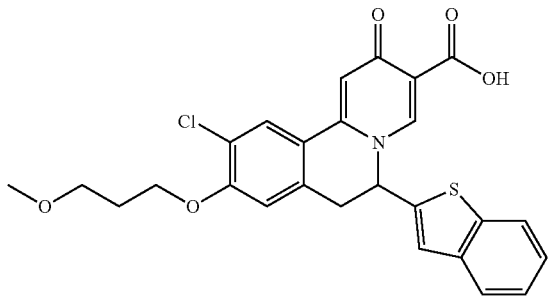 [SMILES: COCCCOc1cc2c(cc1Cl)-c1cc(=O)c(C(=O)O)cn1C(c1cc3ccccc3s1)C2]

Step 1: Preparation of 4-bromo-1-chloro-2-(3-methoxypropoxy)benzene

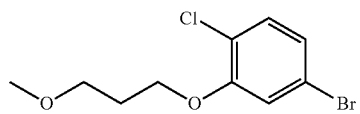

A mixture of 5-bromo-2-chloro-phenol (22.0 g, 106 mmol), 1-bromo-3-methoxy-propane (19.5 g, 127 mmol) and K$_2$CO$_3$ (30 g, 212 mmol) in DMF (50 mL) was heated at 50° C. for 3 hrs. Then the mixture was partitioned between ethyl acetate and water. The organic layer was separated, dried over anhydrous Na$_2$SO$_4$ and concentrated under reduced pressure to give crude 4-bromo-1-chloro-2-(3-methoxypropoxy)benzene (30.0 g), which was used directly in the next step without further purification.

Step 2: Preparation of 1-(benzothiophen-2-yl)-2-[4-chloro-3-(3-methoxypropoxy)phenyl]ethanone

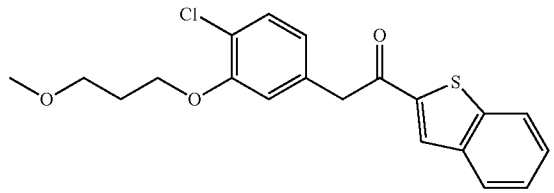 [SMILES: COCCCOc1cc(CC(=O)c2cc3ccccc3s2)ccc1Cl]

To a mixture of crude 4-bromo-1-chloro-2-(3-methoxypropoxy)benzene (1.11 g, 4 mmol), tris(dibenzylideneacetone)dipalladium(0) (37 mg, 0.04 mmol), Xantphos (46 mg, 0.08 mmol) and t-BuONa (768 mg, 8 mmol) in THF (10 mL) was added 1-(benzothiophen-2-yl)ethanone (1.41 g, 8 mmol). The resulting mixture was heated at 60° C. for 30 minutes under microwave. After being cooled to rt, the mixture was partitioned between water and EtOAc. The separated aqueous layer was extracted with EtOAc for three times. The combined organic layers were washed with brine, dried over anhydrous $Na_2SO_4$, and concentrated under reduced pressure. The residue was purified by column chromatography to afford 1-(benzothiophen-2-yl)-2-[4-chloro-3-(3-methoxypropoxy)phenyl]ethanone (1.41 g) as a brown oil.

Step 3: Preparation of 1-(benzothiophen-2-yl)-2-[4-chloro-3-(3-methoxypropoxy)phenyl]ethanamine

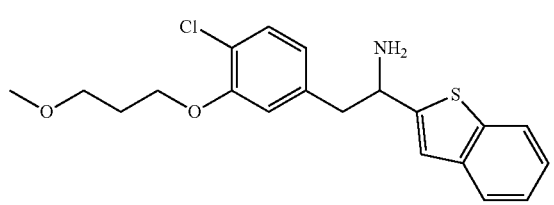 [SMILES: COCCCOc1cc(CC(N)c2cc3ccccc3s2)ccc1Cl]

To a mixture of 1-(benzothiophen-2-yl)-2-[4-chloro-3-(3-methoxypropoxy)phenyl]ethanone (770 mg, 2 mmol) and ammonium acetate (2.31 g, 30 mmol) in methanol (10 mL) and dichloroethane (5 mL) was added $NaBH_3CN$ (252 mg, 4 mmol). The resulting mixture was heated at 65° C. for 16 hrs. After being cooled to rt, the reaction mixture was basified by 2 M NaOH aqueous solution to pH=12, and then diluted with water. The resulting mixture was extracted with DCM for three times. The combined organic layers were washed with brine, dried over anhydrous $Na_2SO_4$ and concentrated under reduced pressure to give crude 1-(benzothiophen-2-yl)-2-[4-chloro-3-(3-methoxypropoxy)phenyl]ethanamine (739 mg) as a brown oil, which was used directly in the next step without further purification.

Step 4: Preparation of N-[1-(benzothiophen-2-yl)-2-[4-chloro-3-(3-methoxypropoxy)phenyl]ethyl]formamide

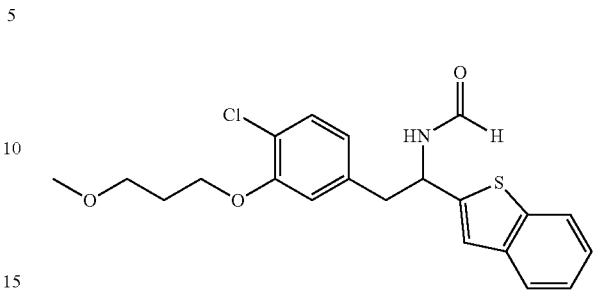

A mixture of crude 1-(benzothiophen-2-yl)-2-[4-chloro-3-(3-methoxypropoxy)phenyl]ethanamine (739 mg, 2 mmol) and formic acid (0.1 mL) in ethyl formate (10 mL) was heated at 90° C. for 2 hrs. After being cooled to rt, the mixture was concentrated under reduced pressure to give N-[1-(benzothiophen-2-yl)-2-[4-chloro-3-(3-methoxypropoxy)phenyl]ethyl]formamide (756 mg) as a brown oil, which was used directly in the next step without further purification.

Step 5: Preparation of 3-(benzothiophen-2-yl)-7-chloro-6-(3-methoxypropoxy)-3,4-dihydroisoquinoline

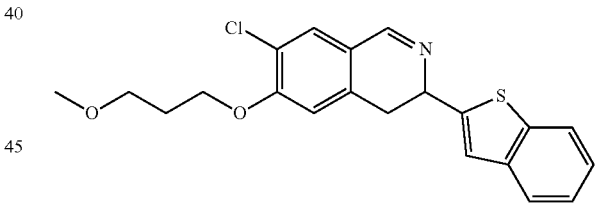

To a solution of N-[1-(benzothiophen-2-yl)-2-[4-chloro-3-(3-methoxypropoxy)phenyl]ethyl]formamide (756 mg, 1.9 mmol) in $CH_3CN$ (10 mL) was added $POCl_3$ (291 mg, 1.9 mmol). The mixture was heated at 80° C. for 2 hrs. After being cooled to rt, the mixture was concentrated under reduced pressure. The residue was dissolved in $CH_3CN$ (10 mL) and then basified by ammonia water to pH=10 at 0° C. The resulting mixture was extracted with DCM. The organic layer was washed with brine, dried over anhydrous $Na_2SO_4$ and concentrated under reduced pressure to give crude 3-(benzothiophen-2-yl)-7-chloro-6-(3-methoxypropoxy)-3,4-dihydroisoquinoline (727 mg) as a brown oil, which was used directly in the next step without further purification.

Step 6: Preparation of ethyl 6-(benzothiophen-2-yl)-10-chloro-9-(3-methoxypropoxy)-2-oxo-1,6,7,11b-tetrahydrobenzo[a]quinolizine-3-carboxylate

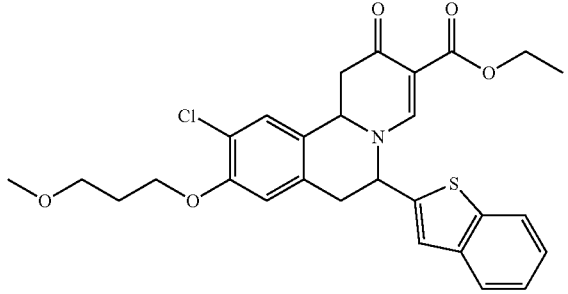 [SMILES: CCOC(=O)C1=CN2C(c3cc4ccccc4s3)Cc3cc(OCCCOC)c(Cl)cc3C2CC1=O]

A mixture of crude 3-(benzothiophen-2-yl)-7-chloro-6-(3-methoxypropoxy)-3,4-dihydroisoquinoline (727 mg, 1.9 mmol) and ethyl 2-(ethoxymethylene)-3-oxo-butanoate (1.06 g, 5.7 mmol) in ethanol (15 mL) was refluxed for 24 hrs. The mixture was concentrated under reduced pressure to give crude ethyl 6-(benzothiophen-2-yl)-10-chloro-9-(3-methoxypropoxy)-2-oxo-1,6,7,1 b-tetrahydrobenzo[a]quinolizine-3-carboxylate (1.70 g), which was used directly in the next step without further purification.

Step 7: Preparation of ethyl 6-(benzothiophen-2-yl)-10-chloro-9-(3-methoxypropoxy)-2-oxo-6,7-dihydrobenzo[a]quinolizine-3-carboxylate

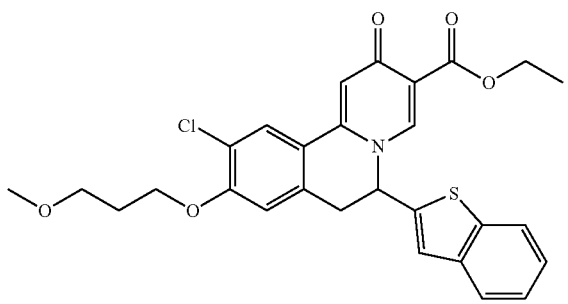 [SMILES: CCOC(=O)c1cn2c(cc1=O)-c1cc(Cl)c(OCCCOC)cc1CC2c1cc2ccccc2s1]

A mixture of crude ethyl 6-(benzothiophen-2-yl)-10-chloro-9-(3-methoxypropoxy)-2-oxo-1,6,7,11b-tetrahydrobenzo[a]quinolizine-3-carboxylate (1.70 g, 1.9 mmol) and p-chloranil (467 mg, 1.9 mmol) in DME (10 mL) was heated at 70° C. for 3 hrs. After being cooled to rt, the mixture was partitioned between DCM and water. The organic layer was washed with saturated NaHCO$_3$ aqueous solution (50 mL) 5 times and brine, dried over anhydrous Na$_2$SO$_4$, and concentrated under reduced pressure to give crude ethyl 6-(benzothiophen-2-yl)-10-chloro-9-(3-methoxypropoxy)-2-oxo-6,7-dihydrobenzo[a]quinolizine-3-carboxylate (2.01 g) as a brown oil, which was used directly in next step without further purification.

Step 8: Preparation of 6-(benzothiophen-2-yl)-10-chloro-9-(3-methoxypropoxy)-2-oxo-6,7-dihydrobenzo[a]quinolizine-3-carboxylic Acid

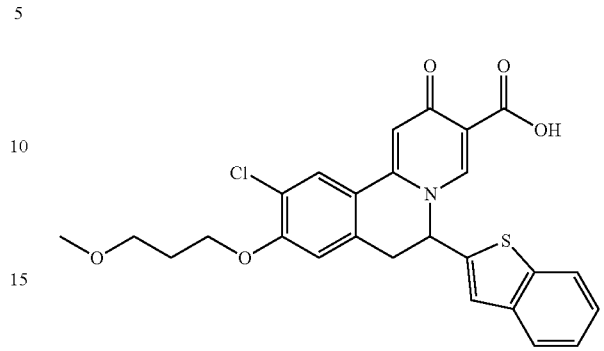

To a mixture of crude ethyl 6-(benzothiophen-2-yl)-10-chloro-9-(3-methoxypropoxy)-2-oxo-6,7-dihydrobenzo[a]quinolizine-3-carboxylate (2.01 g, 1.9 mmol) in methanol (16 mL) and H$_2$O (4 mL) was added LiOH.H$_2$O (958 mg, 22.8 mmol). The resulting mixture was stirred at rt overnight, and then acidified by 1 M hydrochloric acid to pH=2-3. The mixture was extracted with DCM for three times. The combined organic layers were washed with brine, dried over anhydrous Na$_2$SO$_4$ and concentrated under reduced pressure. The residue was purified by column chromatography to give crude product as a brown solid, which was recrystallized from diethyl ether and EtOH to afford 6-(benzothiophen-2-yl)-10-chloro-9-(3-methoxypropoxy)-2-oxo-6,7-dihydrobenzo[a]quinolizine-3-carboxylic acid (80 mg) as a light-brown solid. $^1$HNMR (400 MHz, DMSO-d6) δ: 8.95 (s, 1H), 8.14 (s, 1H), 7.81-7.76 (m, 1H), 7.75-7.69 (m, 1H), 7.37 (s, 1H), 7.34-7.28 (m, 2H), 7.24 (s, 1H), 6.40 (s, 1H), 4.23-4.09 (m, 2H), 3.85-3.75 (m, 1H), 3.60-3.50 (m, 1H), 3.49-3.41 (m, 2H), 3.20 (m, 3H), 2.00-1.88 (m, 2H). MS obsd. (ESI$^+$) [(M+H)$^+$]: 496.

Biological Examples

Example 38 Materials and Methods

HBV Cell Line

HepG2.2.15 cells (Acs et al. *Proc Natl Acad Sci USA*, 84, (1987), 4641-4), a constitutively HBV-expressing cell line were cultured in DMEM+Glutamax-I medium (Invitrogen, Carlsbad, Calif., USA), supplemented with 10% fetal bovine serum (Invitrogen) and G418 (Invitrogen) at a final concentration of 200 mg/L and maintained in 5% CO$_2$ at 37° C.

HBsAg Assay

HepG2.2.15 cells were seeded in duplicate into white, 96-well plates at 1.5×10$^4$ cells/well. The cells were treated with a three-fold serial dilution series of the compounds in DMSO. The final DMSO concentration in all wells was 1% and DMSO was used as no drug control.

The HBsAg chemiluminescence immunoassay (CLIA) kit (Autobio Diagnostics Co., Zhengzhou, China, Catalog number: CL0310-2) was used to measure the levels of secreted HBV antigens semi-quantitatively. For the detection 50 μL/well culture supernatant was used and HBsAg was quantified using HBsAg chemiluminescence immunoassay (CLIA) kit (Autobio Diagnostics Co., Zhengzhou, China, Catalog number: CL0310-2), 50 μL of the supernatant was transferred to the CLIA assay plate and 50 μL of enzyme conjugate reagent was added into each well. The plates were sealed and gently agitated for 1 hour at room temperature. The supernatant-enzyme-mixture was discarded and wells were washed 6 times with 300 µL of PBS. The residual liquid was removed by plating the CLIA plate right side down on absorbent tissue paper. 25 µL of substrates A and B were added to each well. Luminance was measured using a luminometer (Mithras LB 940 Multimode Microplate Reader) after 10 minutes incubation. Dose-response curves were generated and the $IC_{50}$ value was extrapolated by using the E-WorkBook Suite (ID Business Solutions Ltd., Guildford, UK). The $IC_{50}$ was defined as the compound concentration (or conditioned media log dilution) at which HBsAg secretion was reduced by 50% compared to the no drug control.

The compounds of the present invention were tested for their activity to inhibit HBsAg as described herein. The Examples were tested in the above assay and found to have $IC_{50}$ below 25.0 M. Particular compounds of formula I were found to have $IC_{50}$ below 0.100 µM. More Particular compounds of formula I were found to have $IC_{50}$ below 0.010 M. Results of HBsAg assay are given in Table 1.

TABLE 1

Activity data of particular compounds

| Example No. | $IC_{50}$ (µM) |
|---|---|
| 1 | 0.064 |
| 2 | 0.01 |
| 3 | 0.003 |
| 4 | 1.16 |
| 5 | 0.8 |
| 6 | 1.93 |
| 7 | 0.009 |
| 8 | 0.094 |
| 9 | 0.083 |
| 10 | 0.01 |
| 11 | 0.17 |
| 12 | 0.005 |
| 13 | 0.006 |
| 14 | 0.002 |
| 15 | 0.002 |
| 16 | 0.009 |
| 17 | 0.018 |
| 18 | 0.097 |
| 19 | 0.005 |
| 20 | 0.037 |
| 21 | 0.006 |
| 22 | 0.021 |
| 23 | 0.018 |
| 24 | 0.01 |
| 25 | 0.003 |
| 26 | 0.004 |
| 27 | 0.003 |
| 28 | 0.01 |
| 29 | 0.064 |
| 30 | 0.32 |
| 31 | 0.004 |
| 32 | 0.11 |
| 33 | 0.035 |
| 34 | 0.024 |
| 35 | 0.022 |
| 36 | 0.003 |
| 37 | 4.42 |

HBV DNA Assay

The assay employs real-time qPCR (TaqMan) to directly measure extracellular HBV DNA copy number. HepG2.2.15 cells were plated in 96-well microtiter plates. Only the interior wells were utilized to reduce "edge effects" observed during cell culture, the exterior wells were filled with complete medium to help minimize sample evaporation. On the following day, the HepG2.2.15 cells were washed and the medium was replaced with complete medium containing various concentrations of a test compound in triplicate. 3TC was used as the positive control, while media alone was added to cells as a negative control (virus control, VC). Three days later, the culture medium was replaced with fresh medium containing the appropriately diluted drug. Six days following the initial administration of the test compound, the cell culture supernatant was collected, treated with pronase and then used in a real-time qPCR/TaqMan assay to determine HBV DNA copy numbers. Antiviral activity was calculated from the reduction in HBV DNA levels ($IC_{50}$).

The compounds of the present invention were tested for their activity to anti HBV DNA production as described herein. The Examples were tested in the above assay and found to have $IC_{50}$ below 25.0 µM. Particular compounds of formula I were found to have $IC_{50}$ below 0.10 µM. Results of HBV DNA assay are given in Table 2.

TABLE 2

Anti HBV DNA production activity in HepG2.2.15 cells

| Example No. | $IC_{50}$ (µM) |
|---|---|
| 7 | <0.032 |
| 8 | <0.032 |
| 15 | <0.032 |

The invention claimed is:
1. A compound of formula I

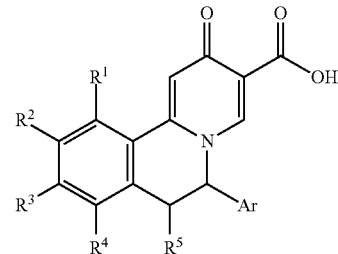

wherein
$R^1$, $R^2$, $R^3$ and $R^4$ are independently selected from $C_{1-6}$alkyl, halo$C_{1-6}$alkyl, hydrogen, halogen, cyano, amino, $C_{1-6}$alkylamino, di$C_{1-6}$alkylamino, pyrrolidinyl and $OR^6$;
$R^5$ is hydrogen or $C_{1-6}$alkyl;
$R^6$ is hydrogen; $C_{1-6}$alkyl; halo$C_{1-6}$alkyl; $C_{3-7}$cycloalkyl$C_{1-6}$alkyl; phenyl$C_{1-6}$alkyl; hydroxy$C_{1-6}$alkyl; $C_{1-6}$alkoxy$C_{1-6}$alkyl; carboxy$C_{1-6}$alkyl; $C_{1-6}$alkylsulfanyl$C_{1-6}$alkyl; $C_{1-6}$alkylsulfonyl$C_{1-6}$alkyl; cyano$C_{1-6}$alkyl; amino$C_{1-6}$alkyl; $C_{1-6}$alkylamino$C_{1-6}$alkyl; di$C_{1-6}$alkylamino$C_{1-6}$alkyl; $C_{1-6}$alkylcarbonylamino$C_{1-6}$alkyl; $C_{1-6}$alkylsulfonylamino$C_{1-6}$ alkyl; $C_{1-6}$alkoxycarbonylamino$C_{1-6}$alkyl; pyrazolyl$C_{1-6}$alkyl; triazolyl$C_{1-6}$alkyl; or heterocycloalkyl$C_{1-6}$alkyl, wherein heterocycloalkyl is N-containing monocyclic heterocycloalkyl; and
Ar is phenyl; phenyl substituted by one, two or three groups independently selected from $C_{1-6}$alkyl, $C_{1-6}$alkoxy, hydroxy, halogen and phenyl$C_{1-6}$alkoxy; thienyl; thienyl substituted by one, two or three groups independently selected from $C_{1-6}$alkyl, $C_{1-6}$alkoxy, hydroxy, halogen and phenyl$C_{1-6}$alkoxy; benzothiophenyl; benzothiophenyl substituted by one, two or three groups independently selected from $C_{1-6}$alkyl, $C_{1-6}$alkoxy, hydroxy, halogen and phenyl$C_{1-6}$alkoxy; pyridinyl; pyridinyl substituted by one, two or three groups independently selected from $C_{1-6}$alkyl, $C_{1-6}$alkoxy, hydroxy, halogen and phenyl$C_{1-6}$alkoxy; pyrimidinyl; pyrimidinyl substituted by one, two or three groups independently selected from $C_{1-6}$alkyl, $C_{1-6}$alkoxy, hydroxy, halogen and phenyl$C_{1-6}$alkoxy; pyrrolyl; pyrrolyl substituted by one, two or three groups independently selected from $C_{1-6}$alkyl, $C_{1-6}$alkoxy, hydroxy, halogen and phenyl$C_{1-6}$alkoxy; pyrazolyl; pyrazolyl substituted by one, two or three groups independently selected from $C_{1-6}$alkyl, $C_{1-6}$alkoxy, hydroxy, halogen and phenyl$C_{1-6}$alkoxy; thiazolyl; or thiazolyl substituted by one, two or three groups independently selected from $C_{1-6}$alkyl, $C_{1-6}$alkoxy, hydroxy, halogen and phenyl$C_{1-6}$alkoxy;

or a pharmaceutically acceptable salt or enantiomer thereof.

2. A compound according to claim 1, wherein
$R^1$ is hydrogen;
$R^2$ is hydrogen, halogen or $C_{1-6}$alkoxy;
$R^3$ is $C_{1-6}$alkyl, pyrrolidinyl or $OR^6$;
$R^4$ is $C_{1-6}$alkyl or hydrogen;
$R^5$ is hydrogen;
$R^6$ is $C_{1-6}$alkyl, halo$C_{1-6}$alkyl, $C_{3-7}$cycloalkyl$C_{1-6}$alkyl, phenyl$C_{1-6}$alkyl, hydroxy$C_{1-6}$alkyl, $C_{1-6}$alkoxy$C_{1-6}$alkyl, carboxy$C_{1-6}$alkyl, $C_{1-6}$alkylsulfanyl$C_{1-6}$alkyl, $C_{1-6}$alkylsulfonyl$C_{1-6}$alkyl, cyano$C_{1-6}$alkyl, amino$C_{1-6}$alkyl, $C_{1-6}$alkylcarbonylamino$C_{1-6}$alkyl, $C_{1-6}$alkylsulfonylamino$C_{1-6}$alkyl, $C_{1-6}$alkoxycarbonylamino$C_{1-6}$alkyl, pyrazolyl$C_{1-6}$alkyl, triazolyl$C_{1-6}$alkyl, piperidyl$C_{1-6}$alkyl, morpholinyl$C_{1-6}$alkyl or 2-oxopyrrolidinyl$C_{1-6}$alkyl; and
Ar is phenyl; phenyl substituted by $C_{1-6}$alkyl, $C_{1-6}$alkoxy, hydroxy, halogen or phenyl$C_{1-6}$alkoxy; thienyl; thienyl substituted by $C_{1-6}$alkyl; or benzothiophenyl;

or a pharmaceutically acceptable salt or enantiomer thereof.

3. A compound according to claim 1, or a pharmaceutically acceptable salt or enantiomer thereof, wherein $R^1$ is hydrogen, $R^4$ is hydrogen and $R^5$ is hydrogen.

4. A compound according to claim 1, or a pharmaceutically acceptable salt or enantiomer thereof, wherein $R^2$ is $C_{1-6}$alkoxy.

5. A compound according to claim 1, or a pharmaceutically acceptable salt or enantiomer thereof, wherein $R^2$ is methoxy.

6. A compound according to claim 1, or a pharmaceutically acceptable salt or enantiomer thereof, wherein $R^3$ is pyrrolidinyl or $OR^6$, wherein $R^6$ is $C_{1-6}$alkyl, halo$C_{1-6}$alkyl, $C_{3-7}$cycloalkyl$C_{1-6}$alkyl, hydroxy$C_{1-6}$alkyl, $C_{1-6}$alkoxy$C_{1-6}$alkyl, carboxy$C_{1-6}$alkyl, $C_{1-6}$alkylsulfanyl$C_{1-6}$alkyl, cyano$C_{1-6}$alkyl, amino$C_{1-6}$alkyl, $C_{1-6}$alkylcarbonylamino$C_{1-6}$alkyl, $C_{1-6}$alkylsulfonylamino$C_{1-6}$alkyl or $C_{1-6}$alkoxycarbonylamino$C_{1-6}$alkyl.

7. A compound according to claim 1, or a pharmaceutically acceptable salt or enantiomer thereof, wherein $R^3$ is $OR^6$, wherein $R^6$ is methyl, isobutyl, trifluoroethyl, cyclopropylmethyl, cyanopropyl, hydroxypropyl, hydroxyhexyl, hydroxydimethylpropyl, methoxypropyl, carboxypropyl, methylsulfanylpropyl, aminohexyl, methylcarbonylaminohexyl, methylsulfonylaminohexyl or methoxycarbonylaminohexyl.

8. A compound according to claim 1, or a pharmaceutically acceptable salt or enantiomer thereof, wherein Ar is phenyl; phenyl substituted by $C_{1-6}$alkyl or halogen; thienyl; or thienyl substituted by $C_{1-6}$alkyl.

9. A compound according to claim 1, or a pharmaceutically acceptable salt or enantiomer thereof, wherein Ar is phenyl; phenyl substituted by methyl, fluoro or chloro; thienyl; or thienyl substituted by methyl.

10. A compound according to claim 1, wherein
$R^1$ is hydrogen;
$R^2$ is $C_{1-6}$alkoxy;
$R^3$ is pyrrolidinyl or $OR^6$;
$R^4$ is hydrogen;
$R^5$ is hydrogen;
$R^6$ is $C_{1-6}$alkyl, halo$C_{1-6}$alkyl, $C_{3-7}$cycloalkyl$C_{1-6}$alkyl, hydroxy$C_{1-6}$alkyl, $C_{1-6}$alkoxy$C_{1-6}$alkyl or $C_{1-6}$alkylsulfanyl$C_{1-6}$alkyl; and
Ar is phenyl substituted by $C_{1-6}$alkyl; or thienyl;
or a pharmaceutically acceptable salt or enantiomer thereof.

11. A compound according to claim 1, wherein
$R^1$ is hydrogen;
$R^2$ is methoxy;
$R^3$ is pyrrolidinyl or $OR^6$;
$R^4$ is hydrogen;
$R^5$ is hydrogen;
$R^6$ is isobutyl, trifluoroethyl, cyclopropylmethyl, hydroxydimethylpropyl, methoxypropyl or methylsulfanylpropyl; and
Ar is phenyl substituted by methyl; or thienyl;
or a pharmaceutically acceptable salt or enantiomer thereof.

12. A compound according to claim 1, selected from
10-Methoxy-9-(3-methoxypropoxy)-2-oxo-6-phenyl-6,7-dihydrobenzo[a]quinolizine-3-carboxylic acid;
10-Methoxy-9-(3-methoxypropoxy)-2-oxo-6-(3-thienyl)-6,7-dihydrobenzo[a]quinolizine-3-carboxylic acid;
10-Methoxy-9-(3-methoxypropoxy)-2-oxo-6-(2-thienyl)-6,7-dihydrobenzo[a]quinolizine-3-carboxylic acid;
6-(4-Hydroxyphenyl)-10-methoxy-9-(3-methoxypropoxy)-2-oxo-6,7-dihydrobenzo[a]quinolizine-3-carboxylic acid;
10-Methoxy-6-(4-methoxyphenyl)-9-(3-methoxypropoxy)-2-oxo-6,7-dihydrobenzo[a]quinolizine-3-carboxylic acid;
6-(4-Benzyloxyphenyl)-10-methoxy-9-(3-methoxypropoxy)-2-oxo-6,7-dihydrobenzo[a]quinolizine-3-carboxylic acid;
10-Methoxy-9-(3-methoxypropoxy)-6-(4-methyl-2-thienyl)-2-oxo-6,7-dihydrobenzo[a]quinolizine-3-carboxylic acid;
6-(3-Chlorophenyl)-10-methoxy-9-(3-methoxypropoxy)-2-oxo-6,7-dihydrobenzo[a]quinolizine-3-carboxylic acid;
6-(4-Fluorophenyl)-10-methoxy-9-(3-methoxypropoxy)-2-oxo-6,7-dihydrobenzo[a]quinolizine-3-carboxylic acid;
10-Methoxy-9-(3-methoxypropoxy)-6-(o-tolyl)-2-oxo-6,7-dihydrobenzo[a]quinolizine-3-carboxylic acid;
9-Methoxy-8-methyl-2-oxo-6-(2-thienyl)-6,7-dihydrobenzo[a]quinolizine-3-carboxylic acid;
9-Benzyloxy-10-methoxy-2-oxo-6-(2-thienyl)-6,7-dihydrobenzo[a]quinolizine-3-carboxylic acid;
9,10-Dimethoxy-2-oxo-6-(2-thienyl)-6,7-dihydrobenzo[a]quinolizine-3-carboxylic acid;
9-Isobutoxy-10-methoxy-2-oxo-6-(2-thienyl)-6,7-dihydrobenzo[a]quinolizine-3-carboxylic acid;

9-(Cyclopropylmethoxy)-10-methoxy-2-oxo-6-(2-thienyl)-6,7-dihydrobenzo[a]quinolizine-3-carboxylic acid;
10-Methoxy-2-oxo-9-(3-pyrazol-1-ylpropoxy)-6-(2-thienyl)-6,7-dihydrobenzo[a]quinolizine-3-carboxylic acid;
9-(3-Hydroxypropoxy)-10-methoxy-2-oxo-6-(2-thienyl)-6,7-dihydrobenzo[a]quinolizine-3-carboxylic acid;
10-Methoxy-2-oxo-9-[3-(1-piperidyl)propoxy]-6-(2-thienyl)-6,7-dihydrobenzo[a]quinolizine-3-carboxylic acid;
9-(3-Cyanopropoxy)-10-methoxy-2-oxo-6-(2-thienyl)-6,7-dihydrobenzo[a]quinolizine-3-carboxylic acid;
10-Methoxy-2-oxo-9-[2-(2-oxopyrrolidin-1-yl)ethoxy]-6-(2-thienyl)-6,7-dihydrobenzo[a]quinolizine-3-carboxylic acid;
9-[6-(tert-Butoxycarbonylamino)hexoxy]-10-methoxy-2-oxo-6-(2-thienyl)-6,7-dihydrobenzo[a]quinolizine-3-carboxylic acid;
9-(6-Aminohexoxy)-10-methoxy-2-oxo-6-(2-thienyl)-6,7-dihydrobenzo[a]quinolizine-3-carboxylic acid formate;
9-(6-Acetamidohexoxy)-10-methoxy-2-oxo-6-(2-thienyl)-6,7-dihydrobenzo[a]quinolizine-3-carboxylic acid;
9-[6-(Methanesulfonamido)hexoxy]-10-methoxy-2-oxo-6-(2-thienyl)-6,7-dihydrobenzo[a]quinolizine-3-carboxylic acid;
9-(6-Hydroxyhexoxy)-10-methoxy-2-oxo-6-(2-thienyl)-6,7-dihydrobenzo[a]quinolizine-3-carboxylic acid;
9-(3-Hydroxy-2,2-dimethyl-propoxy)-10-methoxy-2-oxo-6-(2-thienyl)-6,7-dihydrobenzo[a]quinolizine-3-carboxylic acid;
10-Methoxy-2-oxo-6-(2-thienyl)-9-(2,2,2-trifluoroethoxy)-6,7-dihydrobenzo[a]quinolizine-3-carboxylic acid;
10-Methoxy-9-(3-morpholinopropoxy)-2-oxo-6-(2-thienyl)-6,7-dihydrobenzo[a]quinolizine-3-carboxylate;
10-Methoxy-2-oxo-6-(2-thienyl)-9-[3-(1,2,4-triazol-1-yl)propoxy]-6,7-dihydrobenzo[a]quinolizine-3-carboxylic acid;
9-(3-Carboxypropoxy)-10-methoxy-2-oxo-6-(2-thienyl)-6,7-dihydrobenzo[a]quinolizine-3-carboxylic acid;
10-Methoxy-9-(3-methylsulfanylpropoxy)-2-oxo-6-(2-thienyl)-6,7-dihydrobenzo[a]quinolizine-3-carboxylic acid;
10-Methoxy-9-(3-methylsulfonylpropoxy)-2-oxo-6-(2-thienyl)-6,7-dihydrobenzo[a]quinolizine-3-carboxylic acid;
10-Methoxy-9-methyl-2-oxo-6-(2-thienyl)-6,7-dihydrobenzo[a]quinolizine-3-carboxylic acid;
9-Ethyl-10-methoxy-2-oxo-6-(2-thienyl)-6,7-dihydrobenzo[a]quinolizine-3-carboxylic acid;
10-Methoxy-2-oxo-9-propyl-6-(2-thienyl)-6,7-dihydrobenzo[a]quinolizine-3-carboxylic acid;
10-Methoxy-2-oxo-9-pyrrolidin-1-yl-6-(2-thienyl)-6,7-dihydrobenzo[a]quinolizine-3-carboxylic acid; and
6-(Benzothiophen-2-yl)-10-chloro-9-(3-methoxypropoxy)-2-oxo-6,7-dihydrobenzo[a]quinolizine-3-carboxylic acid;
or a pharmaceutically acceptable salt or enantiomer thereof.

13. A compound according to claim 1, selected from
10-Methoxy-9-(3-methoxypropoxy)-2-oxo-6-(3-thienyl)-6,7-dihydrobenzo[a]quinolizine-3-carboxylic acid;
10-Methoxy-9-(3-methoxypropoxy)-2-oxo-6-(2-thienyl)-6,7-dihydrobenzo[a]quinolizine-3-carboxylic acid;

10-Methoxy-9-(3-methoxypropoxy)-6-(o-tolyl)-2-oxo-6,7-dihydrobenzo[a]quinolizine-3-carboxylic acid;
9-Isobutoxy-10-methoxy-2-oxo-6-(2-thienyl)-6,7-dihydrobenzo[a]quinolizine-3-carboxylic acid;
9-(Cyclopropylmethoxy)-10-methoxy-2-oxo-6-(2-thienyl)-6,7-dihydrobenzo[a]quinolizine-3-carboxylic acid;
9-(3-Hydroxy-2,2-dimethyl-propoxy)-10-methoxy-2-oxo-6-(2-thienyl)-6,7-dihydrobenzo[a]quinolizine-3-carboxylic acid;
10-Methoxy-2-oxo-6-(2-thienyl)-9-(2,2,2-trifluoroethoxy)-6,7-dihydrobenzo[a]quinolizine-3-carboxylic acid;
10-Methoxy-9-(3-methylsulfanylpropoxy)-2-oxo-6-(2-thienyl)-6,7-dihydrobenzo[a]quinolizine-3-carboxylic acid; and
10-Methoxy-2-oxo-9-pyrrolidin-1-yl-6-(2-thienyl)-6,7-dihydrobenzo[a]quinolizine-3-carboxylic acid;
or a pharmaceutically acceptable salt or enantiomer thereof.

14. A process for the preparation of a compound according to claim 1, or a pharmaceutically acceptable salt or enantiomer thereof, comprising
(a) hydrolysis of a compound of formula (A)

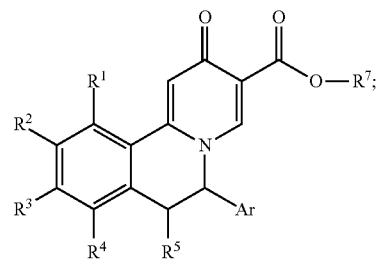

(A)

(b) hydrolysis of a compound of formula (B)

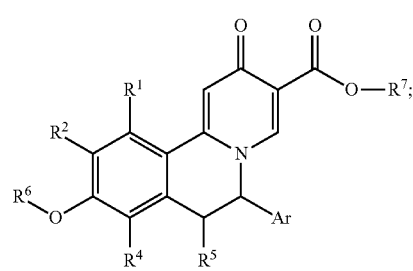

(B)

wherein $R^7$ is $C_{1-6}$alkyl.

15. A pharmaceutical composition comprising a compound according to claim 1, or a pharmaceutically acceptable salt or enantiomer thereof, and a therapeutically inert carrier.

16. A method for the treatment of hepatitis B virus infection, which method comprises administering an effective amount of a compound according to claim 1, or a pharmaceutically acceptable salt or enantiomer thereof to a mammal having an HBV infection.

17. A method for the inhibition of HBsAg production or secretion, which method comprises administering an effective amount of a compound according to claim 1, or a pharmaceutically acceptable salt or enantiomer thereof, to a mammal.

* * * * *